(12) United States Patent
Whitman

(10) Patent No.: US 9,138,211 B2
(45) Date of Patent: Sep. 22, 2015

(54) TISSUE REPAIR IMPLANT AND DELIVERY DEVICE AND METHOD

(75) Inventor: Michael P. Whitman, New Hope, PA (US)

(73) Assignee: MICRO INTERVENTIONAL DEVICES, INC., New Hope, PA (US)

( * ) Notice: Subject to any disclaimer, the term of this patent is extended or adjusted under 35 U.S.C. 154(b) by 825 days.

(21) Appl. No.: 13/010,774

(22) Filed: Jan. 20, 2011

(65) Prior Publication Data

US 2011/0178535 A1      Jul. 21, 2011

Related U.S. Application Data

(60) Provisional application No. 61/296,868, filed on Jan. 20, 2010.

(51) Int. Cl.
*A61B 17/00* (2006.01)
*A61B 17/10* (2006.01)
*A61B 17/064* (2006.01)
*A61B 17/04* (2006.01)

(52) U.S. Cl.
CPC .......... *A61B 17/0057* (2013.01); *A61B 17/0401* (2013.01); *A61B 17/10* (2013.01); *A61B 2017/00575* (2013.01); *A61B 2017/00579* (2013.01); *A61B 2017/00632* (2013.01); *A61B 2017/0408* (2013.01); *A61B 2017/0412* (2013.01); *A61B 2017/0427* (2013.01); *A61B 2017/0435* (2013.01); *A61B 2017/0437* (2013.01); *A61B 2017/0464* (2013.01); *A61B 2017/0647* (2013.01); *A61B 2017/0648* (2013.01)

(58) Field of Classification Search
CPC .... A61B 17/0057; A61B 17/12168–17/12177; A61B 2017/00575; A61B 2017/00592; A61B 2017/00597; A61B 2017/0061; A61B 2017/00619; A61B 2017/00623; A61B 2017/00632; A61B 2017/00646; A61B 2017/00659; A61F 2002/0072
USPC .................. 606/213, 139, 142–143, 151, 219
See application file for complete search history.

(56) References Cited

U.S. PATENT DOCUMENTS 3,897,035 A    7/1975 Solo
3,959,960 A    6/1976 Santos
(Continued)

FOREIGN PATENT DOCUMENTS

EP    0 790 038    8/1997
EP    1 595 504    11/2005
(Continued)

OTHER PUBLICATIONS

International Search Report and Written Opinion, dated Mar. 11, 2011, issued in corresponding International Application No. PCT/US2011/021946.

(Continued)

*Primary Examiner* — Julian W Woo
*Assistant Examiner* — Shaun L David
(74) *Attorney, Agent, or Firm* — Kenyon & Kenyon LLP

(57) ABSTRACT

A device having a temporary frame configured to carry an implant, the temporary frame being selectably movable between a retracted position and a deployed position, the implant being in a relaxed state when carried by the frame in the retracted position, the implant being in a taut state when carried by the frame in the deployed position.

42 Claims, 50 Drawing Sheets

(56) References Cited

U.S. PATENT DOCUMENTS

| | | | |
|---|---|---|---|
| 4,204,541 A | 5/1980 | Kapitanov |
| 4,488,523 A | 12/1984 | Shichman |
| 4,669,473 A | 6/1987 | Richards et al. |
| 4,741,330 A | 5/1988 | Hayhurst |
| 4,873,976 A | 10/1989 | Schreiber |
| 4,884,572 A | 12/1989 | Bays et al. |
| 4,969,892 A | 11/1990 | Burton et al. |
| 4,978,265 A | 12/1990 | De Wan |
| 5,059,206 A | 10/1991 | Winters |
| 5,127,412 A | 7/1992 | Cosmetto et al. |
| 5,356,424 A | 10/1994 | Buzerak et al. |
| 5,370,661 A | 12/1994 | Branch |
| 5,372,146 A | 12/1994 | Branch |
| 5,478,353 A | 12/1995 | Yoon |
| 5,505,735 A | 4/1996 | Li |
| 5,562,704 A | 10/1996 | Tamminmaki et al. |
| 5,569,264 A | 10/1996 | Tamminmaki et al. |
| 5,584,859 A | 12/1996 | Brotz |
| 5,601,557 A | 2/1997 | Hayhurst |
| 5,694,782 A | 12/1997 | Alsenz |
| 5,782,844 A | 7/1998 | Yoon et al. |
| 5,792,142 A | 8/1998 | Galitzer |
| 5,814,051 A | 9/1998 | Wenstrom, Jr. |
| 5,860,991 A | 1/1999 | Klein et al. |
| 5,964,782 A | 10/1999 | Lafontaine et al. |
| 5,976,127 A | 11/1999 | Lax |
| 5,976,139 A | 11/1999 | Bramlet |
| 5,993,475 A | 11/1999 | Lin et al. |
| 6,010,525 A | 1/2000 | Bonutti et al. |
| 6,027,523 A | 2/2000 | Schmieding |
| 6,030,410 A | 2/2000 | Zurbrugg |
| 6,120,525 A | 9/2000 | Westcott |
| 6,159,234 A | 12/2000 | Bonutti et al. |
| 6,174,323 B1 | 1/2001 | Biggs et al. |
| 6,231,561 B1 | 5/2001 | Frazier et al. |
| 6,231,592 B1 | 5/2001 | Bonutti et al. |
| 6,331,182 B1 | 12/2001 | Tiefenbrun et al. |
| 6,387,113 B1 | 5/2002 | Hawkins et al. |
| 6,468,293 B2 | 10/2002 | Bonutti et al. |
| 6,500,184 B1 | 12/2002 | Chan et al. |
| 6,569,187 B1 | 5/2003 | Bonutti et al. |
| 6,663,633 B1 | 12/2003 | Pierson, III |
| 6,692,499 B2 | 2/2004 | Tormala et al. |
| 6,884,251 B2 | 4/2005 | Spence et al. |
| 6,966,916 B2 | 11/2005 | Kumar |
| 7,037,315 B2 | 5/2006 | Sancoff et al. |
| 7,087,073 B2 | 8/2006 | Bonutti |
| 7,104,949 B2 | 9/2006 | Anderson et al. |
| 7,147,652 B2 | 12/2006 | Bonutti et al. |
| 7,166,127 B2 | 1/2007 | Spence et al. |
| 7,195,634 B2 | 3/2007 | Schmieding et al. |
| 7,220,265 B2 | 5/2007 | Chanduszko et al. |
| 7,235,090 B2 | 6/2007 | Buckman et al. |
| 7,361,185 B2 | 4/2008 | O'Malley et al. |
| 7,390,329 B2 | 6/2008 | Westra et al. |
| 7,416,554 B2 | 8/2008 | Lam et al. |
| 7,651,509 B2 | 1/2010 | Bojarski et al. |
| 7,736,378 B2 | 6/2010 | Maahs et al. |
| 7,780,702 B2 | 8/2010 | Shiono |
| 7,833,238 B2 | 11/2010 | Nakao |
| 7,850,712 B2 | 12/2010 | Conlon et al. |
| 8,241,227 B2 | 8/2012 | Ohnishi et al. |
| 8,337,525 B2 | 12/2012 | Stone et al. |
| 8,361,113 B2 | 1/2013 | Stone et al. |
| 8,382,776 B2 | 2/2013 | Ducharme |
| 8,425,539 B2 | 4/2013 | Binmoeller et al. |
| 2003/0074021 A1 | 4/2003 | Morriss et al. |
| 2003/0092969 A1 | 5/2003 | O'Malley et al. |
| 2003/0097148 A1 | 5/2003 | Valimaa et al. |
| 2004/0087981 A1 | 5/2004 | Berube et al. |
| 2004/0138707 A1 | 7/2004 | Greenhalgh |
| 2004/0220596 A1 | 11/2004 | Frazier et al. |
| 2004/0220610 A1* | 11/2004 | Kreidler et al. ............... 606/200 |
| 2005/0021057 A1 | 1/2005 | St. Goar et al. |
| 2005/0038449 A1 | 2/2005 | Sancoff et al. |
| 2005/0055027 A1 | 3/2005 | Yeung et al. |
| 2005/0075654 A1 | 4/2005 | Kelleher |
| 2005/0125011 A1* | 6/2005 | Spence et al. ............... 606/144 |
| 2005/0187568 A1 | 8/2005 | Klenk et al. |
| 2005/0228413 A1 | 10/2005 | Binmoeller et al. |
| 2005/0234508 A1 | 10/2005 | Cummins et al. |
| 2005/0251175 A1 | 11/2005 | Weisenburgh et al. |
| 2005/0256532 A1* | 11/2005 | Nayak et al. ............... 606/151 |
| 2005/0283189 A1 | 12/2005 | Rosenblatt |
| 2006/0004364 A1 | 1/2006 | Green et al. |
| 2006/0030884 A1 | 2/2006 | Yeung et al. |
| 2006/0190042 A1 | 8/2006 | Stone et al. |
| 2006/0235413 A1 | 10/2006 | Denham et al. |
| 2006/0247644 A1 | 11/2006 | Bhatnagar et al. |
| 2006/0282088 A1 | 12/2006 | Ryan |
| 2006/0287661 A1 | 12/2006 | Bolduc et al. |
| 2007/0073320 A1 | 3/2007 | Mikkaichi et al. |
| 2007/0112425 A1 | 5/2007 | Schaller et al. |
| 2007/0142837 A1 | 6/2007 | Dreyfuss |
| 2007/0154515 A1* | 7/2007 | Johnson et al. ............... 424/423 |
| 2007/0185530 A1 | 8/2007 | Chin-Chen et al. |
| 2007/0203511 A1 | 8/2007 | Vardi |
| 2008/0051837 A1 | 2/2008 | To et al. |
| 2008/0132948 A1 | 6/2008 | Surti et al. |
| 2008/0161850 A1 | 7/2008 | Weisenburgh et al. |
| 2008/0228193 A1 | 9/2008 | Matityahu |
| 2008/0300547 A1 | 12/2008 | Bakos |
| 2008/0300629 A1 | 12/2008 | Surti |
| 2009/0005800 A1 | 1/2009 | Franer et al. |
| 2009/0012560 A1 | 1/2009 | Hunter et al. |
| 2009/0024163 A1 | 1/2009 | Zeiner et al. |
| 2009/0082790 A1 | 3/2009 | Shad et al. |
| 2009/0198107 A1 | 8/2009 | Park et al. |
| 2009/0216264 A1 | 8/2009 | Friedman et al. |
| 2009/0228040 A1 | 9/2009 | Mas et al. |
| 2009/0236401 A1 | 9/2009 | Cole et al. |
| 2009/0240264 A1 | 9/2009 | Tuval et al. |
| 2009/0248067 A1 | 10/2009 | Maiorino |
| 2009/0275960 A1 | 11/2009 | Provenza et al. |
| 2009/0287304 A1 | 11/2009 | Dahlgren et al. |
| 2010/0010457 A1 | 1/2010 | Ewers et al. |
| 2010/0016885 A1 | 1/2010 | Eidenschink et al. |
| 2010/0049213 A1 | 2/2010 | Serina et al. |
| 2010/0049289 A1 | 2/2010 | Lund et al. |
| 2010/0087854 A1 | 4/2010 | Stopek et al. |
| 2010/0094341 A1 | 4/2010 | Raju |
| 2011/0028995 A1 | 2/2011 | Miraki et al. |
| 2011/0054539 A1 | 3/2011 | Knopfle et al. |
| 2011/0178534 A1 | 7/2011 | Whitman et al. |
| 2011/0178537 A1 | 7/2011 | Whitman |
| 2011/0190811 A1 | 8/2011 | Shanley |
| 2012/0022586 A1 | 1/2012 | Whitman et al. |
| 2012/0059395 A1 | 3/2012 | Kehdy et al. |
| 2012/0116418 A1 | 5/2012 | Belson et al. |
| 2012/0245634 A1 | 9/2012 | Kaplan |
| 2013/0211426 A1 | 8/2013 | Whitman et al. |
| 2013/0211450 A1 | 8/2013 | Whitman |

FOREIGN PATENT DOCUMENTS

| | | |
|---|---|---|
| WO | 93/14705 | 8/1993 |
| WO | 01/85035 | 11/2001 |
| WO | 03/059173 | 7/2003 |
| WO | 2005/004727 | 1/2005 |
| WO | 2005/058239 | 6/2005 |
| WO | 2007/098212 | 8/2007 |
| WO | 2008/067384 | 6/2008 |
| WO | 2008/116203 | 9/2008 |

OTHER PUBLICATIONS

International Search Report and Written Opinion, dated Apr. 8, 2011, issued in corresponding International Application No. PCT/US2011/021952.

International Search Report and Written Opinion, dated Jun. 1, 2011, issued in corresponding International Application No. PCT/US2011/021949.

(56) References Cited

OTHER PUBLICATIONS

International Search Report and Written Opinion, dated Mar. 23, 2011, issued in corresponding International Application No. PCT/US2011/021947.

European Supplementary Search Report, dated Jun. 13, 2013, issued in corresponding European Patent Application No. 11735202.1.

International Search Report and Written Opinion, dated Sep. 8, 2014, issued in corresponding International Application No. PCT/US2014/30868.

* cited by examiner

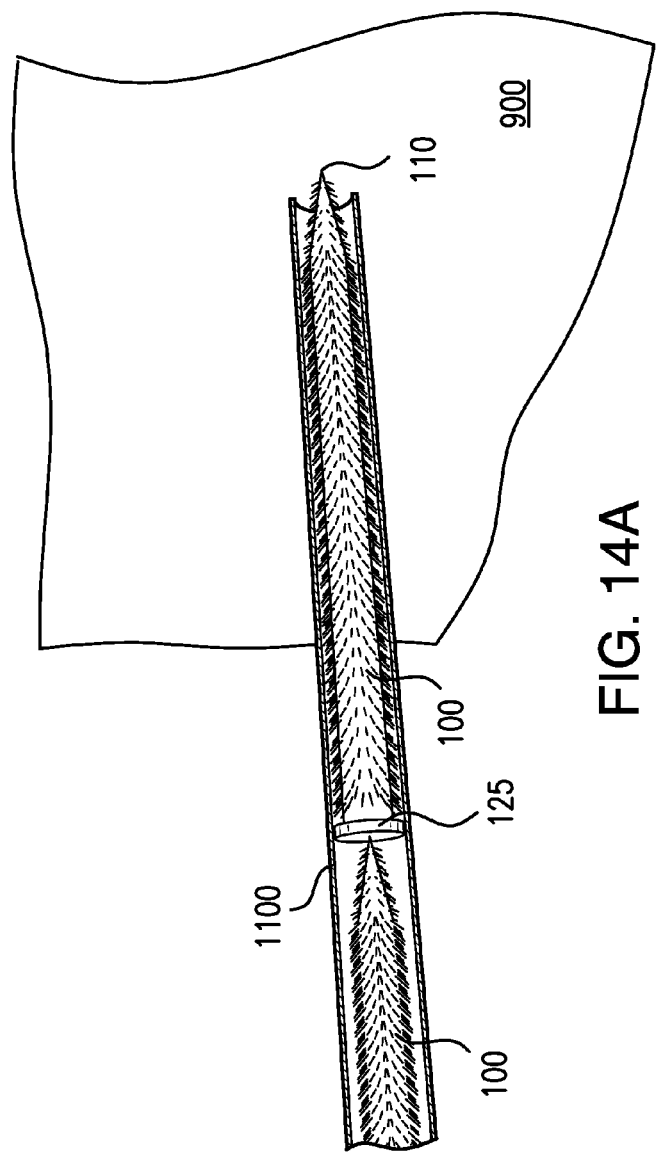

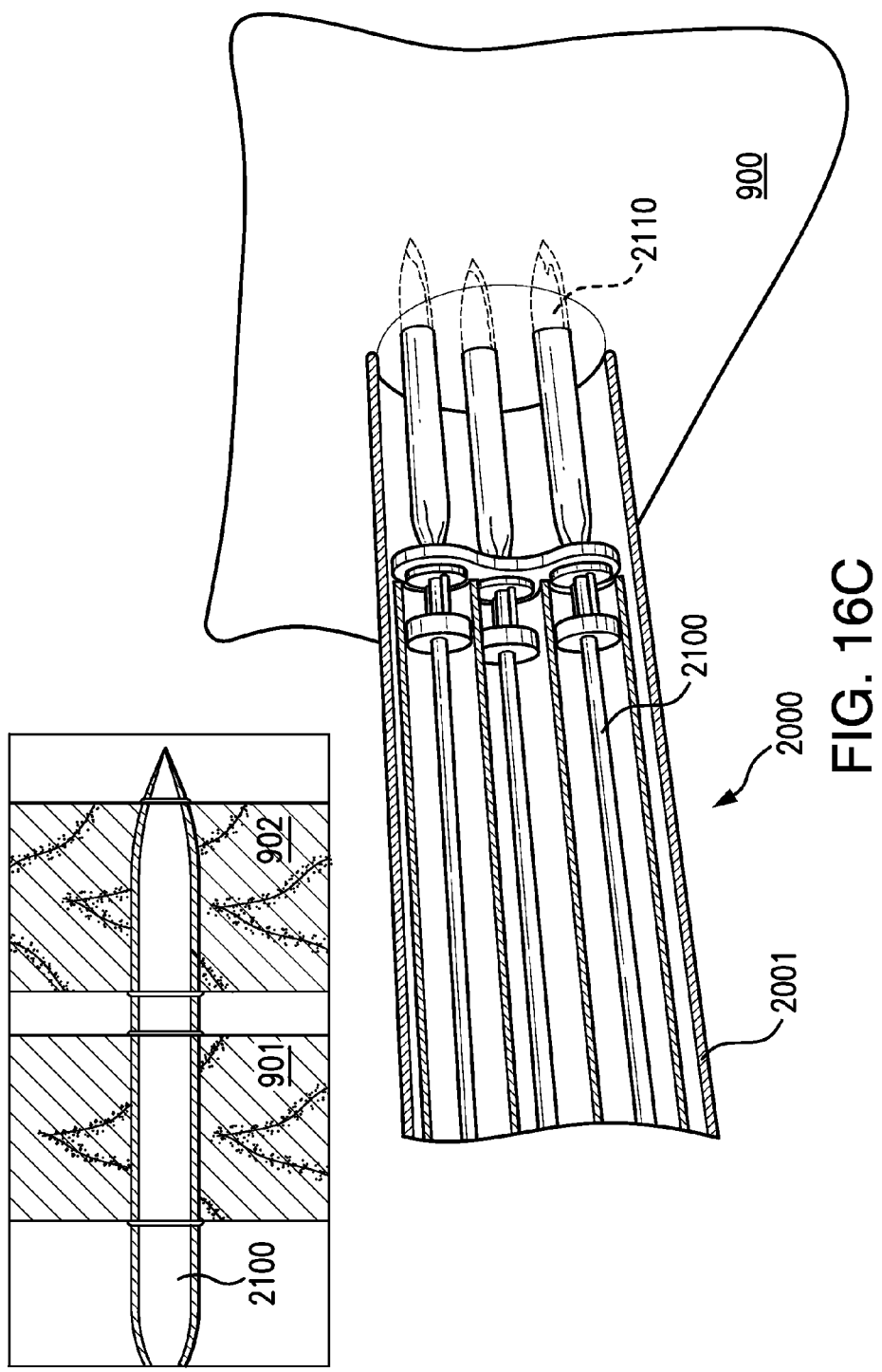

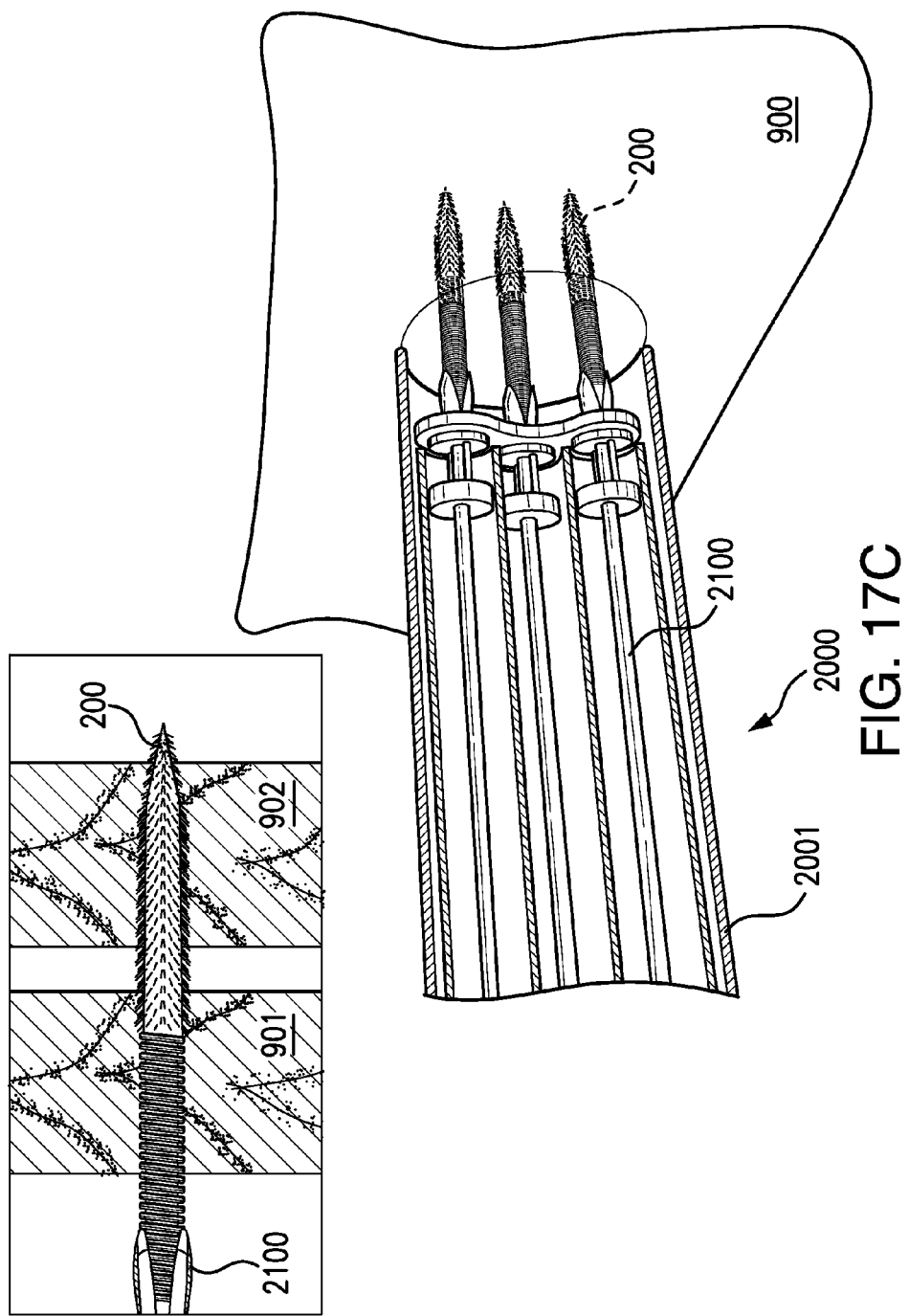

TISSUE REPAIR IMPLANT AND DELIVERY DEVICE AND METHOD

CROSS-REFERENCE TO RELATED APPLICATIONS

This application claims the benefit of U.S. Provisional Patent Application Ser. No. 61/296,868, filed on Jan. 20, 2010, which is expressly incorporated herein in its entirety by reference thereto.

Further, each of the following is hereby incorporated in its entirety by reference thereto: U.S. patent application Ser. No. 13/010,766, filed on Jan. 20, 2011, U.S. patent application Ser. No. 13/010,777, filed on Jan. 20, 2011; and U.S. patent application Ser. No. 13/010,769, filed on Jan. 20, 2011.

FIELD OF THE INVENTION

The present invention relates to a tissue repair implant and delivery device and method.

BACKGROUND INFORMATION

Some surgical interventions require the repair of tissue, e.g., closure of the tissue or graft fixation. These procedures may include, for example, treatment of atrial septal defects (ASD), patent foramen ovale (PFO), left atrial appendage closure, stent graft fixation, and hernia repair, among others.

ASDs and PFOs are considered to be two of the leading contributors to embolic stroke. Stroke is the third leading cause of death in the United States and one of the leading causes of adult disability. It is estimated that 80% of strokes are preventable and that repair of existing ASDs and PFOs will reduce the incidence. When ASDs and PFOs are present in the heart, a debilitating condition may occur. Deoxygenated blood may pass from the right atrium through either the ASD and/or PFO into the oxygenated blood of the left atrium. It has been estimated that approximately one in four individuals in the general population have a PFO. Individuals who have unknown causes of stroke (cryptogenic stroke), have a 40 percent increase in the likelihood of a PFO being present. PFO is even more prevalent in individuals who have had strokes under that age of 55.

U.S. Pat. No. 7,220,265 describes a device for closure of PFO, wherein a catheter is directed into proximity of the PFO. The catheter is inserted between the septum primum and the septum secundum into the left atrium. The catheter then deploys a first closure member, e.g., a "grappling hook element," in the left atrium. The catheter is then drawn back into the right atrium where a second closure member, e.g., a second grappling hook element, is deployed. The first and second closure members are connected by a central connecting member such that the septal tissues are compressed together between the two opposed closure members. U.S. Pat. No. 7,220,265 also discloses a method of closing the PFO using sutures, whereby implantable anchors purportedly limit the need for a continuous thread. The devices and methods of U.S. Pat. No. 7,220,265 require maneuvering of a medical device, e.g., a catheter or suture needle, in both the right and left atria. This may present substantial complexity and difficulty to the procedure, possibly increasing the likelihood of surgeon error and/or increasing the time required to complete the procedure.

Further, typical existing anchors are configured to joining soft tissue to hard tissue, since there is no way to take out the slack with soft tissue to soft tissue joining.

Thus, there is a need for a closure mechanism and method that is simple to operate and only requires access to one side of the tissue or tissues. Further, there is a need for a reliable closure that may be precisely located.

Moreover, some tissue defects, e.g., some heart defects and inguinal hernias, require the implantation of a mesh. In the example of an inguinal hernia, the mesh is intended to create a barrier against abdominal cavity contents protruding through a defect the abdominal peritoneum and inguinal canal. A known treatment for such hernias involves applying a single anchor to a mesh, e.g., a square mesh, then pulling the mesh taut and applying a second anchor to the mesh. This sequential fastening and tightening is repeated until the mesh is secured over the defect. This method is procedurally costly and time consuming, however, and there is a risk that the mesh may not be properly or sufficiently tautened, which could render the mesh ineffective in preventing the protrusion of the abdominal cavity contents through the inguinal canal.

Thus, there is also need for an implanting mechanism and method that allows for a quick and reliable securement of a mesh to repair a tissue defect, e.g., allowing for simultaneous application of fasteners.

Further, there is a need for a mechanism and method that reduces procedural costs and allows access to difficult-to-reach locations of the anatomy.

SUMMARY

According to example embodiments of the present invention, a medical device includes a temporary frame configured to carry an implant, the temporary frame being selectably movable between a retracted position and a deployed position, the implant being in a relaxed state when carried by the frame in the retracted position, the implant being in a taut state when carried by the frame in the deployed position.

The implant may comprise at least one of a mesh, a graft, and a film.

According to example embodiments of the present invention, an implant delivery device comprises es a device body, an implant, and a frame carrying the implant and extending within the device body, the frame being selectably movable between a refracted position in which the frame is collapsed and an extended position in which the frame is expanded.

The implant may be a mesh. The implant may a graft. The implant may be a film.

The device may further comprise a fastener driver configured to fasten the implant to a patient's tissue when the frame is in the extended position.

The frame may be configured to detach from the implant when moving from the extended position to the retracted position after the implant has been fastened to the tissue.

The device body may include a tubular portion that includes a distal opening.

The tubular portion may be a catheter.

The frame may move distally through the distal opening of the tubular portion when the frame moves from the retracted position to the extended position.

The device may further comprise a plurality of fastener drivers extending through the tubular portion, each of the plurality of drivers having a retracted position and an extended position.

When the fastener drivers are in their extended positions, the frame may slidable along the plurality of fastener drivers when the frame moves from the retracted position to the extended position.

A distal portion of each fastener driver may include a curved seat configured to receive and hold the frame when the frame is in the extended position.

Each fastener driver may have a distal opening through which the fastener driver is configured to drive a fastener.

The curved seat of each fastener driver may hold the frame at a position that allows a fastener to be driven through the distal opening of the fastener driver into the implant supported by the frame.

The fastener drivers may be configured to simultaneously drive respective fasteners into the implant while the implant is held tautly by the frame.

A distal end of each fastener driver may be disposed adjacent a longitudinal axis of the tubular portion when the fastener driver is in the retracted position and the distal end of each fastener driver extends radially outwardly from the longitudinal axis of the tubular portion when the fastener driver is moved distally to the extended position.

The frame may be comprised of a shape memory alloy. The frame may be comprised of nitinol. The frame is comprised of spring steel.

According to example embodiments of the present invention, an implant delivery device comprises a device body, a plurality of fastener drivers extending from a distal end of the device body, an implant, and a frame configured to carry the implant, the frame being extendible through the device body and slidably guided along the plurality of fastener drivers between a refracted position in which the frame is collapsed and a deployed position in which the frame is expanded, the implant being relaxed when the frame is collapsed, the implant being taut when the frame is in the deployed position.

The implant may be a mesh. The implant may be a graft. The implant is a film.

The fastener drivers are configured to drive fasteners into the implant when the frame is in the desired deployed position, thereby fastening the implant to an underlying tissue.

According to example embodiments of the present invention, a method comprises deploying a temporary frame to tautly support an implant, positioning the implant in a predetermined location with respect to a tissue, and fastening the implant to the tissue in the predetermined location while the implant is tautly supported by the temporary frame.

The implant may comprise at least one of a mesh, a graft, and a film.

The method may further comprise retracting the temporary frame after the implant has been fastened.

The frame may be comprised of a shape-memory material. The shape-memory material may be nitinol.

The fastening may include simultaneously driving a plurality of fasteners into the implant.

The plurality of fasteners may be simultaneously driven along a periphery of the implant.

According to example embodiments of the present invention, a method comprises supporting an implant with a temporary frame, positioning temporary frame and the supported implant at a location with respect to a tissue, and securing the implant to the tissue by inserting a plurality of anchors through the implant and into the tissue such that the fasteners do not interfere with removal of the frame.

The method may further comprise removing the temporary frame after the fasteners have been inserted.

The implant may be a mesh.

According to example embodiments of the present invention, a surgical implant-positioning device, comprises a hollow needle having an inner chamber, and a sharp tip configured to pierce tissue, a surgical implant positionable within the inner chamber of the needle, and an actuator configured to drive the needle with the surgical implant into a predetermined position in the tissue, wherein the needle is retractable from the driven position to leave the surgical implant seated in the tissue.

The needle may include one or more slits that allow a distal end of the needle to expand to allow the implant to pass through the distal end as the needle is retracted.

The implant may have a distal portion with filaments configured to resist distal movement of the implant.

The implant may have a proximal portion with external threads.

The device may further comprise a proximal head having internal threads, and a head driver configured to mate the proximal head to the proximal portion of the implant and rotate the proximal head with respect to the proximal portion such that engagement between the internal threads and the external threads causes movement of the proximal head along a longitudinal axis of the implant.

The device may further comprise a proximal head, and a head driver configured to mate the proximal head to a proximal portion of the implant and drive the mated proximal head along a longitudinal axis of the implant.

The proximal head may be configured to maintain its axial position after a disengagement of the head driver from the proximal head.

The device may further comprise a tubular housing, the needle extending through the tubular housing.

The tubular housing may be a catheter.

The needle may be one of a plurality of needles extending through the tubular housing, and the implant is one of a corresponding plurality of implants positionable within the needles.

The device may further comprise an implantable plate, the plurality of needles extending through the plate.

The device may further comprise a plurality of proximal heads corresponding to the plurality of needles, and a head driver configured to mate each of the proximal heads to a proximal portion of the respective implant and drive the mated proximal head distally along a longitudinal axis of the respective implant.

The driving of proximal heads may cause distal movement of the plate with respect to the implants.

The device may further comprise a plunger extending along the needle, the plunger configured to prevent the implant from retracting with the needle when the needle is retracted.

The needle may be comprised of a shape memory material. The shape memory material may be nitinol. The shape memory material may be spring steel.

According to example embodiments of the present invention, a catheter includes a housing having a distal opening. The catheter includes a plurality of fastening arms extending along the housing, the fastening arms movable between a retracted position and a distally extended position in which the fastening arms are radially spaced apart. The fastening arms are configured to drive fasteners through distal openings in the fastening arms. The catheter includes a bendable frame and a mesh coupled to and supportable by the frame. The frame is movable along the extended fastening arms from a retracted position to a distally extended position in which the periphery of the mesh extends radially beyond the distal openings of the fastening arms, thereby allowing fasteners to be driving into the mesh.

The frame may be formed from a shape-memory metal, such as nitinol or spring-loaded steel.

According to example embodiments of the present invention, a framing mechanism is configured to pull a mesh tautly over a tissue defect and to drive a plurality of fasteners or anchors through the mesh and into the tissue.

Two or more, e.g., all, of the anchors may be driven simultaneously, or substantially simultaneously.

The anchors may be driven in a plurality of sets, each set of anchors being driven simultaneously, or substantially simultaneously.

Further features and aspects of example embodiments of the present invention are described in more detail below with reference to the appended Figures.

BRIEF DESCRIPTION OF THE DRAWINGS

FIGS. 14A to 14C illustrate the driving of a fastener into tissue.

FIGS. 16A to 16C sequentially illustrate the insertion of implant-carrying needles or sleeves of an implanting device into tissue.

FIGS. 17A to 17D sequentially illustrate a retraction of the sleeves from the tissue and the implants carried by the sleeves.

DETAILED DESCRIPTION

Figure 1A:
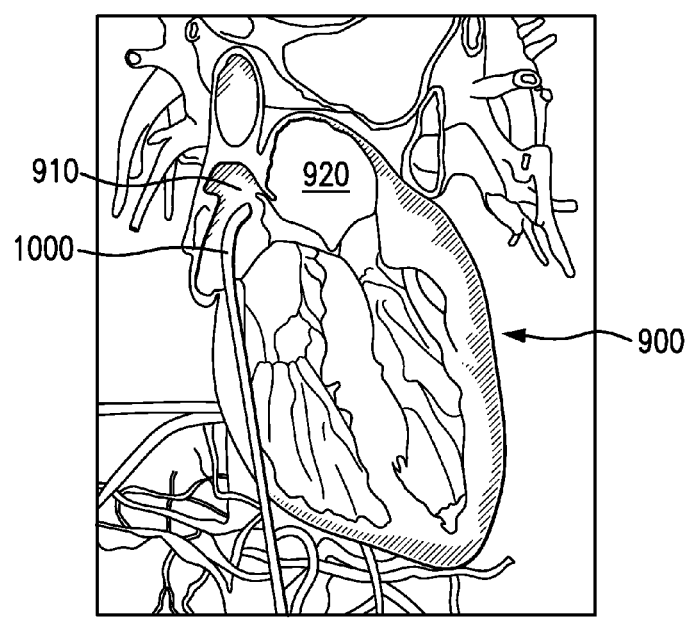
FIGS. 1A to 1C show a catheter when inserted into the right atrium of a human heart.
Figure 1B:
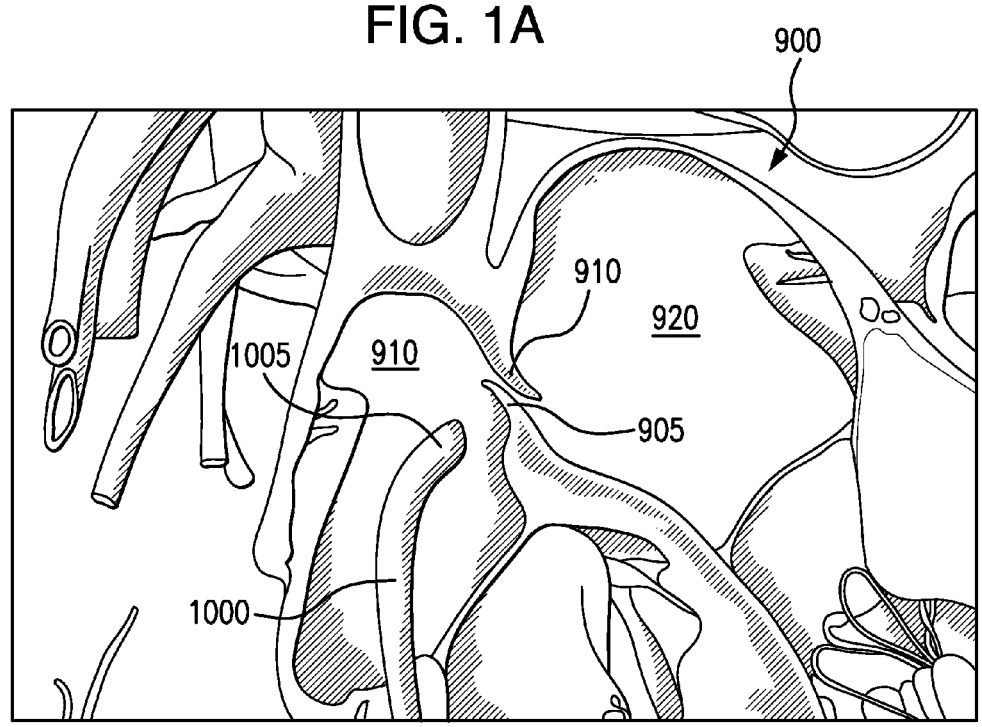
Figure 1C:
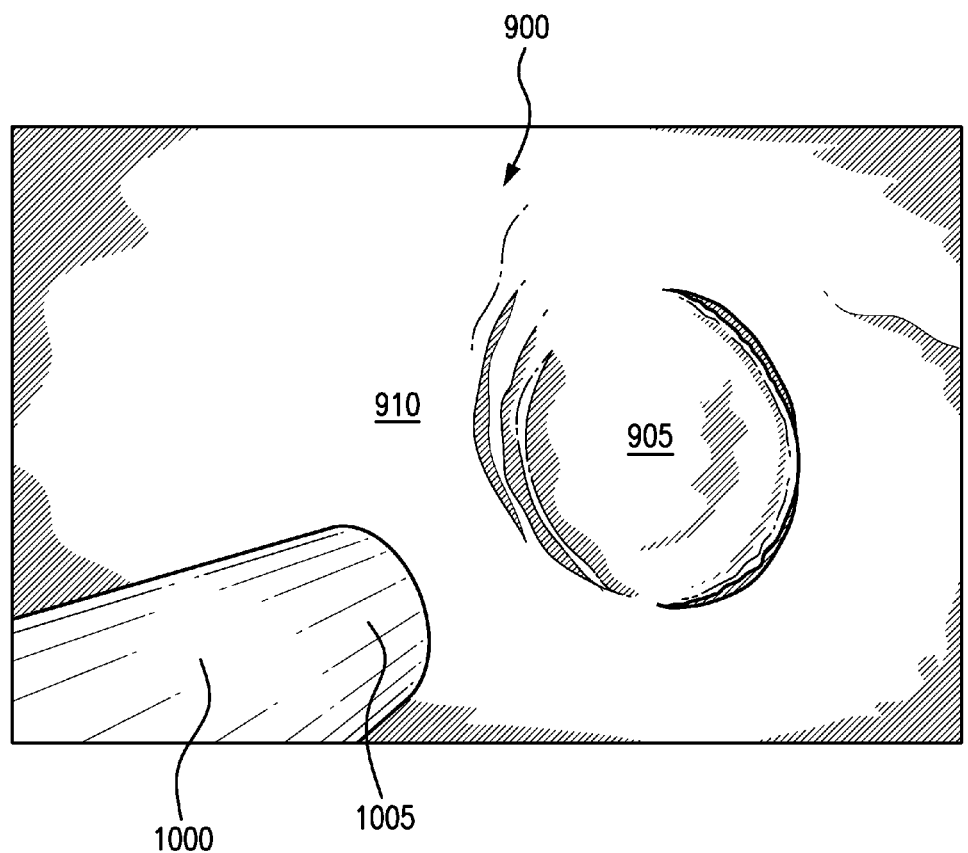

FIGS. 1A to 1C show a catheter 1000 when inserted into the right atrium 910 of a human heart 900. Although the heart 900 is a human heart, it should be understood that any other appropriate organ of a human or other animal, e.g., mammal, may be accessed and operated on by the catheter 1000. The catheter 1000 may be inserted via an incision or puncture in one or more walls of the heart 900, e.g., created by a trocar. The catheter 1000 has a bend or curvature toward its distal end portion 1005 that allows the end portion 1005 to be directed transversely with respect to the direction in which the catheter 1000 enters the wall or walls of the heart 900. In this regard, the catheter 1000 may be steerable, e.g., by one or more cables or guide wires that extend along the length of the catheter 1000. This allows the end portion 1005 to be directed, e.g., substantially perpendicularly with respect to a portion of tissue 905 to be repaired as illustrated in FIGS. 1A to 1C. The portion of tissue 905 is a flap of tissue of the atrial septum 910 that allows blood to pass through the atrial septum between the left and right atria. Thus, the heart 900 as illustrated, e.g., in FIGS. 1A to 1C has an atrial septal defect (ASD).

Figure 2A:
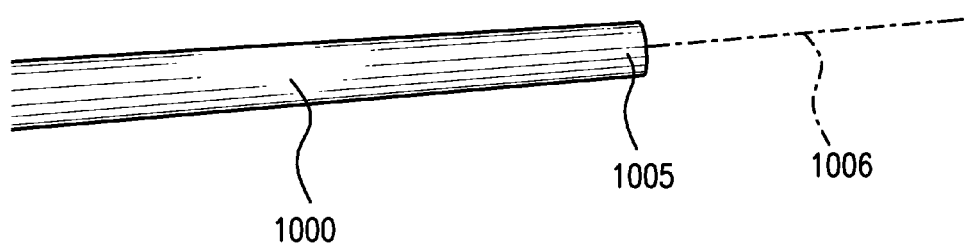
FIGS. 2A to 2C sequentially illustrate the extension of fastening arms from a distal end of the catheter.
Figure 2B:
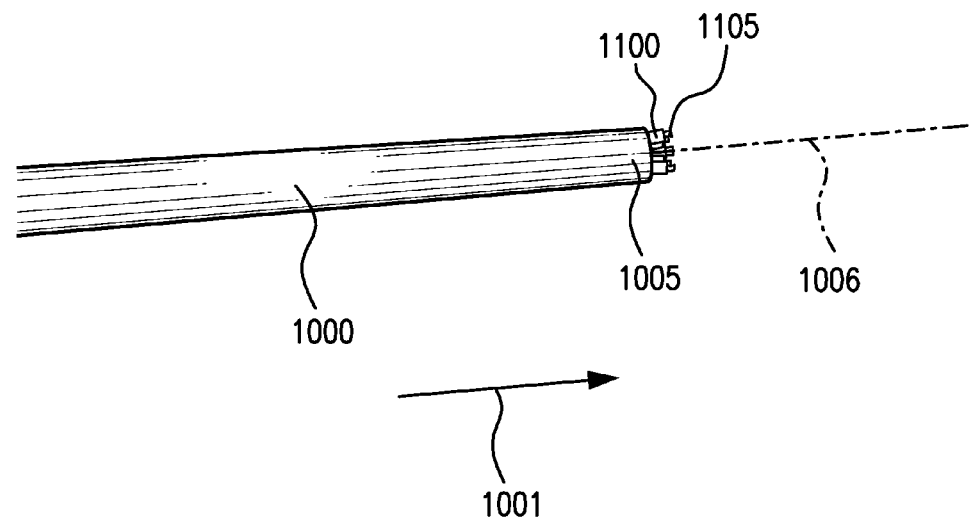
Figure 2C:
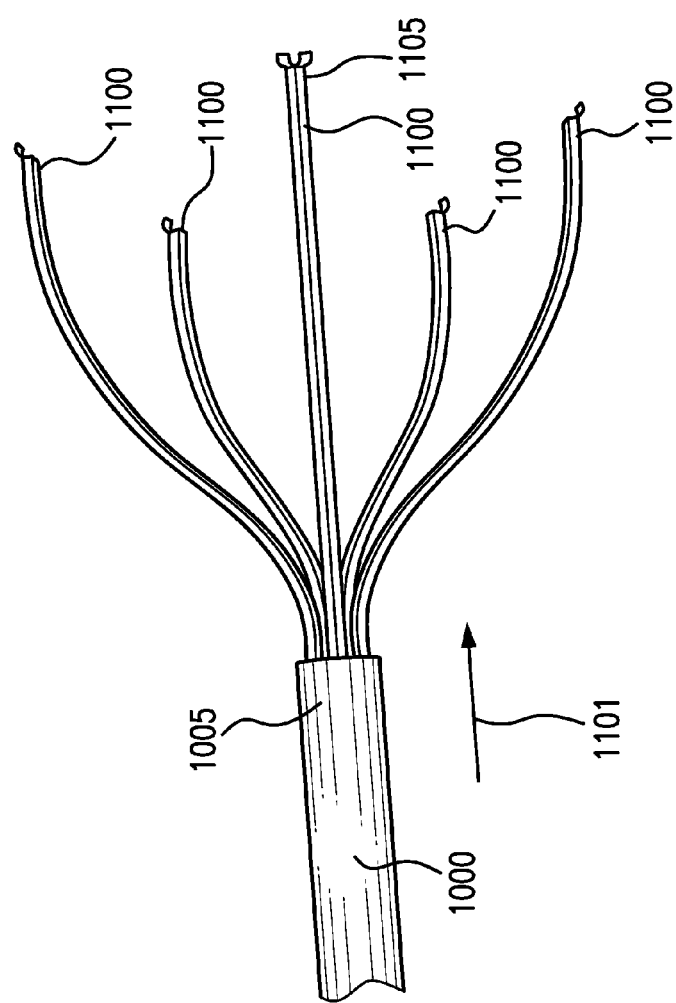

FIGS. 2A to 2C sequentially illustrate the extension of fastening arms or fingers 1100 from a distal end of the catheter 1000. In order to repair the ASD or other defect, the catheter 1000 deploys the plurality of fastening arms 1100 having distal end portions 1105. Although five fastening arms 1100 are illustrated, it should be understood that any number of fastening arms 1100 may be provided. FIG. 2A illustrates the catheter 1000 prior to deployment of the arms 1100. It is generally in this configuration that the catheter 1000 is maneuvered though the body, e.g., within the heart 900. This may be advantageous to prevent the distal end portions 1105 of the fastening arms 1100 from catching or otherwise possibly damaging the patient's tissue during maneuvering.

FIG. 2B illustrates the end portions 1105 of the fastening arms 1100 as they begin to protrude from the distal end of the catheter 1000. In this position, the fastening arms are parallel, or substantially parallel, to the longitudinal extension of the catheter 1000. To protrude from the distal end of the catheter 1000 as illustrated in FIG. 2B, the fastening arms 1100 move with respect to the catheter (which may be, e.g., held in a substantially fixed position) in a distal direction indicated by arrow 1001.

As the fastening or extension arms 1100 continue to move further distally outwardly from the distal end of the catheter 1000, the extension arms begin to curve radially outwardly with respect to the longitudinal axis 1006 of the distal end portion 1005 of the catheter 1000 and then curves back toward a parallel, or near parallel, position with respect to the longitudinal axis 1006 of the distal end portion 1005 of the catheter 1000. Thus, extension arms 1100 have a smooth curvature that, moving distally away from the distal end of the catheter 1000, initially curves radially outwardly, then smoothly and continuously curves back to parallel, or near parallel. In this regard, the fastening arms 1100 have a smooth S-curve shape, where for each of the fastening arms 1100, the "S" profile falls within a respective plane that includes the longitudinal axis 1006 of the end portion 1005 of the catheter 1000.

The fastening arms or tines 1100 are formed of a shape memory alloy, such as, e.g., nitinol or spring-loaded steel. In this regard, the spring force or shape memory urges the extension arms to the relative extended positions illustrated, e.g., in FIG. 2C. Thus, when the fastening arms 1100 are bent into the retracted position in the catheter 1000, they extend substantially along the longitudinal axis of the catheter 1100 (e.g., they are straight or substantially straight, where, for example, the catheter 1100 is straight) and are flexible or malleable to allow for flexibility in the catheter 1000 if desired. Then, as the fastening arms 1100 are distally advanced from the end of the catheter 1000, the fastening arms 1100 are urged to their desired extended positions by the spring or shape-memory force.

The fastening arms 1100 are circumferentially equally spaced apart with respect to the longitudinal axis 1006 of the end portion 1005 of the catheter 1000, i.e., approximately 72 degrees apart (360 degrees divided by five fastening arms 1100). However, it should be appreciated that any appropriate regular or irregular angular spacing around the axis 1006 may be provided. Further, although each of the fastening arms 1100 is spaced and curved identically, or substantially identically, away from the axis 1006, it should be appreciated that curvature and/or spacing of one or more of the fastening arms 1100 may deviate from that of any one or more of the other fastening arms 1100.

The fastening arms or tubes 1100 are hollow to allow, e.g., shafts, implants, fasteners, electronics, sensors, driving mechanisms, etc. to be disposed in the arms 1100. This allows, for example, the firing of fasteners from the arms 1100 as described herein.

Referring to FIG. 2C, the fastening arms 1100 are positioned in a fully extended position where the distal end portions 1105 are all longitudinally directed distally in a parallel or near parallel direction.

Figure 3A:
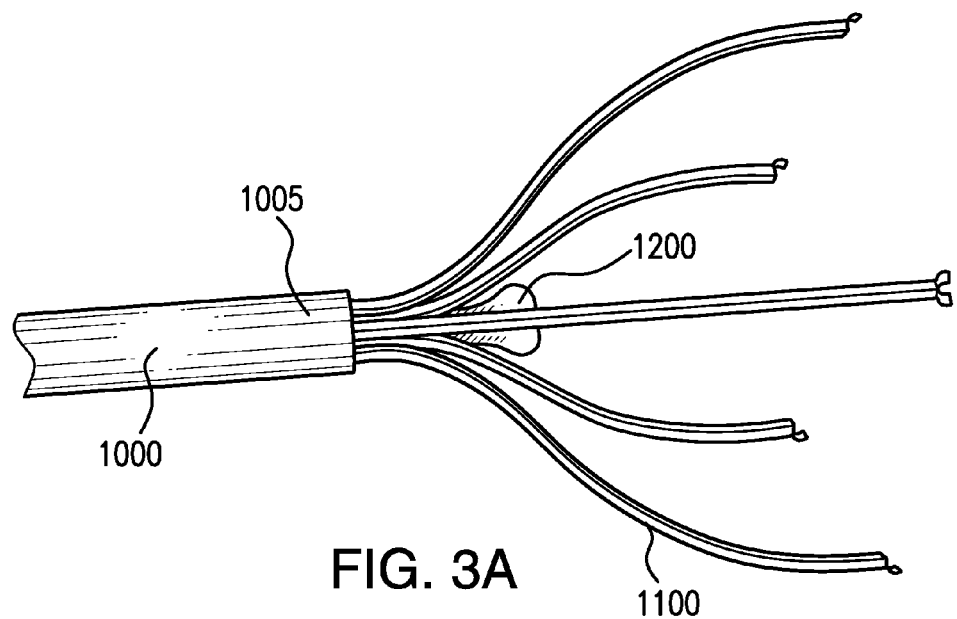
FIGS. 3A to 3F sequentially illustrate the deployment of a frame and mesh from the distal end of the catheter to a distal position toward the ends of the fastening arms.
Figure 3B:
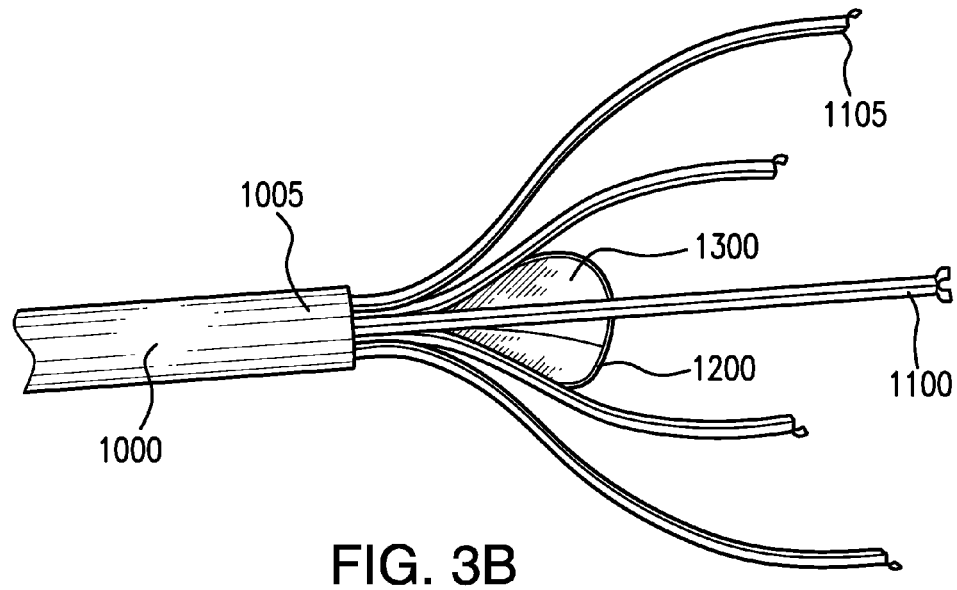

Once the fastening arms 1100 are in the fully extended position illustrated in FIG. 2C, the distal deployment of a temporary graft/frame 1200 formed, e.g, of a shape memory alloy, e.g., nitinol or spring-loaded steel, and a mesh 1300, e.g., a collagen or synthetic mesh, or other non-permeable tissue implant material, is distally deployed as illustrated, e.g., in FIGS. 3A to 3F, which sequentially illustrate the deployment of the frame 1200 and mesh 1300 from the distal end of the catheter 1000 to a distal position toward the ends of the fastening arms 1100. The mesh 1300 may be, e.g., an ultrathin bovine pericardium or synthetic graft. The frame 1200 includes a loop portion 1210 that is essentially flattened (i.e., the area encircled by the loop portion 1210 is minimal) when the frame 1200 is disposed in the interior portion of the tube or catheter 1000. As illustrated in FIGS. 3A and 3B, as the frame 1200 begins to distally extend beyond the distal end of the catheter 1000, the loop portion 1210 begins to open and expand into a more round shape, with the mesh 1200 being releasably fastened along the extension of the loop portion 1210.

Figure 3C:
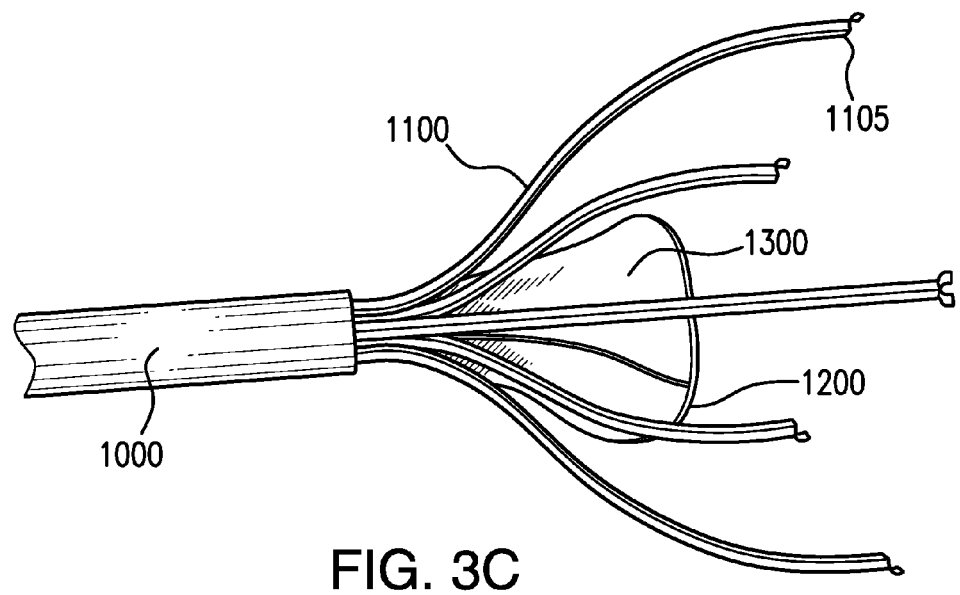
Figure 3D:
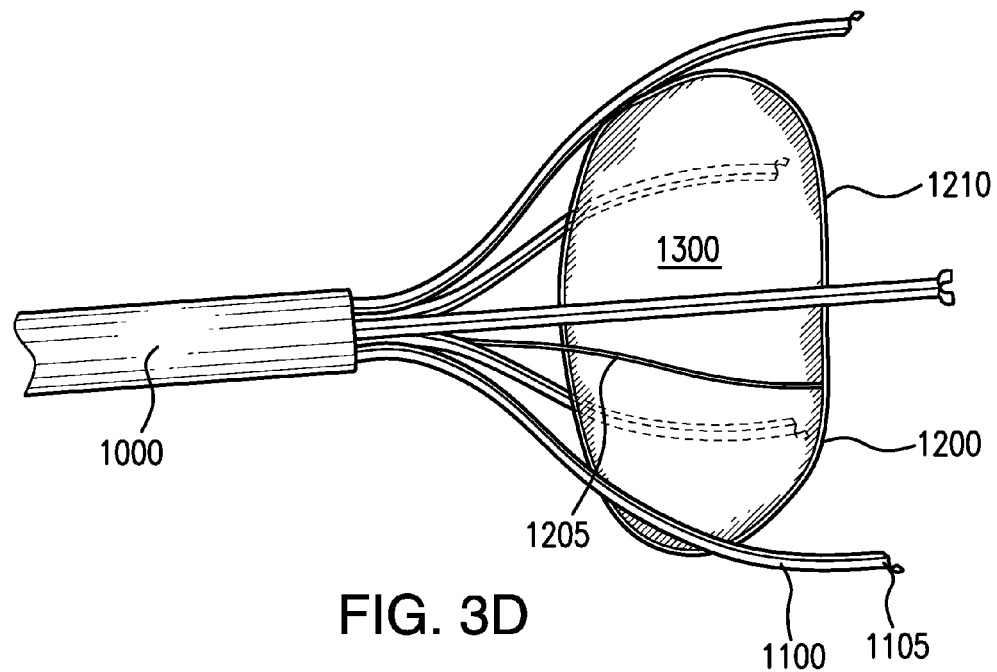

FIGS. 3C and 3D show the mesh 1300 and loop portion 1210 as they continue to move distally and continue to radially expand outwardly. As illustrated, e.g., in FIGS. 3D and 3E, the radially outward expansion of the shape memory loop portion 1210 urges the loop portion 1210 distally due to contact with and sliding along the curvature of the fastening arms 1100. As the loop portion 1210 moves distally, an extension 1205 of the frame 1200, which is continuously formed with the loop portion 1210 may be gradually fed outwardly. This distal feeding may help urge the frame distally outwardly. The shape-memory loop portion 1210 of the frame 1200 may be urged to its open or radially outward position by any appropriate shape memory mechanism, e.g., spring force, heat and/or application of an electric current.

Figure 3E:
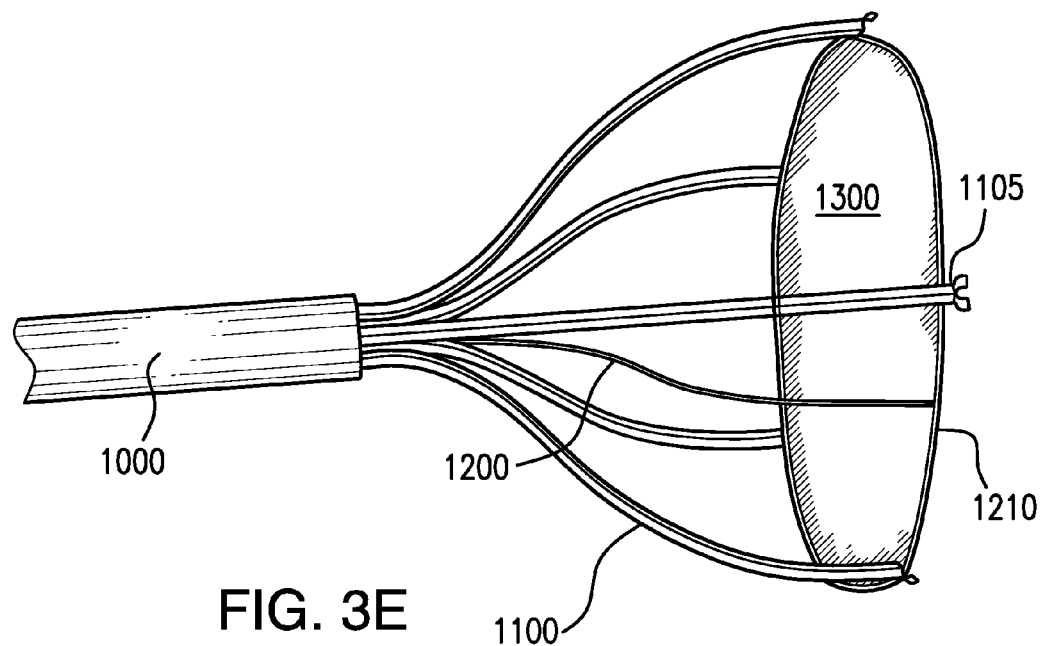

FIG. 3E shows the loop portion 1210 as it approaches the distal ends of the fastening arms 1100. In the position shown in FIG. 3E, the loop portion 1210, which is being, in a spring-like fashion, urged (via its shape memory mechanism) toward a fully radially extended position, exerts a radially outward force on the fastening arms 1100, which are radially constraining the further expansion of the loop portion 1210. In this position, the loop portion 1210 has an irregular curvature or waviness along its circumferential perimeter, as illustrated in FIG. 3E.

Figure 3F:
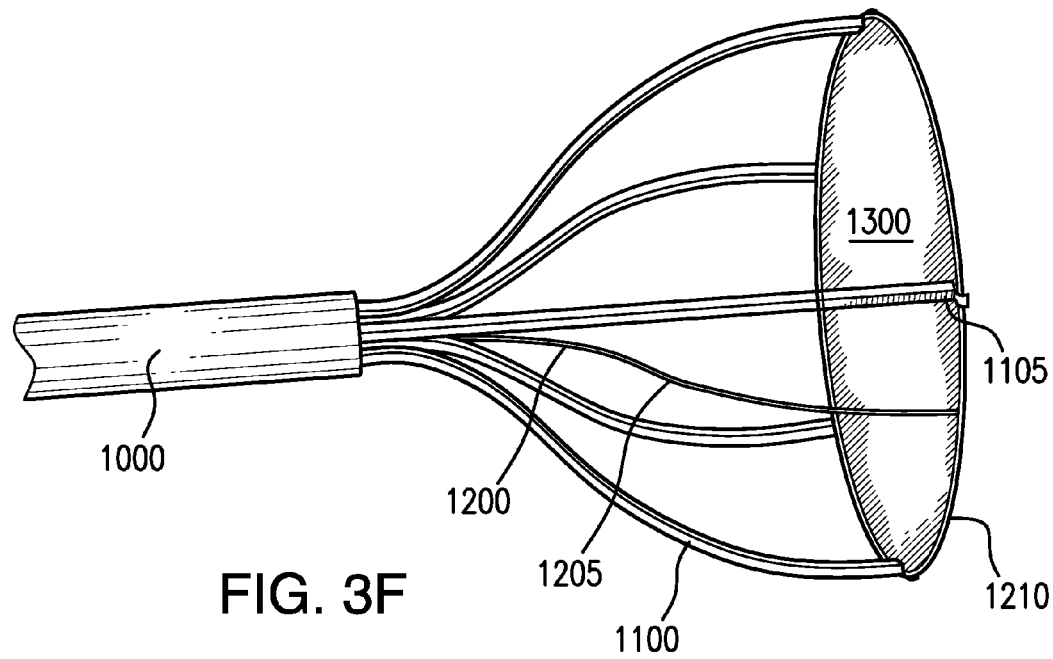
Figure 4A:
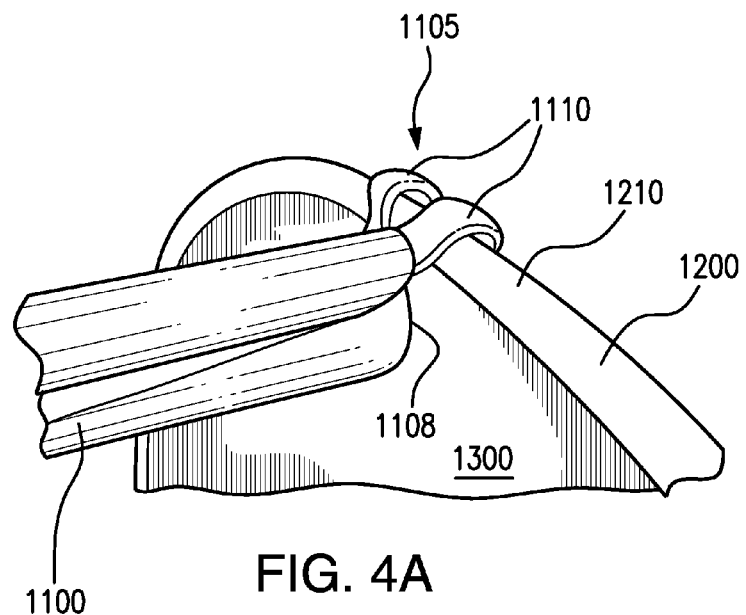
FIGS. 4A and 4B shows the frame seated at a distal end portion of one of the fastening arms.
Figure 4B:
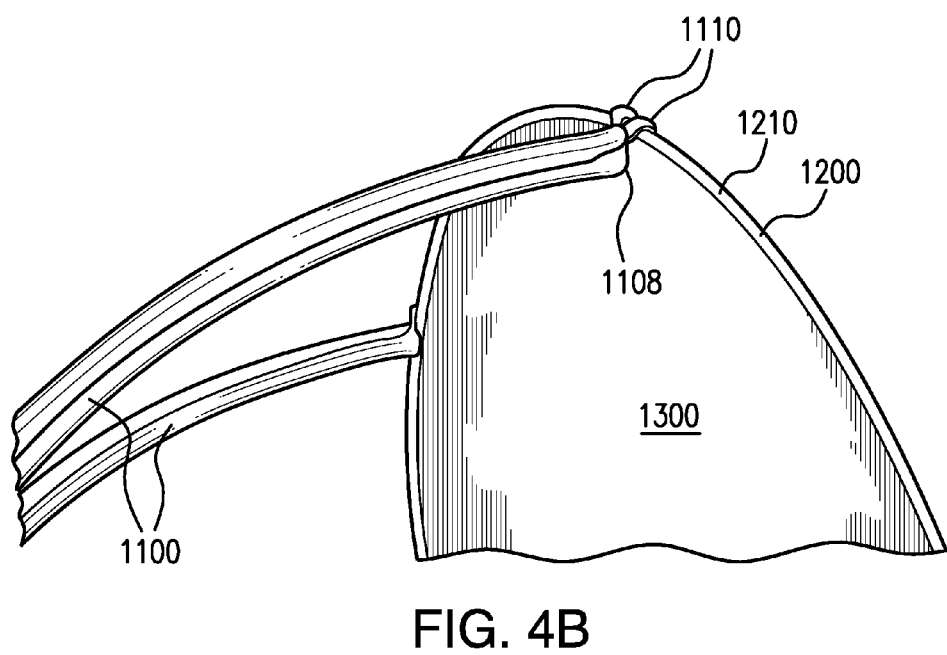

Further distal extension of the frame 1200 results in the loop portion 1210 of the frame 1200 passing distally beyond an end lip or edge 1108 of each fastening arm 1100, which allows the loop portion 1210 to spring or extend radially outwardly to engage curved retaining fingers 1110 at the distal ends of each fastening member, as illustrated in FIGS. 3F, 4A and 4B. This is the outward-most position for the loop portion 1210. In this position, the curved fingers 1110 extend partially around the wire circumference of the loop portion 1210 to restrain the loop portion 1210 in a secured position in the curved fingers 1110. Although each fastening member 1210 includes two curved fingers 1110, any number of curved fingers 1110, including a single curved finger 1110 may be provided. Further, it should be appreciated that, according to some example embodiments, less than all of the fastening arms 1100 are provided with fingers 1110.

When the loop portion 1210 of the frame 1200 is in the outward-most position illustrated, e.g., in FIGS. 3F, 4A, and 4B, the mesh 1300 is pulled radially by the loop portion 1210 to which it is attached, thereby pulling the mesh 1300 into an expanded or taut position. In the fully expanded position, the mesh 1300 is taut and planar, or substantially planar since the particular portion of tissue 900 to be repaired is planar. However, where the surface profile of the tissue is non-planar or irregular, the distal ends of the fastening arms 1100 may be positioned to match the mesh 1300 to the irregular topography or surface of the tissue, e.g., while still maintaining tautness in the mesh 1300. This may be accomplished, e.g., by computer control using, e.g., pressure feedback for each fastening arm 1110 and/or video/image data or other topographical tissue data.

It is noted that the relative geometries of the fastening arms 1100 and the ring or loop portion 1210 should be selected to ensure that the loop portion 1210 is able to expand and meet the respective fingers 1110 at the distal ends of the fastening arms 1110. Otherwise, the loop portion 1210 may not seat properly in the fingers 1110. Moreover, it should be understood that the geometry of the loop portion 1210 and mesh 1300 may be any appropriate shape, e.g, oval, polygonal, or other irregular shape, as may be desirable for varying applications. As indicated above, however, the shape of the loop portion 1210 and the geometric positioning of the fastening arms 1100 should be matched to the extent that the loop portion 1210 properly seats in the fingers 1110 at the distal ends of the fastening arms 1100.

As illustrated, e.g., in FIGS. 4A and 4B, the frame 1200 is securely seated in two of the curved fingers 1110 at a distal end portion 1105 of one of the fastening arms 1100. In this regard, the curvature of the wire of the loop portion 1210 may closely match, or be the same as, the curvature of the portion of the curved fingers 1110 that contacts the loop portion 1210. It should be understood, however, that any appropriate geometry may be provided to constrain the loop portion 1210. The geometry of the fingers 1110 should, however, exert some proximally directed force onto the loop portion 1210 to prevent or resist the loop portion 1210 from distally separating from the distal ends of the fastening arms 1100.

Further, when the loop portion 1210 of the frame 1200 is in the outward-most, or fully extended position, the extension 1205 of the frame 1200 extends and is continuous from the loop portion 1210 into the interior of the catheter. The extension 1205 may extend any appropriate length within the catheter 1000, e.g., the entire length of the catheter to a mechanism configured to distally advance the frame 1200 and/or actuate the shape-memory behavior of the frame 1200.

FIGS. 5A to 5F sequentially illustrate the placement and fastening of the mesh 1300 over a hole 930 in the heart 900 and the retraction of the catheter 1000. The hole 930 may represent the opening of the ASD described above, or an opening of, e.g., a patent foramen ovale (PFO) or an inguinal hernia. Moreover, the hole 930 may be any appropriate portion of any organ that may require the application of a mesh. For example, a portion of tissue may be weakened but not have a through hole, the application of the mesh serving to strengthen the weakened area.

The mesh 1300 may be any appropriate material, e.g, biocompatible material such as collagen or synthetic material. For example, the mesh 1300 material may be selected to be bio-absorbable, such that over time (e.g., after the patient's tissue has grown over the mesh 1300) the mesh is entirely absorbed into the patient's body. For example, the mesh may be formed of polyglycolic acid (PGA), or a PGA copolymer. The mesh 1300 may also, or alternatively, be formed of copolymers of polyester and/or nylon and/or other polymer(s).

Figure 5A:
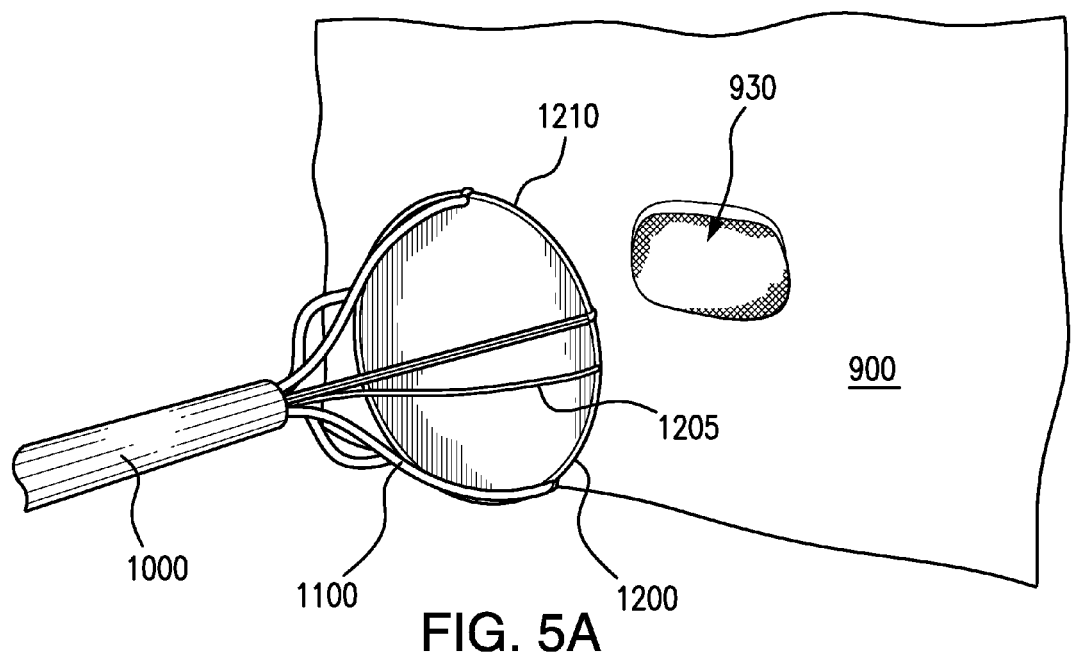
FIGS. 5A to 5F sequentially illustrate the placement and fastening of the mesh over a hole in a tissue and the retraction of the catheter.
Figure 5B:
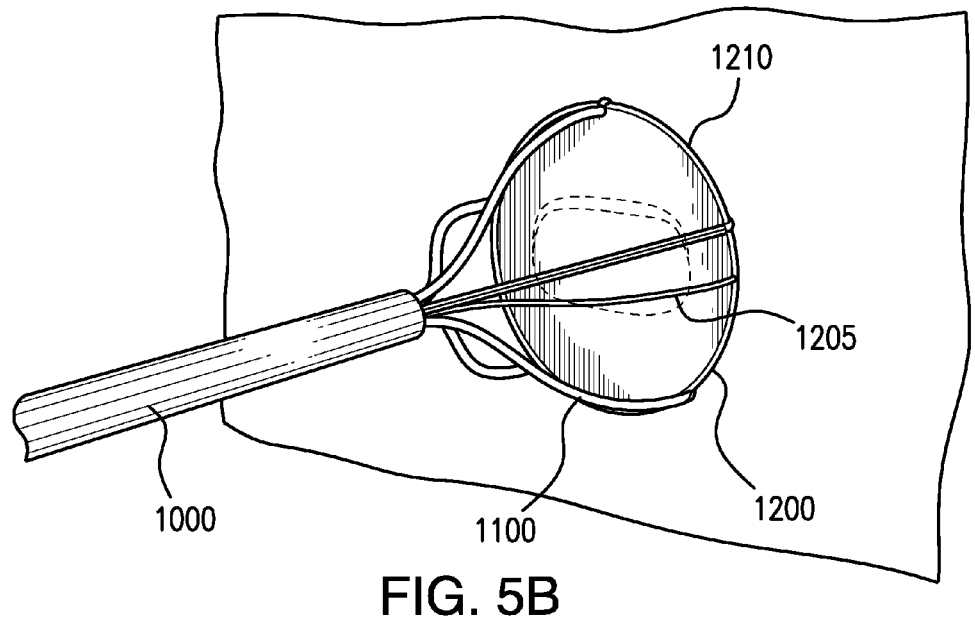

As sequentially illustrated between FIGS. 5A and 5B, the catheter, along with the fastening arms 1100, the frame 1200, and the mesh 1300 is moved and positioned such that the mesh 1300 completely overlies the hole 930. In this position, the mesh 1300 is being held by the fastening arms 1100 in a planar and/or taut position over the hole 930 and against the surround tissue of the heart 900, or other tissue. In the position illustrated in FIG. 5B, a first set of fasteners 1400 is simultaneously applied, one each fired from a distal end of a respective fastening arm 1100.

It is noted that the proper seating of the frame 1200 in the fingers 1110 allows the loop portion 1210 of the frame 1200 to be disposed radially beyond the apertures in the fastening arms 1100 through which the fasteners are driven. That is, the retaining fingers 1110 orient the respective distal openings of fastening arms 1100 so that an implant fired or driven through the opening hits the mesh 1300 and not the ring or loop 1210. Thus, it is ensured that the fasteners penetrate the taut mesh 1300 without interference from the wire frame 1200.

Figure 5C:
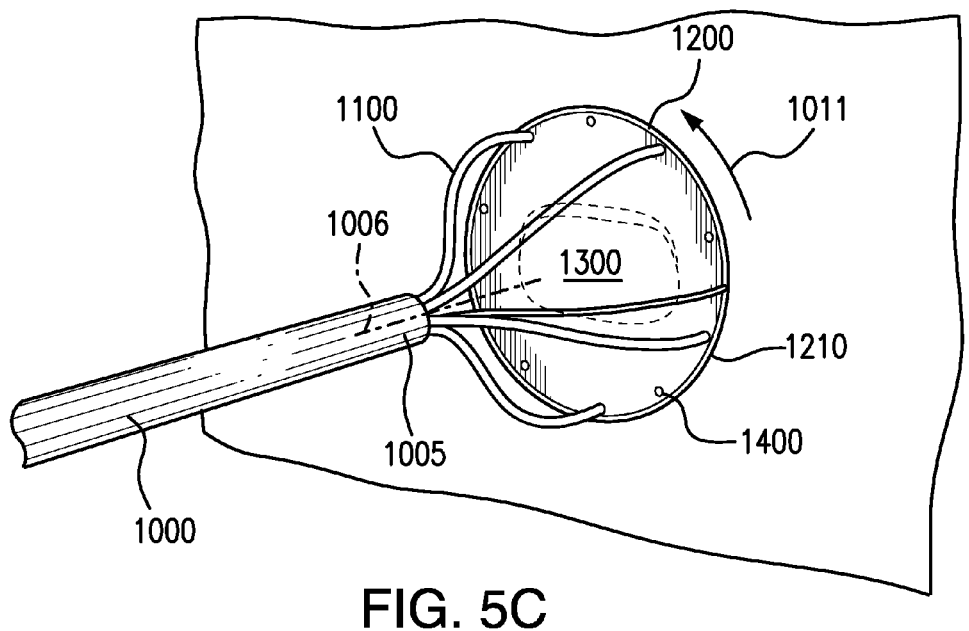

After firing the first set of fasteners 1400, the fastening arms 1100 are rotated about the longitudinal axis 1006 of the distal end 1005 of the catheter 1000 in a direction indicated by arrow 1011 (as illustrated in FIG. 5C) such that each of the fastening arms 1100 is positioned between a respective pair of fasteners 1400 previously applied, and a second set of fasteners 1400 is subsequently simultaneously fired into the tissue. Prior to the application of the second set of fasteners 1400, the fastening arms 1100 are rotated one-half, or substantially one-half, the number of degrees between each adjacent pair of fastening arms (i.e., approximately 36 degrees, which is one half of the approximately 72 degrees between the five fastening arms 1100). However, it should be understood that any amount of rotation may be provided, or if the distal ends of the fastening arms 1100 are sufficiently closely spaced, rotation and subsequent application of a second set of fasteners 1400 may be dispensed with.

The simultaneous firing of the first set of fasteners 1400 and the simultaneous firing of the second set of fasteners 1400 may be beneficial in reducing time and potential for complications, as compared to, e.g., a procedure that involves placing a single fastener into a mesh and sequentially and repeated pulling the mesh taut and driving an additional fastener. It should be understood, however, that the driving mechanisms of example embodiments of the present invention allow the flexibility of sequential firing, and/or any combination or order of firing, e.g., around the perimeter of the mesh 1300.

Although the rotation of the fastening arms 1100 occurs with respect to both catheter 1000 and mesh 1300, it should be understood that the catheter may be configured to rotate along with fastening arms 1100 with respect to the mesh 1300. Further, it should be understood that although the rotation that occurs from the position illustrated in FIG. 5B to the position illustrated in FIG. 5C is counter-clockwise, a clockwise rotation may be provided. Moreover, more than two sets of fasteners 1400 may be applied, e.g., where the number of degrees between the respective positions of the fastening arms is substantially, or approximately, the number of degrees between each adjacent pair of fastening arms 1100 divided by the number of sets of fasteners 1400. In this manner, a plurality of substantially evenly spaced apart fasteners 1400 may be applied in sequentially applied sets.

Figure 5D:
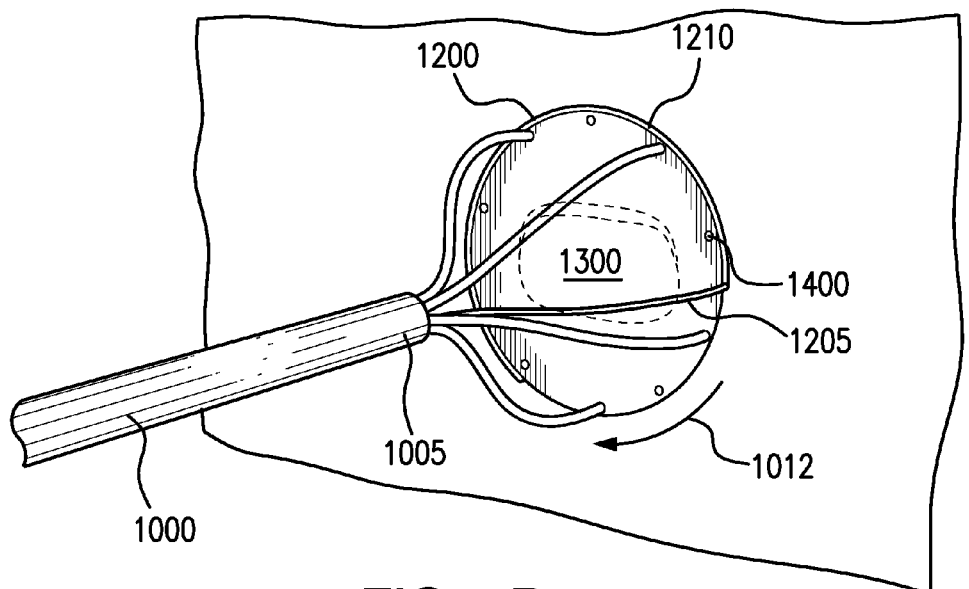
Figure 5E:
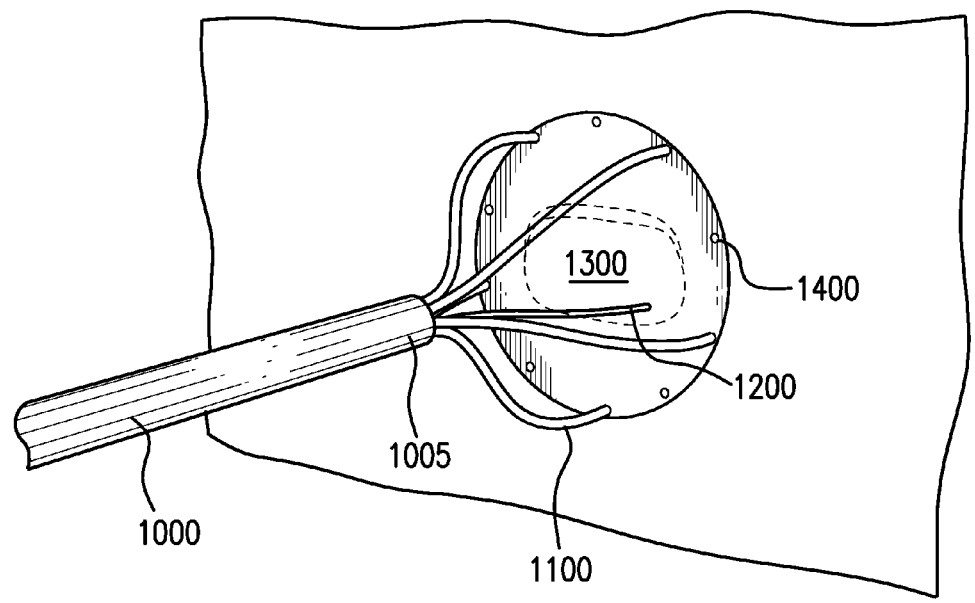

After the mesh 1300 is sufficiently fastened with fasteners 1400, the frame 1200 may be retracted as illustrated sequentially in FIGS. 5D and 5E. As shown, the frame is pulled in a clockwise direction indicated by arrow 1012 along the periphery of the loop portion 1210 and along the extension 1205 until the frame 1200 is completely retracted, e.g., into the catheter 1000. The frame 1200 may be attached to the mesh 1300 via, e.g, a peripheral loop or loops of the mesh 1300, such that the retraction of the frame 1200 causes the frame 1200 to be pulled from the loop or loops, thereby releasing the connection between the frame 1200 and the mesh 1300.

Figure 5F:
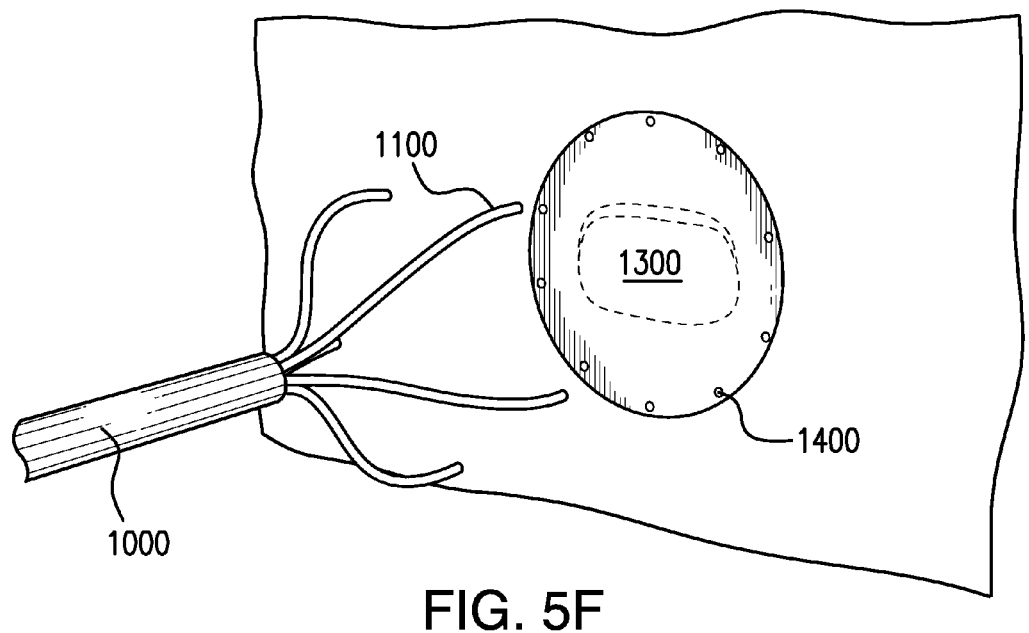

Once the frame 1200 is fully retracted and disengaged from the mesh 1300, the catheter 1000 and the fastening arms 1100 may be pulled distally away from the surgical site, as illustrated in FIG. 5F, with the mesh 1300 being retained over the hole 930 via engagement between the fasteners or implants 1400 and the underlying tissue of the heart 900.

Figure 6A:
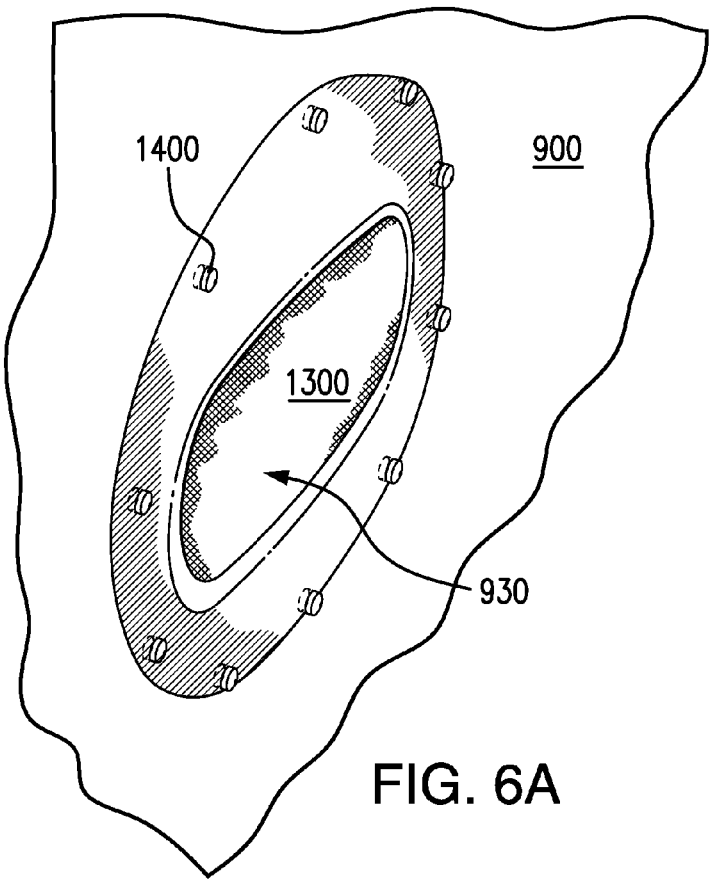
FIGS. 6A and 6B show a back view of the tissue to which the mesh is fastened.
Figure 6B:
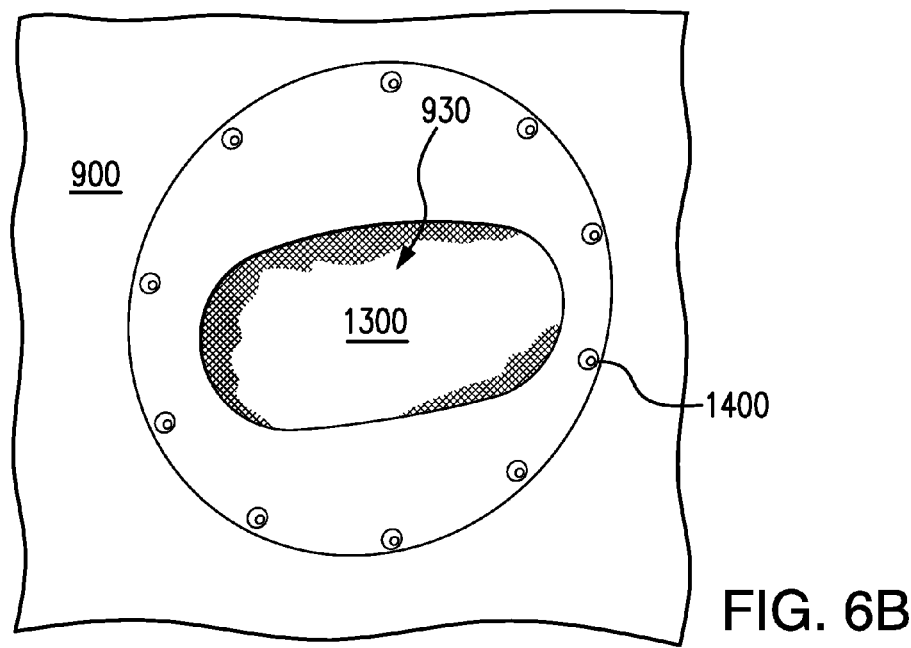

FIGS. 6A and 6B show a back view of the tissue 900 to which the mesh 1300 is fastened via implants or fasteners 1400. As illustrated, the fasteners 1400 have penetrated through the back surface of the tissue 900. It should be understood, however, that completely penetrating the tissue is not necessary, so long as a sufficient amount of the tissue is engaged by the fasteners 1400 to maintain the fasteners 1400 in the fastened position.

FIGS. 7A to 7F sequentially illustrate the firing of a first fastener 1400 from a firing or driving device or mechanism 1500 into a tissue 900, e.g., heart 900. The firing mechanism 1500 includes a firing pin 1510 that is axially slidable within the interior of a sleeve 1170 of the fastening arm 1150. The sleeve 1170 includes features that are positionally fixed with respect the remainder of the sleeve 1170 and suitable for driving fasteners, e.g., a bore for housing the fasteners, a distal wall portion 1175, and a cam or ramp 1180. It should be appreciated, however, that one or more of these features may be configured to be movable with respect to the other portions of the sleeve 1170.

Fastening arm 1150 shares features in common with fastening arms 1100 but differs in that no curved fingers 1110 are provided. Thus, the mechanisms described for the driving/firing of fasteners 1400 from fastening arm 1150 are substantially the same as those of fastening arms 1100. Moreover, these fastener-driving mechanisms may be used in different arrangements, e.g., with a single fastening arm 1150 that is maneuverable as a catheter, similar to catheter 1000.

The firing pin 1510 includes a head 1515 that engages and is attached to a proximal end of a spring 1520. The distal end of the spring 1520 engages and is attached to the distal wall portion 1175 of the sleeve 1170. The distal wall 1175 includes an aperture through which a distal firing portion 1525 extends when in the position illustrated in FIG. 7A.

Extending proximally from the head of the firing pin 1510 is a first hook element 1530 in the form of a loop. As illustrated, e.g., in FIGS. 7A and 7B, the first hook element 1530 is releasably engaged by a second hook element 1535 of a trigger element 1540. Trigger element 1540 is connected to a firing shaft or cable 1545, which may be flexible, rigid, or a combination of flexible portions and rigid portions. The trigger element 1540 is rotatably attached to the firing cable 1545 at a pivot joint 1550. The distal end of the shaft or cable 1545 includes a clevis that supports the opposite sides of the pivot joint 1550.

Figure 7A:
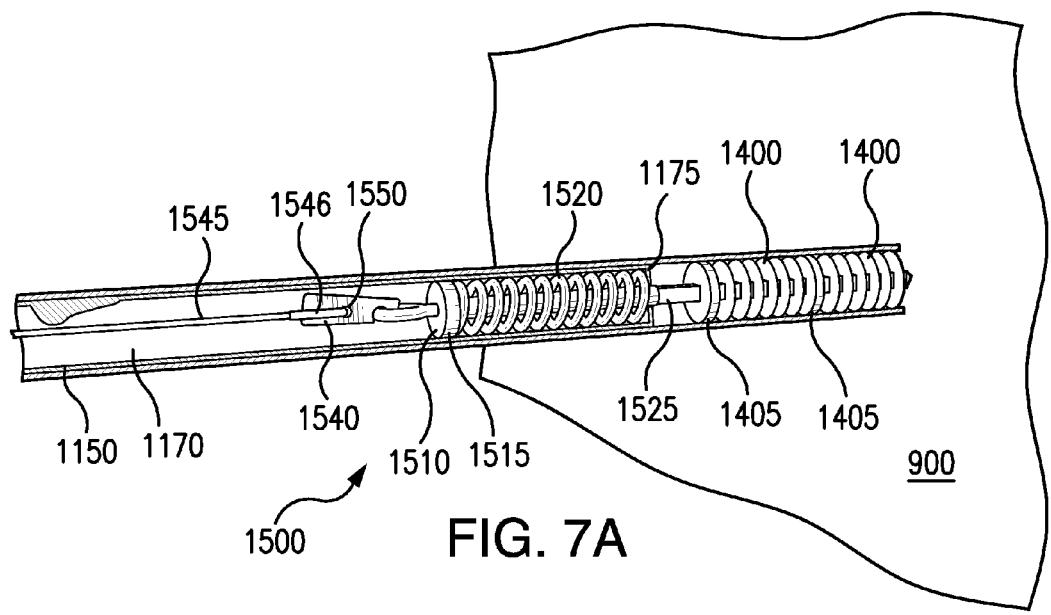
FIGS. 7A to 7F sequentially illustrates the driving of a first fastener from a driving mechanism into a tissue.
Figure 7B:
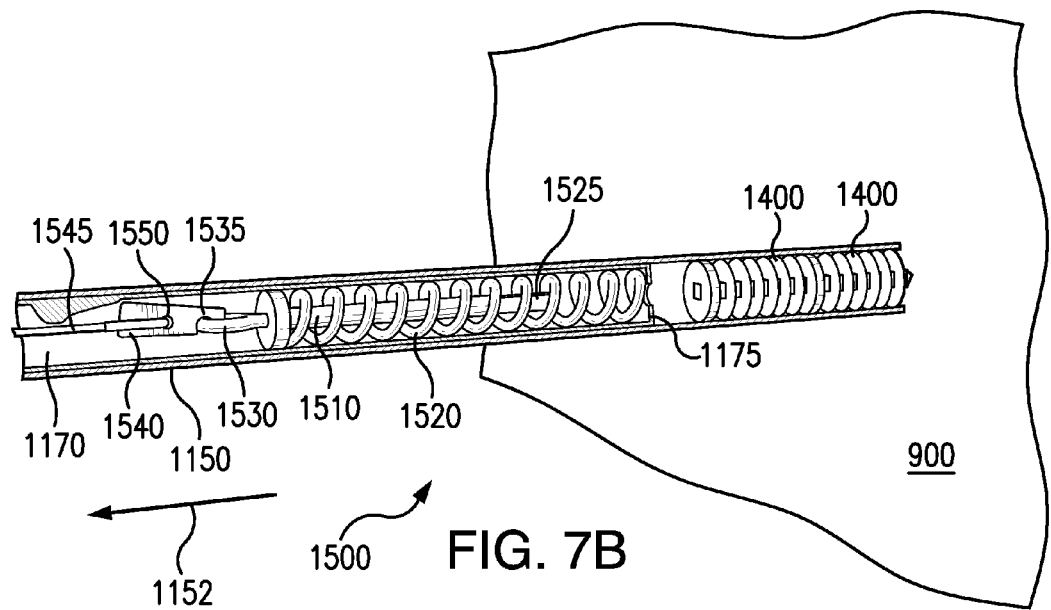

In the position illustrated in FIG. 7A, the firing pin 1510 and spring 1520 are in a rest state, i.e., the spring 1520 is not under any, or substantially any, axial compression or tension force. As the firing pin 1510 is pulled in a proximal direction (as indicated by arrow 1152 in FIG. 7B) by the firing cable 1545, via the engagement between the first hook element 1530 and the second hook element 1535, the spring 1520 is pulled and axially extended such that the spring 1520 acts as a tension spring, thereby applying an axially distal spring force to the firing pin 1510. It should be understood, however, that in the initial state illustrated in FIG. 7A, the spring may already be under some tension, i.e., the rest state of the firing pin 1510 may be distal to the initial position illustrated in FIG. 7A.

Figure 7C:
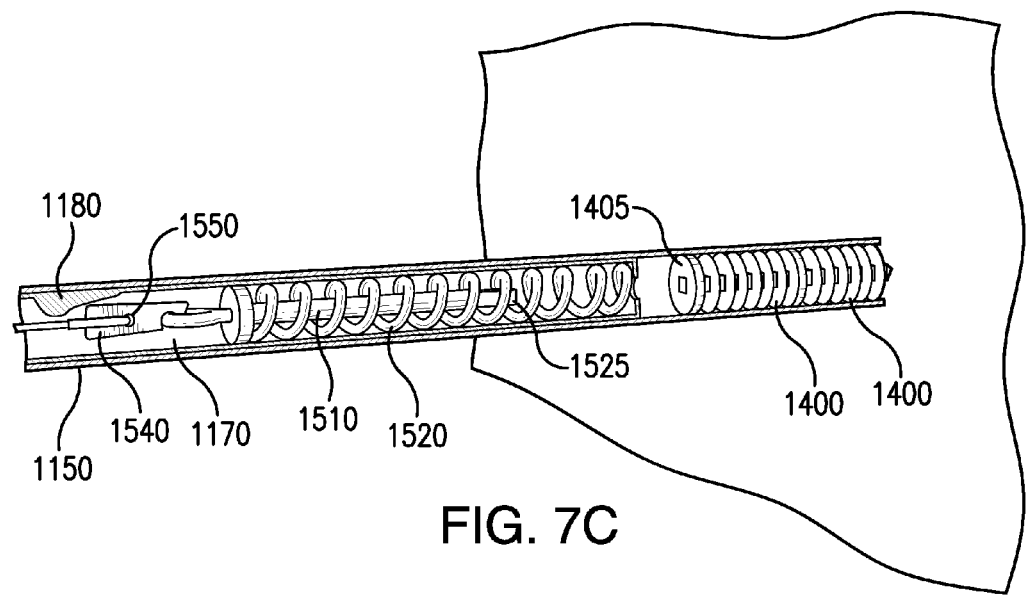
Figure 7D:
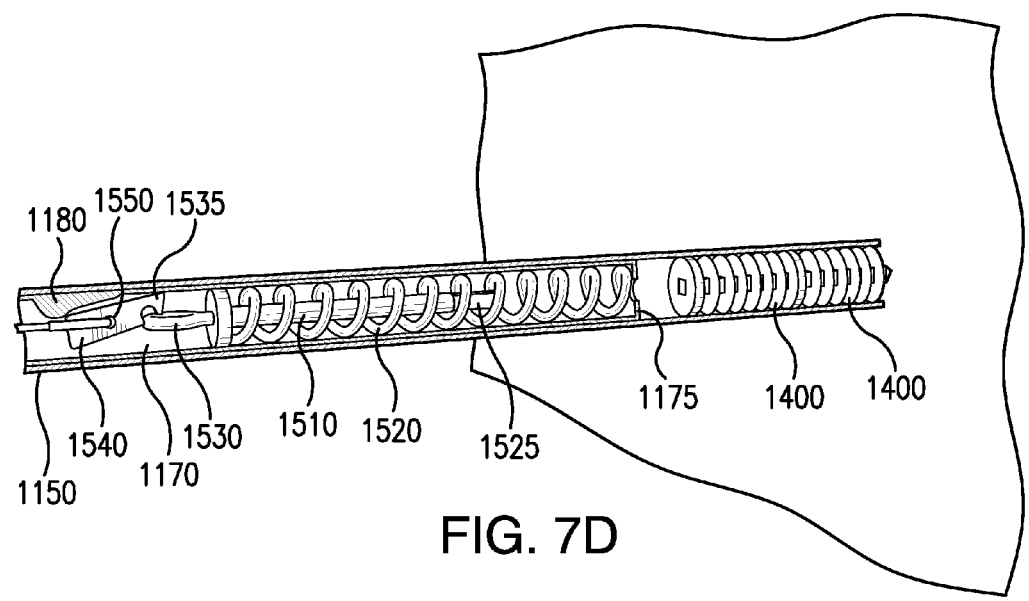

As illustrated sequentially in FIGS. 7C and 7D, the firing pin 1510 is further pulled proximally (and the spring 1520, as a result, being further stretched to apply greater distally directed axial force on the firing pin 1510) until a proximal portion (i.e., a portion proximal to the pivot joint 1550) of the trigger element 1540 contacts and slides along a cam or ramp 1180 that is axially fixed, or substantially axially fixed, with respect to the sleeve 1170. This causes, as illustrated in FIG. 7D, a rotation of the trigger element 1540 about the pivot joint 1550 until the second hook element 1535 pivots away from engagement with the first hook element 1530, thereby releasing the firing pin 1510. As such, the firing pin 1510 rapidly moves distally forward, in the distal direction as indicated by arrow 1151 in FIG. 7E, due to the built up tension (i.e., the release of the stored energy) in the spring 1520 until the firing pin reaches the fully distally extended position illustrated in FIG. 7E.

Figure 7E:
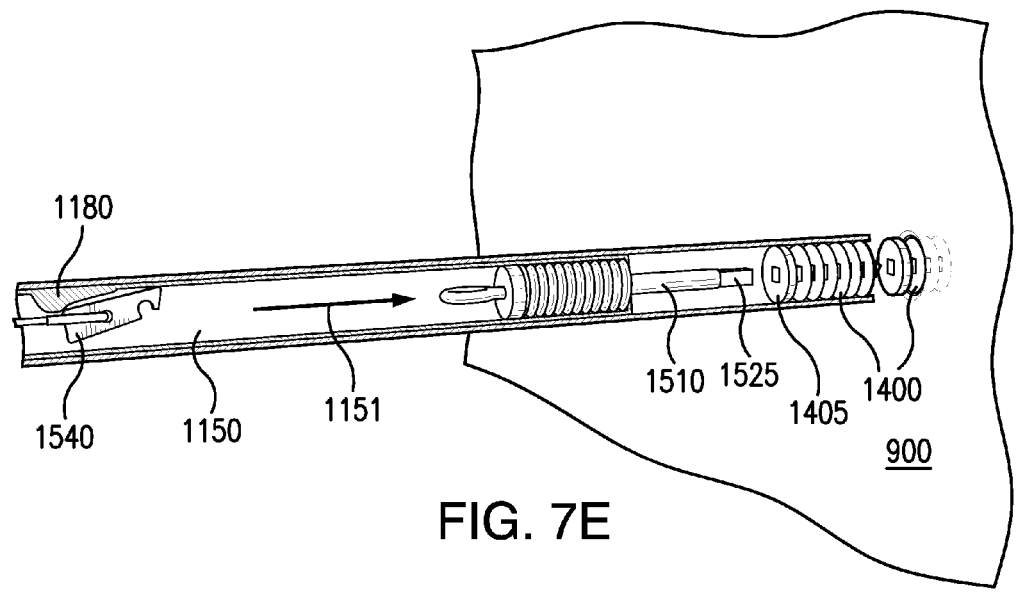

As the firing pin 1510 travels between the fully retracted position of FIG. 7D and the fully extended position of FIG. 7E, the distal end or firing portion 1525 of the firing pin 1510 impacts and imparts momentum to a proximal face or head 1405 of a proximal-most implant or fastener 1400. Since the proximal-most fastener 1400 and the adjacent distal fastener 1400 are in axial communication (i.e., a distal portion or face of the proximal fastener 1400 is in contact with a proximal portion or face of the distal fastener 1400), the force and momentum are also imparted to the distal fastener 1400, thereby firing the distal fastener 1400 outwardly from the distal end of the fastening arm 1150, as illustrated, e.g., in FIG. 7E. The momentum of the fired distal fastener 1400 carries the distal fastener 1400 into the tissue 900. The rapid nature of the discharge of the fastener 1400 ensures that the fastener 1400, which includes many features in common with the implants or fasteners 100, 200, 300, 500, 700 described above, pierces and extends sufficiently into the tissue 900. Otherwise the tip of the fastener 1400 may push the tissue distally without sufficient distal penetration.

The size, spring constant, and travel distance of the spring 1520, as well as the relative masses of the firing pin and the fasteners 1400 may be selected to optimize firing velocity. Although the spring 1520 exerts a tension force on the firing pin when the firing pin is moved proximally, it should be understood that a spring 1520 may be provided that is compressed when the firing pin is moved proximally and extended when the firing pin moves distally beyond the rest position. Moreover, more than one spring may be provided, one or more of which may be tensed when one or more of the other springs is compressed.

Figure 7F:
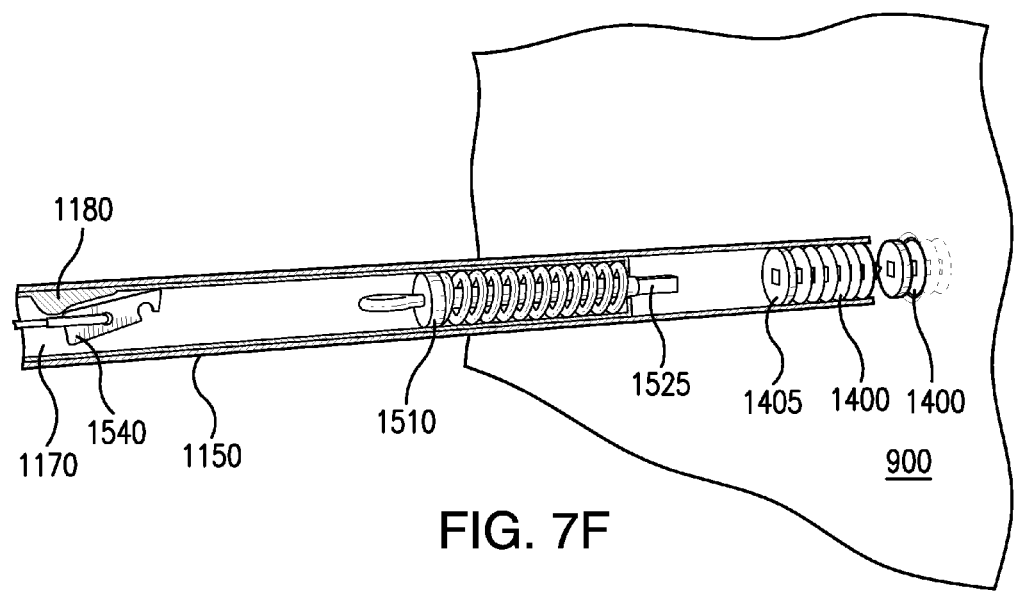

As illustrated in FIG. 7F, the firing pin 1510 and spring 1520 have returned proximally to the rest position. In this regard, the firing of the fastener 1400 is similar in some aspects to the launching mechanism of a pinball machine. It is noted that as the firing pin 1510 moves from the fully retracted to the fully extended position, it passes the rest position, thereby entering a state of compression. It is this compression of the spring 1520 that urges the firing pin 1510 from the fully extended position back toward the rest position as illustrated in FIG. 7F.

During the firing of the distal implant or fastener 1400, the proximal fastener 1400 is translated to the position in which the distal fastener 1400 was located prior to firing of the distal fastener 1400. The proximal fastener 1400 may be prevented from exiting the distal end of the fastening arm 1150 during firing of the distal fastener by any appropriate mechanism, e.g., friction or a releasable latching mechanism. Thus, in order to fire the proximal fastener 1400, the sleeve 1170 along with all of the associated components of the firing mechanism 1500, e.g., the distal wall portion 1175 and the cam or ramp 1180 of the sleeve 1170, the spring 1520, the firing pin 1510, hook element 1530, trigger element 1540, and hook element 1545, is moved distally by approximately the length of the fastener 1400.

FIGS. 8A to 8F sequentially illustrate the repositioning of the driving mechanism and the firing a second implant or fastener 1400 into the tissue 900. This distal movement of the sleeve 1170 and the associated components of the firing mechanism 1500 is illustrated sequentially in FIGS. 8A and 8B. It is noted that in the respective initial positions illustrated in FIGS. 7A and 8B, the distal portion 1525 of the firing pin 1510 directly contacts a proximal head 1405 of the proximal fastener 1400. It should be understood, however, that the firing pin 1510 and the proximal fastener 1400 may be spaced apart in the initial position. In such an arrangement, the forward, or distal, momentum of firing pin 1510 during firing would carry the firing pin 1510 distally beyond the initial position and into contact with the proximal fastener 1400.

Figure 8A:
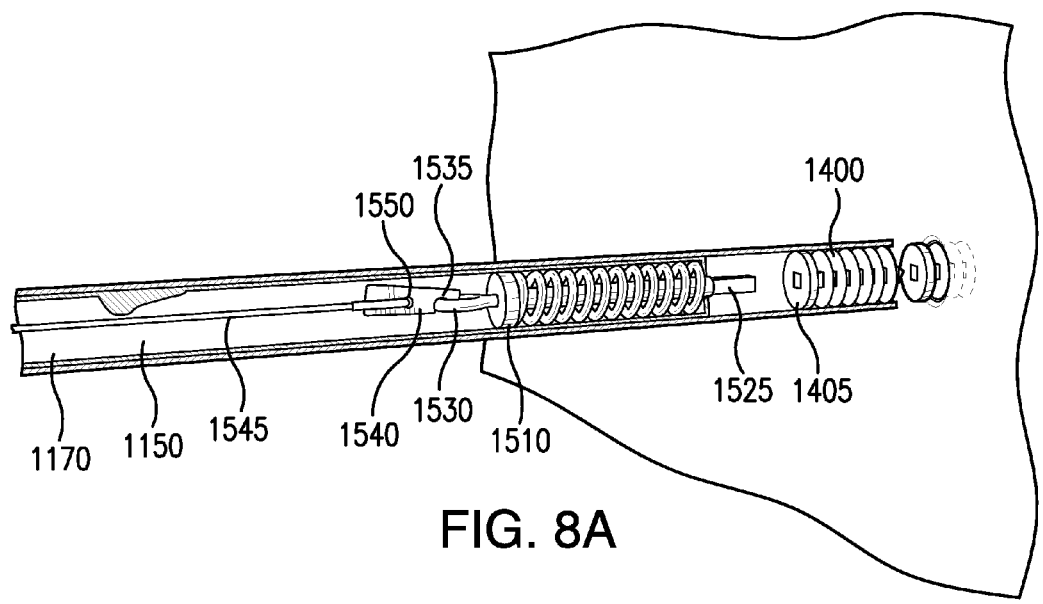
FIGS. 8A to 8F sequentially illustrate the repositioning of the driving mechanism and the driving of a second fastener into the tissue.
Figure 8B:
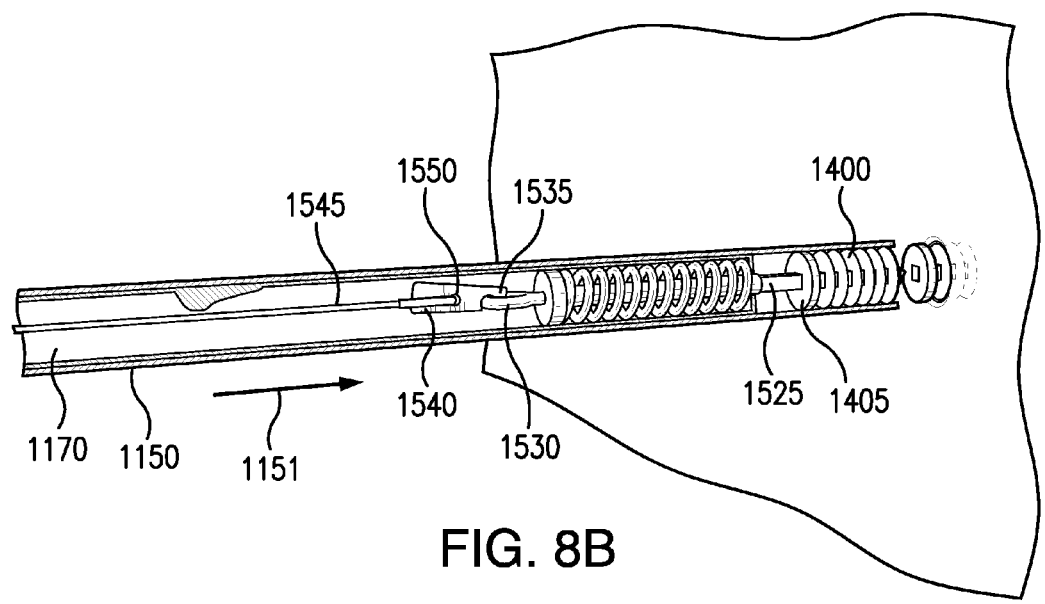

In addition to the distal movement of the sleeve 1170 and other firing mechanism components with respect to the fastening arm 1150, the trigger element 1540 moves distally with respect to the sleeve 1170 so that the second hook element 1535 again releasably engages the first hook element 1530, as illustrated, e.g., in FIG. 8A. For this purpose, the second hook element 1535 has a slanted or ramped distal surface that contacts and slides along the first hook element 1530 when the second hook element 1535 and the first hook element 1530 are moved together. This contact and sliding causes the trigger element 1540 to rotate about the pivot joint 1550 and allows the first hook element 1530 to clear the second hook element 1545. The rotated position of the trigger element 1530 is the same as or approximately the same as the rotational position of the trigger element 1530 illustrated in FIG. 7F. Further movement of the second hook element 1535 toward the first hook element 1530 (and/or vice-versa) allows the trigger element 1540 to rotate back to the position illustrated, e.g., in FIG. 8A, with the first hook element 1530 being captured or engaged by the second hook element 1535, again forming a releasably latched or locked configuration. The trigger element 1540 may be urged toward the rotational position shown, e.g., in FIG. 8A by, e.g., a spring bias.

Figure 8C:
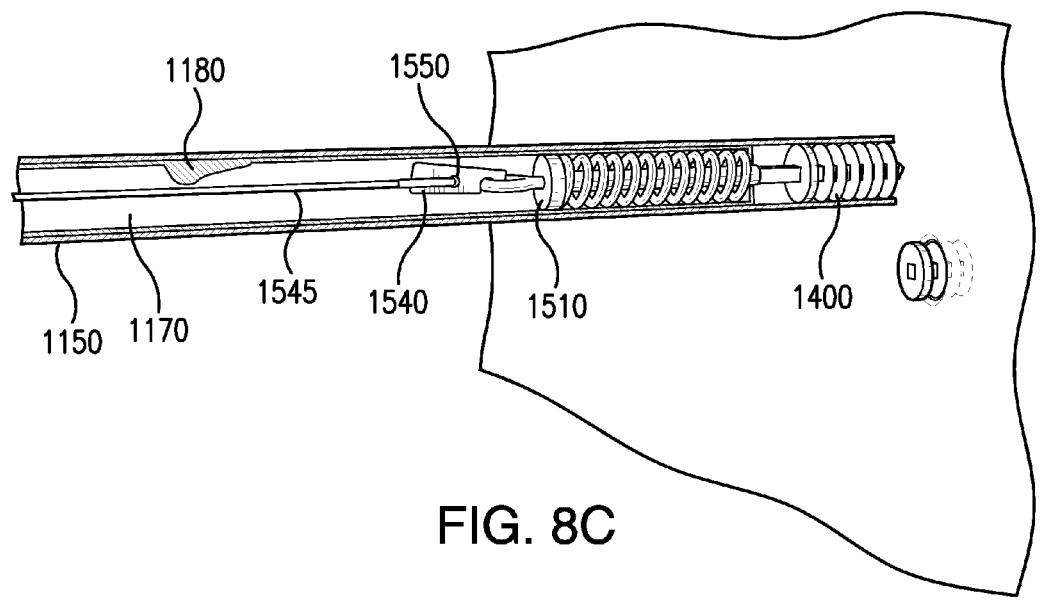

Prior to firing of the second or proximal fastener 1400, the fastening arm 1150 is repositioned as illustrated, e.g., in FIG. 8C. This repositioning may correspond, e.g., to the repositioning sequentially illustrated between FIGS. 5B and 5C.

Figure 8D:
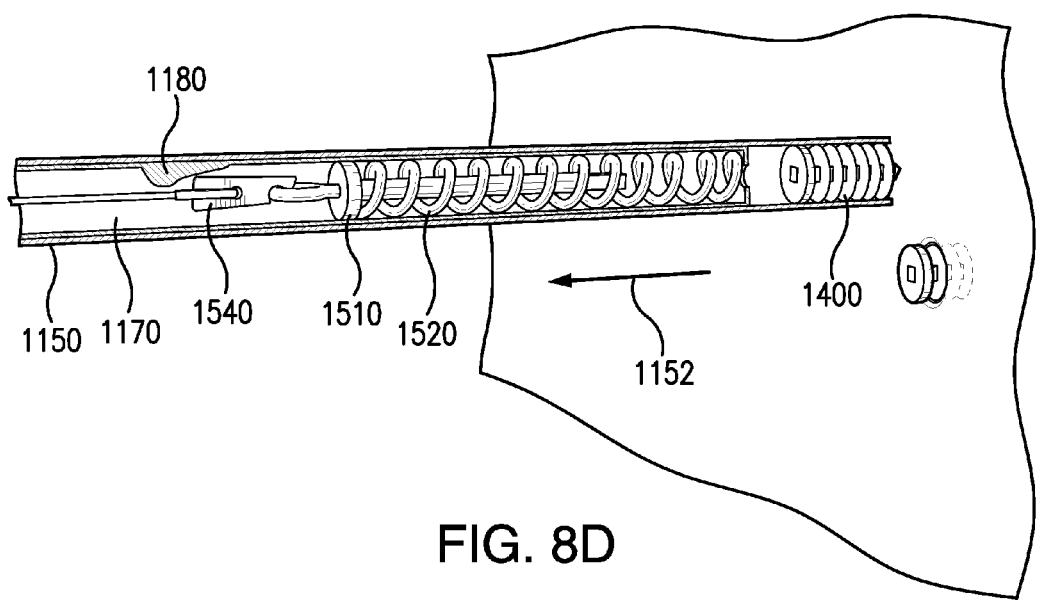

The proximal implant or fastener 1400 is then fired in a manner analogous to that described above with regard to the distal fastener 1400. In particular, as sequentially illustrated in FIGS. 8C and 8D, the firing pin 1510 is pulled in the proximal direction, indicated by arrow 1152, by the firing cable 1545, via the engagement between the first hook element 1530 and the second hook element 1535. Thus, the spring 1520 is pulled and axially extended or stretched such that the spring 1520 acts as a tension spring, thereby applying an axially distal spring force to the firing pin 1510. As illustrated in FIG. 8D, the firing pin 1510 is pulled proximally until a proximal portion (i.e., a portion proximal to the pivot joint 1550) of the trigger element 1540 contacts and slides along the cam or ramp 1180. Further proximal pulling of the firing pin 1510 causes a rotation of the trigger element 1540 about the pivot joint 1550 until the second hook element 1535 pivots away from engagement with the first hook element 1530, thereby releasing the firing pin 1510. As such, the firing pin 1510 again rapidly moves distally forward, in the distal direction as indicated by arrow 1151 in FIG. 8E, due to the built up tension in the spring 1520 until the firing pin reaches the fully distally extended position illustrated in FIG. 8E. Since, as indicated above, the cam or ramp 1180 is axially fixed, or substantially axially fixed, with respect to the sleeve 1170, the distance the spring is pulled prior to triggering is substantially constant, thereby providing a consistent spring force regardless of axial position of the tube and driving components. However, it should be understood that the spring distance may be configured to be varied.

Figure 8E:
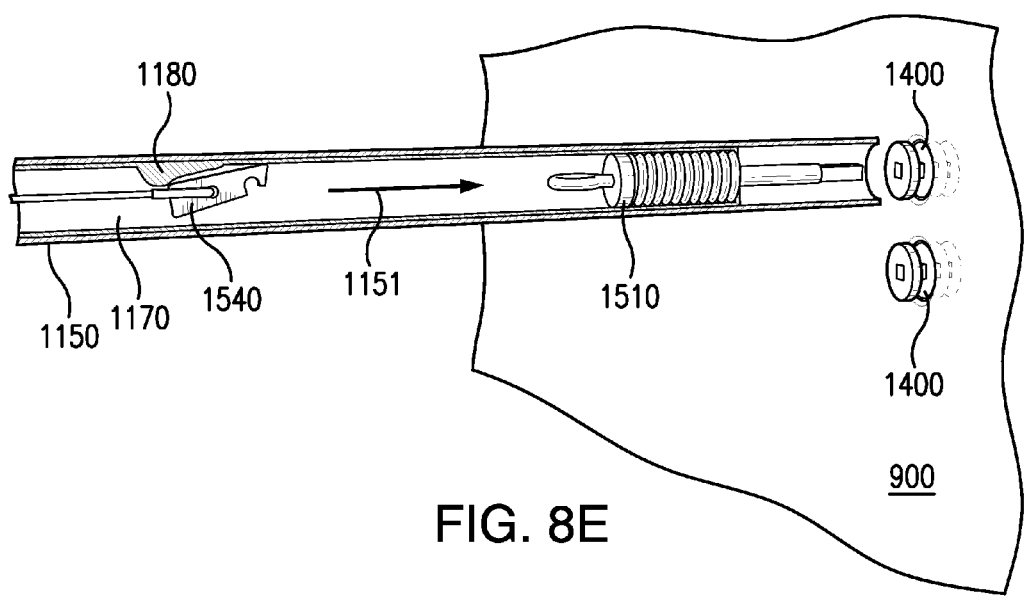

As the firing pin 1510 travels between the fully retracted position and the fully extended position of FIG. 8E, the distal end or firing portion 1525 of the firing pin 1510 impacts and imparts momentum to the proximal face or head 1405 of the proximal fastener 1400. The force and momentum imparted to the proximal fastener 1400 fires the proximal fastener 1400 outwardly from the distal end of the fastening arm 1150, as illustrated, e.g., in FIG. 8F. The momentum of the fired proximal fastener 1400 carries the proximal fastener 1400 into the tissue 900. As with the firing of the distal fastener 1400, the rapid nature of the discharge of the proximal fastener 1400 ensures that the proximal fastener 1400 pierces and extends sufficiently into the tissue 900, rather than pushing the tissue 900 distally without sufficient distal penetration.

Figure 8F:
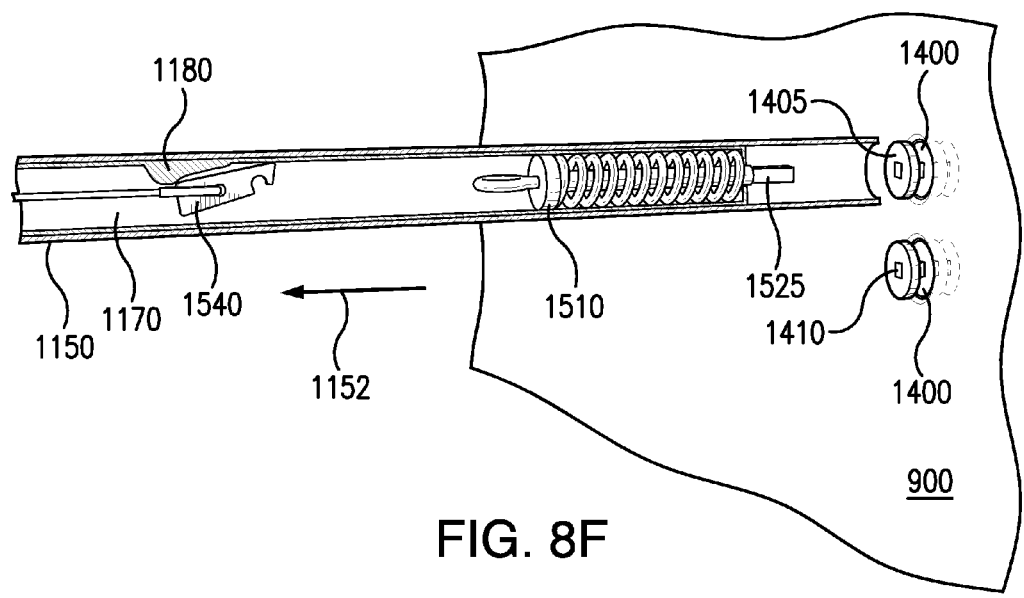

The proximal heads 1405 of the fasteners 1400 include recesses 1410, illustrated, e.g., in FIG. 8F, that mate with distal portion 1525 of the firing pin 1510. In this regard, the recesses 1410 may have complementary geometry, e.g., rounded and/or polygonal, and/or a similar size. The recess helps to maintain proper radial positioning of the distal portion 1525 of the firing pin 1510 during impact and reduces any chance of deflection along the proximal face of the proximal head 1405. This helps to ensure that the momentum and force are properly imparted from the firing pin 1510 to the implant or fastener 1400. Moreover, the recesses 1410 may have complementary geometry, e.g., rounded or polygonal, and/or a similar size to a distal end portion 1415 (illustrated, e.g., in FIGS. 9A and 9B) of the implants or fasteners 1400. Thus, when two or more fasteners 1400 are loaded end-to-end, as illustrated, e.g., in FIG. 7A, the distal end portion 1415 of a proximal fastener engages and mates with a recess 1410 of a distal adjacent fastener 1400, and so on. Further, the geometry may be chosen to key the two or more adjacent fasteners 1400 to prevent or limit a range of rotation of each fastener 1400 with respect to adjacent fasteners 1400.

Figure 9A:
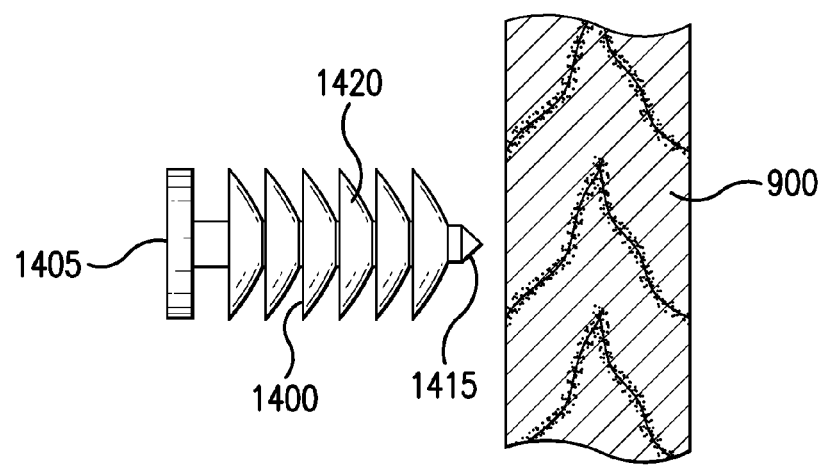
FIGS. 9A and 9B show a cross-sectional view of the tissue before and after the firing of a fastener into the tissue.
Figure 9B:
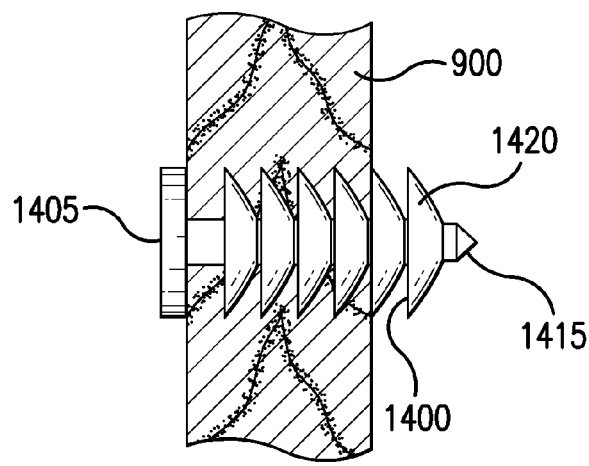

FIGS. 9A and 9B show a cross section of the tissue 900 before and after the firing of an implant or fastener 1400 into the tissue 900. The distal end portion 1415 of the fastener 1400 is sharp, or needle-like, as described above with regard to fasteners 100, 200, 300, 500, 700, which facilitates penetration of the tissue 900 as the implant or fastener 1400 initially pierces the tissue and continues to progress through the tissue. The fastener 1400 includes a plurality of circumferential teeth 1420 that function in a manner analogous to the filaments 115, 215 of, e.g., the fasteners 100, 200 described in greater detail below. In this regard, a distal face of each tooth 1420 is slanted or sloped in a proximal direction to ease distal movement or sliding of the tooth 1420 along the adjacent tissue 900 as the fastener 1400 is distally progressing through the tissue 1400. The proximal face, however, is flat or also has a proximal slant. This allows the radially outer portion of the tooth 1420 to tend to catch or dig in to the adjacent tissue 900 when the fastener is urged in the proximal direction. Thus, the teeth 1420 act to secure the fastener 1400 in the distal inserted position in a manner analogous to the filaments 115, 215 described in greater detail below. Although the teeth 1420 have a constant diameter, it should be understood that teeth 1420 with different diameters, e.g., a set of teeth 1420 that distally and/or proximally taper, may be provided. Moreover, the teeth 1420 need not be round and may have any appropriate cross-sectional shape.

To prevent or resist over-insertion, the distal face of the head portion 1405 also is flat, or substantially flat, to resist insertion of the head portion 1405 into the tissue 900. The head portion 1405 may be provided with a distal surface that is sloped in a distal direction, i.e., a concave distal surface, which may further resist insertion and/or penetration of the head portion 1405 into the tissue 900.

Although FIGS. 9A and 9B show fasteners 1400 that entirely penetrate the tissue 900, i.e., penetrate a back surface of the tissue 900, it should be appreciated that the fasteners 1400 may extend less than fully through a portion of tissue. Moreover, it should be understood that the driving or firing devices or mechanisms of FIGS. 7A to 9B may utilize the implants or fasteners 100, 200, 300, 500, 700 described above, or any other appropriate implants or fasteners.

After driving of all of the desired fasteners 1400, the fastening arm 1150 may be retracted from the insertion site.

Figure 10A:
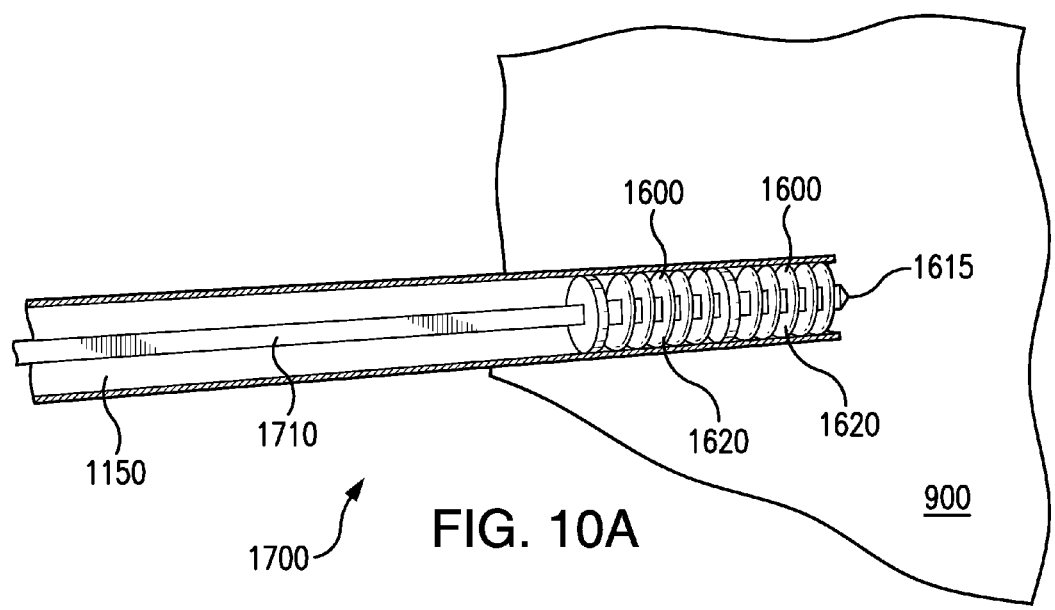
FIGS. 10A to 10C sequentially illustrate the driving of a first fastener from a driving mechanism into a tissue.
Figure 10B:
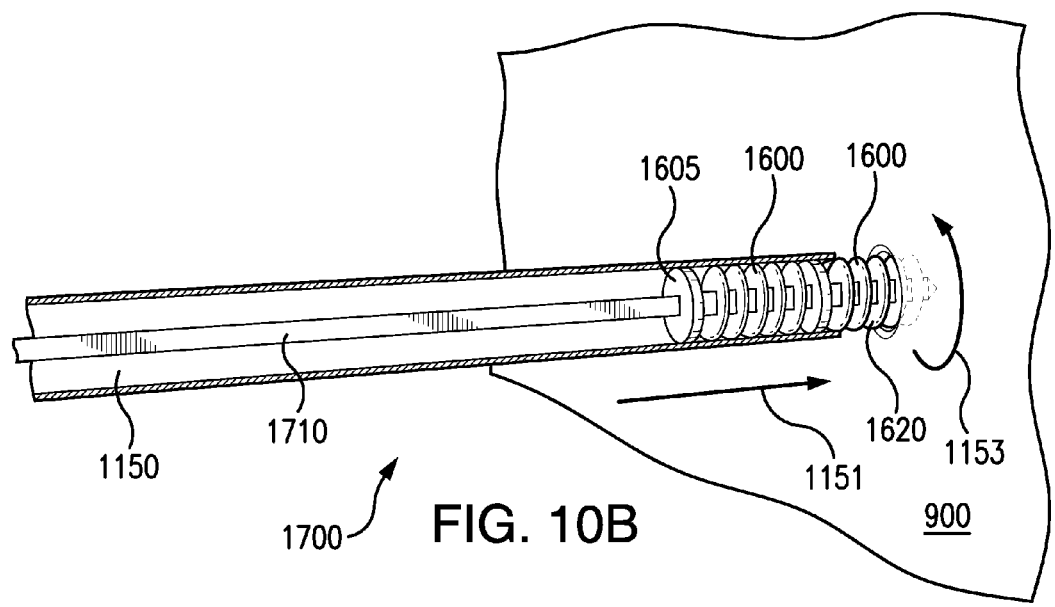
Figure 10C:
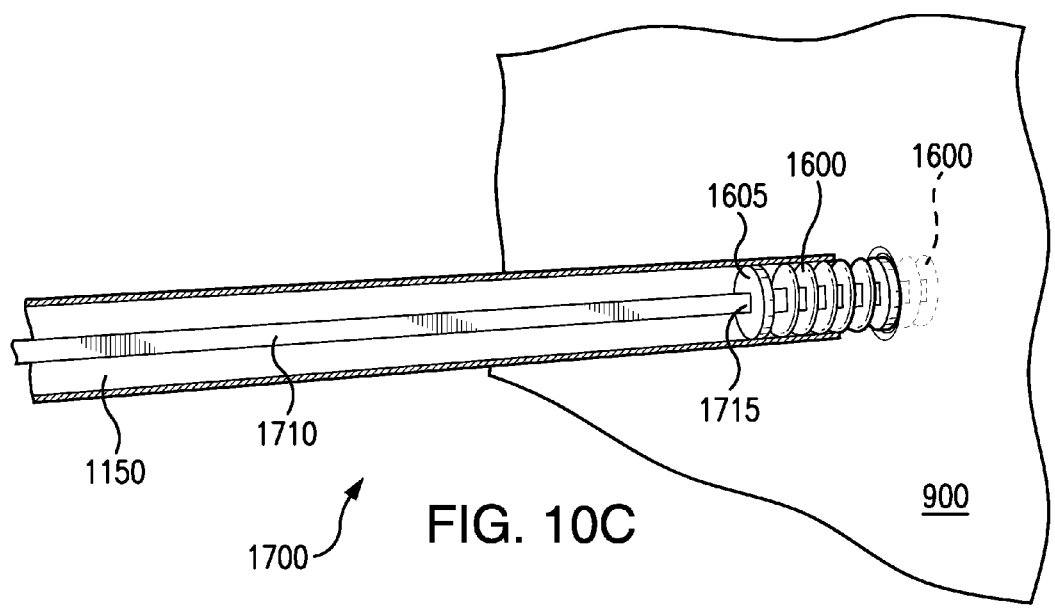

FIGS. 10A to 10C sequentially illustrate the driving of a first implant or fastener 1600 from a driving mechanism 1700 into tissue 900. The driving mechanism 1700 is disposed in the fastening arm 1150. In this regard, the driving mechanism 1700 may be swappable or interchangeable with the driving mechanism 1500 described above for a given fastening arm 1150, providing versatility for a single medical device.

As illustrated in FIG. 10A, the fastening arm 1150 is maneuvered into proximity of the tissue 900 at a location where a distal implant or fastener 1600 of two end-to-end fasteners 1600 is to be driven. Prior to driving the distal fastener 1600, the tip of the distal end portion 1615 may or may not be in contact with the tissue 900 in the position illustrated in FIG. 10A. The same holds for the arrangements described above for driving the fasteners 100, 200, 300, 500, 700, and 1400, or any other implants or fasteners described herein. Once the fastening arm 1150 is positioned as illustrated in FIG. 10A, the distal fastener 1600 is driven into the tissue 900.

To drive the fasteners 1600 into the tissue 900, the driving mechanism 1700 includes a driving shaft 1710 that extends axially along the length of the fastening arm 1150. The driving shaft 1710 transfers rotational force from a proximally located actuator, e.g., an electric motor of a hand-held device, to fasteners 1600, while also progressing distally as the fasteners 1700 advance along the longitudinal axis of the fastening arm 1150. Thus, the driving shaft 1710, along with the fasteners 1600 simultaneously move in the distal direction, indicated by arrow 1151, and rotate about the longitudinal axis of the fastening arm 1150 and the driving shaft 1710, the rotation indicated by arrow 1153. It should be understood that for driving the fasteners 1700, the fasteners may be rotated either clockwise or counter-clockwise and that different fasteners 1700 may require different respective rotation directions within the same system.

As the distal implant or fastener 1600 rotates and distally advances, the tip portion initially contacts and pierces the tissue, followed by engagement of external threads 1620, as illustrated, e.g., in FIG. 10B. The rate of distal advancement and the rate of rotation correspond, e.g., to the size and pitch of the threads 1620. Once the threads 1620 engage, the further rotation of the threads 1620 helps to pull the fastener 1600 through the tissue 900, preventing or resisting distal pushing of the tissue 900.

In order to transfer the rotation and rotational force from the driving shaft 1710 to the proximal implant or fastener 1600, the proximal head 1605 has a recess 1610 that is keyed to the cross-sectional geometry of the distal end portion, or driving head, 1715 driving shaft 1710, to prevent, or substantially prevent, rotation of the proximal fastener 1600 with respect to the driving shaft 1710. Thus, the insertion of the driving head 1715 of the driving shaft 1710 into the recess 1610 provides a driving interface for the rotation of the proximal fastener 1600. Similarly, in order to transfer the rotation and rotational force from one fastener 1600 to an adjacent fastener 1600, the fasteners 1600 have distal end portions 1615 that also have a geometry that is keyed to the recess 1610 to prevent, or substantially prevent rotation. Thus, in the arrangement illustrated in FIGS. 10A to 10C, the driving shaft 1710 engages the recess 1610 of the proximal fastener 1600 and the distal end portion 1615 of the proximal fastener engages the recess 1610 of the distal fastener 1600, thereby transferring rotation and rotational force from the driving shaft 1710 to both the proximal fastener 1600 and the distal fastener 1600.

Further, the engagement of the driving head 1715 with the recess 1610 of the proximal fastener 1600 and the engagement of the distal end portion 1615 of the proximal fastener and the recess 1610 of the distal fastener 1600 also provides a distal driving interface whereby distal movement of the driving shaft 1710 causes distal movement of both the proximal and distal fasteners 1600.

Although the recesses 1610, the distal end portions 1615, and the driving head 1715 all have corresponding rectangular cross-sectional geometries, it should be understood that any other appropriate keyed engagement geometry or engagement mechanism may be provided.

Figure 11A:
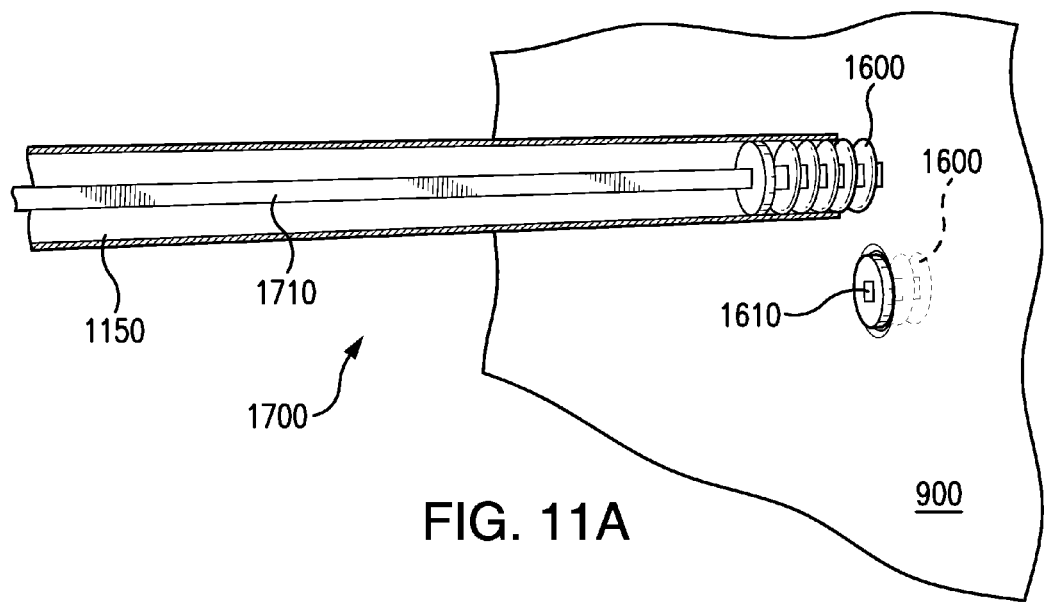
FIGS. 11A and 11B sequentially illustrate the repositioning of the driving mechanism and the firing a second fastener into the tissue.

FIG. 10C shows the distal implant or fastener 1600 in a fully inserted position. At this stage, the fastening arm 1150 may be moved proximally to disengage the distal end portion 1615 of the proximal fastener 1600 (which remains coupled to the fastening arm 1150) from the recess 1610 of the distal fastener 1600. The fastening arm 1150 is then repositioned to a second fastening location as illustrated in FIG. 11A. This repositioning may correspond, for example, to the repositioning sequentially illustrated between FIGS. 5B and 5C.

Figure 11B:
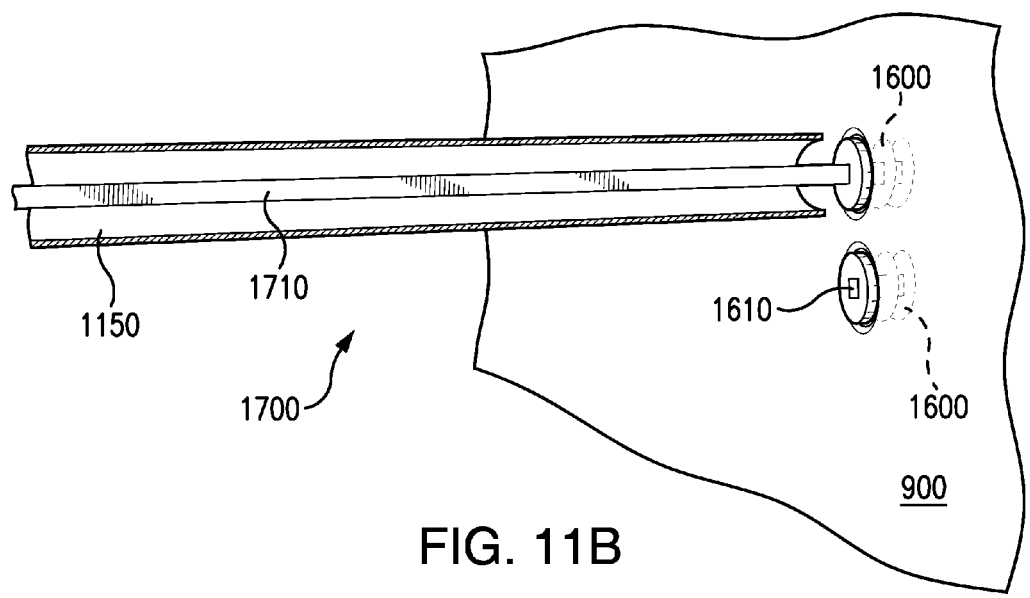

As illustrated in FIG. 11B, the proximal fastener 1600 is then driven in a manner analogous to that described above with respect to the distal fastener 1600. The driving of the proximal fastener 1600 differs from the driving of the distal fastener 1600, however, in that the driving shaft 1710 directly drives, i.e., directly rotates and distally translates, the proximal fastener 1600 without transferring the rotation and distal translation through an intermediary fastener 1600.

Figure 12A:
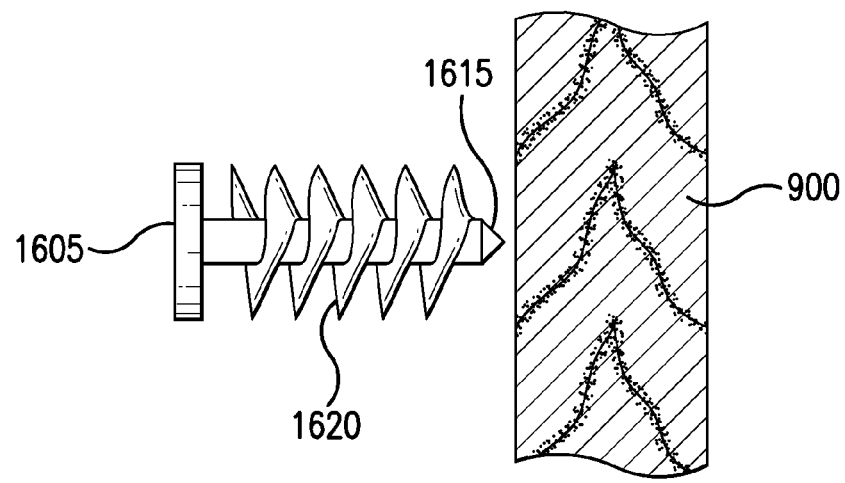
FIGS. 12A and 12B show a cross-sectional view of the tissue before and after the driving of a fastener into the tissue.
Figure 12B:
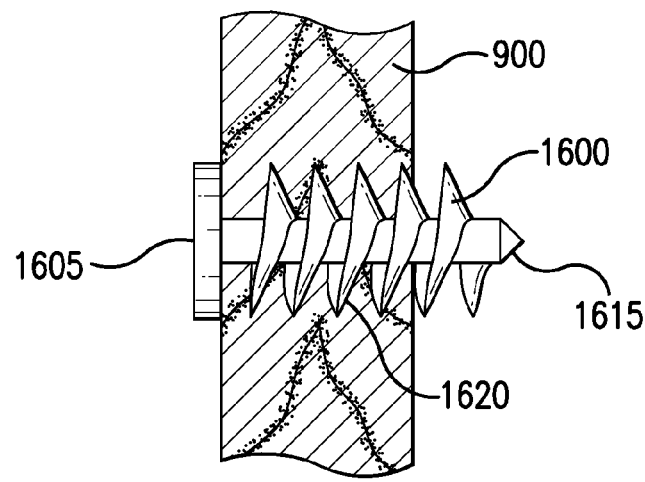

FIGS. 12A and 12B show a cross section of the tissue 900 before and after the firing of a fastener 1600 into the tissue 900. The distal end portion 1615 of the fastener 1600 is sharp, or needle-like, as described above with regard to fasteners 100, 200, 300, 500, 700, and 1400, which facilitates penetration of the tissue 900 as the fastener 1600 initially pierces the tissue 900 and continues to progress through the tissue 900. As indicated above, the fastener 1600 includes threads 1620 that assist in penetration of the fastener 1600 into the tissue 900. Further, the threads 1620 act to secure the fastener 1600 in the distal inserted position. Moreover, it should be understood that the fastener 1600 may be provided with reversed threads to help prevent the fastener 1600 from backing out due to rotation in a direction opposite the direction in which the fastener 1600 was installed. Although the threads 1620 have a constant diameter and pitch, it should be understood that threads 1620 with non-constant pitches and diameters, e.g., threads 1620 that distally and/or proximally taper, may be provided.

To prevent or resist over-insertion, the distal face of the head portion 1605 is flat, or substantially flat, to resist insertion of the head portion 1605 into the tissue 900. The head portion 1605 may be provided with a distal surface that is sloped in a distal direction, i.e., a concave distal surface, which may further resist insertion and/or penetration of the head portion 1605 into the tissue 900.

Although FIGS. 12A and 12B show fasteners 1600 that entirely penetrate the tissue 900, i.e., penetrate a back surface of the tissue 900, it should be appreciated that the fasteners 1600 may extend less than fully through a portion of tissue.

After driving of all of the desired fasteners 1600, the fastening arm 1150 may be retracted from the surgical site.

The driving devices illustrated in FIGS. 7A to 12B, as with the driving devices described below with respect to FIGS. 21A to 22 and any other driving devices described herein, allow for implants to be driven into a tissue from a single side, eliminating the need to access the opposite side of the tissue. This simplifies the procedure and may help to minimize the risk of, e.g., operator error or other complications that may arise with maneuvering a tool to access the second, opposite side of the tissue. Referring to the driving device of FIGS. 7A to 9B, the need for tool access to the second side of the tissue is eliminated by imparting sufficient speed and momentum to the implants 1400 in combination with the provision of the pointed, needle-like tip and tapered front portion of the implants 1400. The implants are preferably driven at a speed greater than 50 meters per second, more preferably in a range of 50 to 350 meters per second, and most preferably at 350 meters per second. However, it should be understood that the implants may be driven at any suitable speed sufficient for the implants to puncture tissue.

Referring to the driving device of FIGS. 10A to 12B, the need for tool access to the second side of the tissue is eliminated by initially piercing the tissue with the pointed, needle-like tip of the implant 1600, followed by engagement of the threads 1620 of the implant 1600 with the tissue and the rotation of the threads 1620 during distal advancement of the implant 1600.

Although the example driving devices or mechanisms illustrated, e.g., in FIGS. 7A to 12B are arranged to fire two implants or fasteners 1400, 1600, it should be understood that the driving mechanisms may be arranged to fire any appropriate number of implants or fasteners 1400, 1600, including more than two implants or fasteners 1400, 1600 or a single implant or fastener 1400, 1600.

Further, the driving mechanisms described herein may be actuated in any appropriate manner, including, e.g., electro-mechanical and/or hand-powered actuation.

As with the fasteners 100, 200, 300, 500, 700, the fasteners 1400, 1600 may be absorbable or non-absorbable into the patient's body, depending, e.g., on the particular operation.

Figure 13A:
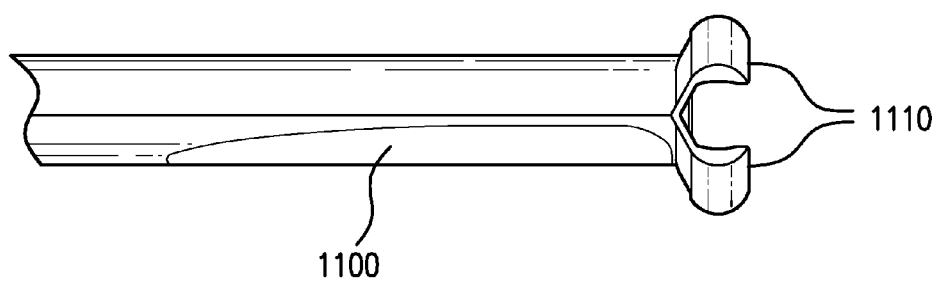
FIG. 13A shows a fastening arm.
Figure 13B:
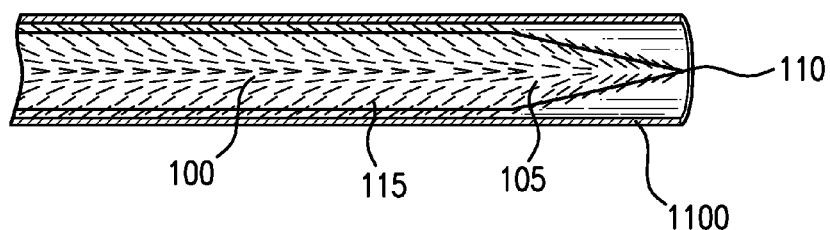
FIG. 13B shows a cross-sectional view of the fastening arm of FIG. 13A.
Figure 20:
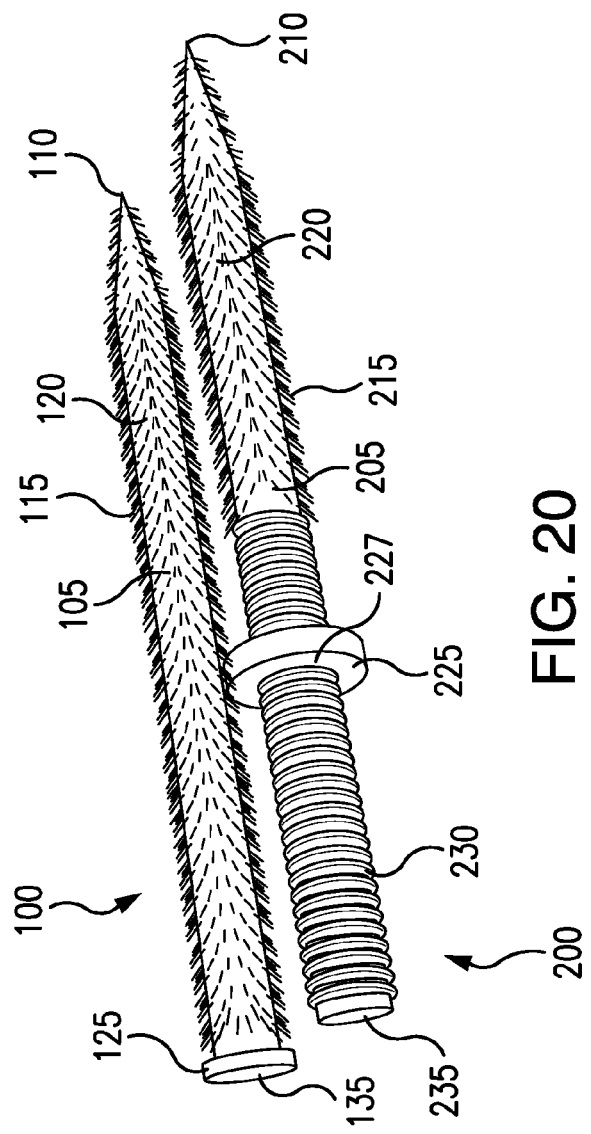
FIG. 20 is an illustration of two surgical implants.

FIG. 13A illustrates one of the fastening arms 1100 as illustrated, e.g., in FIG. 3A, including curved fingers 1110. FIG. 13B illustrates the fastening arm 1100 of FIG. 13A in cross-section. As illustrated in FIG. 13B, the housing of the fastening arm 1100 houses an implant or fastener 100, which is also illustrated in FIG. 20 and described in greater detail below in connection with FIG. 20.

Figure 14B:
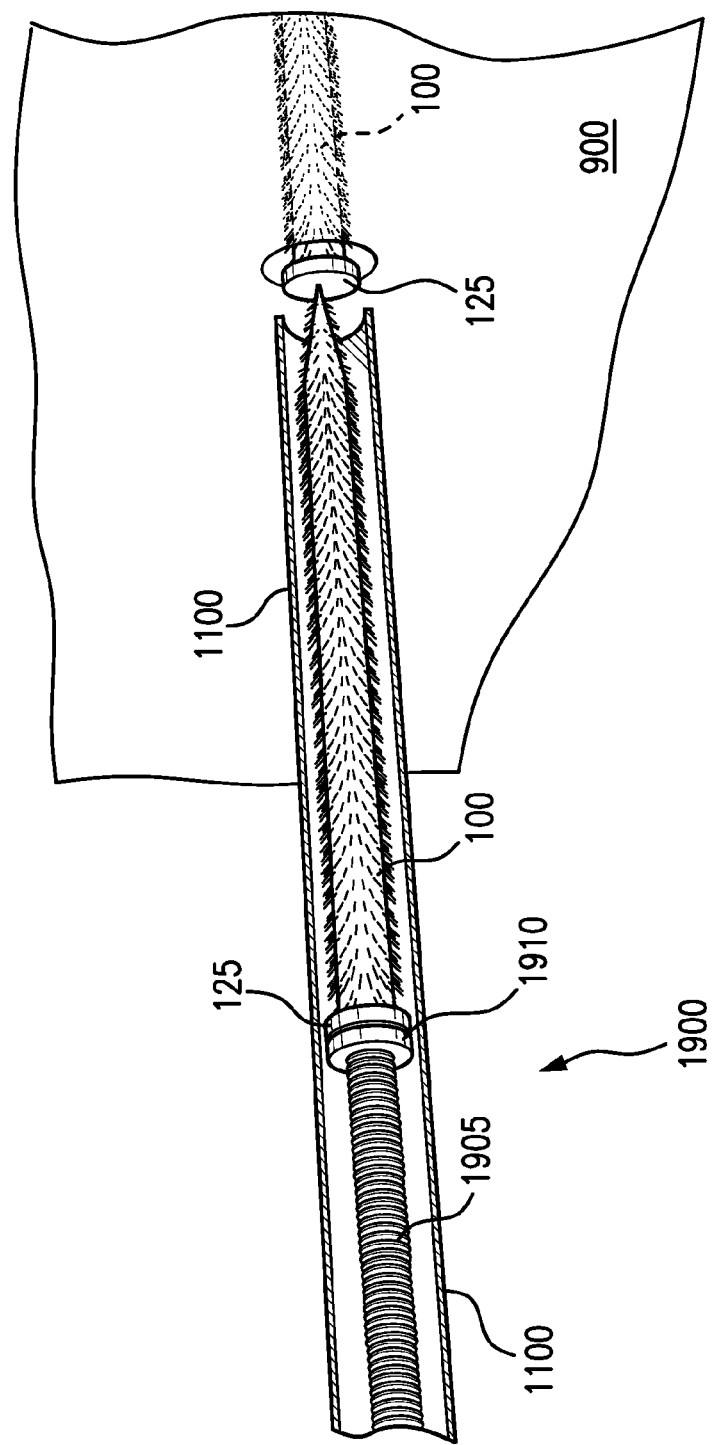

As illustrated in FIGS. 14A and 14B, which also show the fastening arm 1100 in cross section, the fastening arm 1100 houses two implants or fasteners 100. FIGS. 14A and 14B sequentially illustrate the driving of a distal fastener 100 into a tissue 900. Referring to FIG. 14A, the distal end of the fastening arm 1100 is positioned in contact with or in proximity to the tissue 900. In this position, the distal tip 115 of the distal fastener 100 is in contact with or near the tissue 900.

To drive the distal fastener 1100 into the tissue 900, a driving mechanism 1900 includes a threaded pushrod 1905 connected to a distal head 1910. As the pushrod 1905 is pushed distally, e.g., by rotating an internally threaded driver with respect to the externally threaded pushrod 1905, the distal head 1910 is also pushed distally. Due to contact between the distal head 1910 and the proximal head 125 of the proximal fastener 100, the proximal fastener 100 is also pushed distally. Further, a distal portion in the region of the tip 110 of the proximal fastener 100 contacts the proximal head 125 of the distal fastener 100. This contact causes the distal movement of the proximal fastener 100 to distally push the distal fastener 100. As such, the distal movement of the distal head 1910 causes pushes both the proximal and distal fasteners 100. In this manner, as illustrated in FIG. 14B, the distal fastener 100 is driven into the tissue 900.

Although the pushrod 1905 is a threaded cylinder, it should be appreciated that a non-threaded and/or non-circular pushrod may be provided. Moreover, the pushrod may be distally actuated by any appropriate mechanism.

Figure 14C:
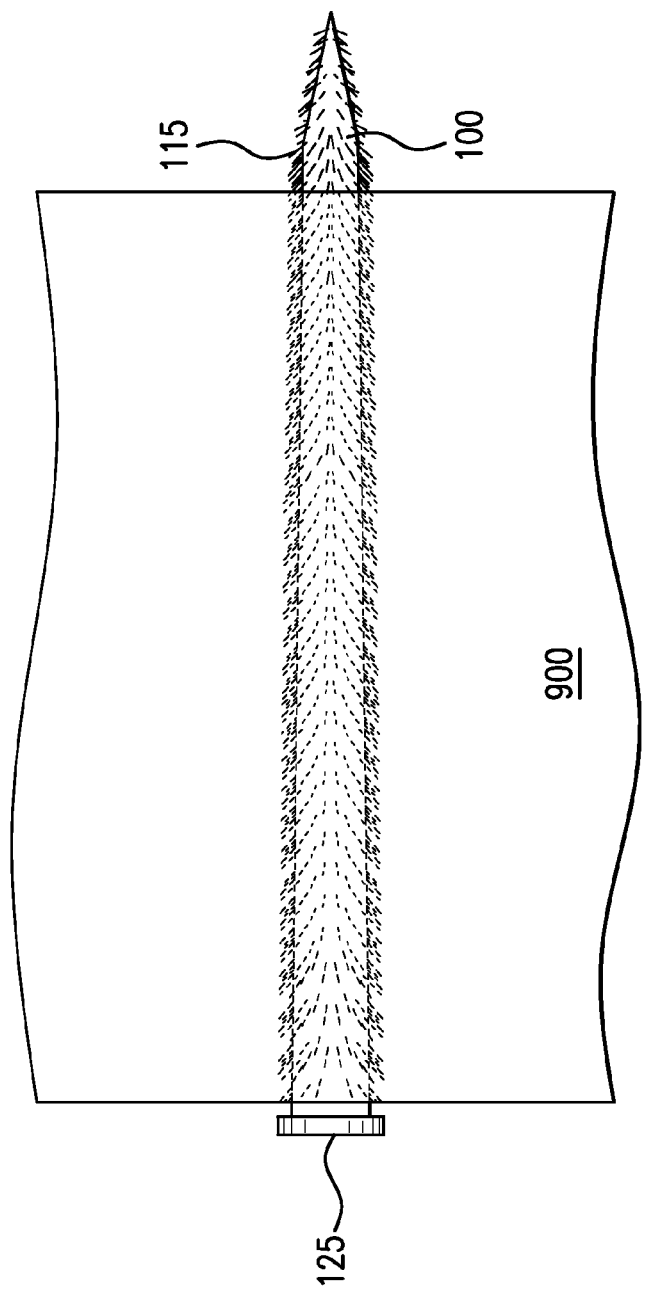

FIG. 14C shows a cross section of the tissue 900 and the extension of the fastener 100 through the thickness of the tissue 900. The fastener 100 is driven distally until the proximal head 125 contacts the outer surface of the tissue 900. Thus, further distal movement of the fastener 100 is resisted by the proximal head 125 while proximal movement is resisted by the proximally slanted orientation of the anchoring filaments 115.

During driving of the distal fastener 100, the tip 110 of the proximal fastener 100 extends into a recess 145 (shown, e.g., in FIG. 15A) in the proximal head 125 of the distal fastener 100. In order to prevent damage to the needle-like tip 110, the recess may be dimensioned so that the load-bearing contact between the proximal fastener 100 and the proximal head 125 of the distal fastener occurs at a location that is proximal to the tip 110 of the proximal fastener 100, e.g., an annular contact area at a location on the distal tapered portion of the proximal fastener 100 proximal or rearward of the more fragile tip 110. This may be accomplished, for example, by making the depth of the recess 145 sufficiently large with respect to the dimensions of the opening of the recess 145. Further, the edges of the opening may be rounded or chamfered to further reduce any chance of damage to the fasteners 100 during the driving operation. Other end-to-end fastener arrangement described herein may include analogous features.

Figure 15A:
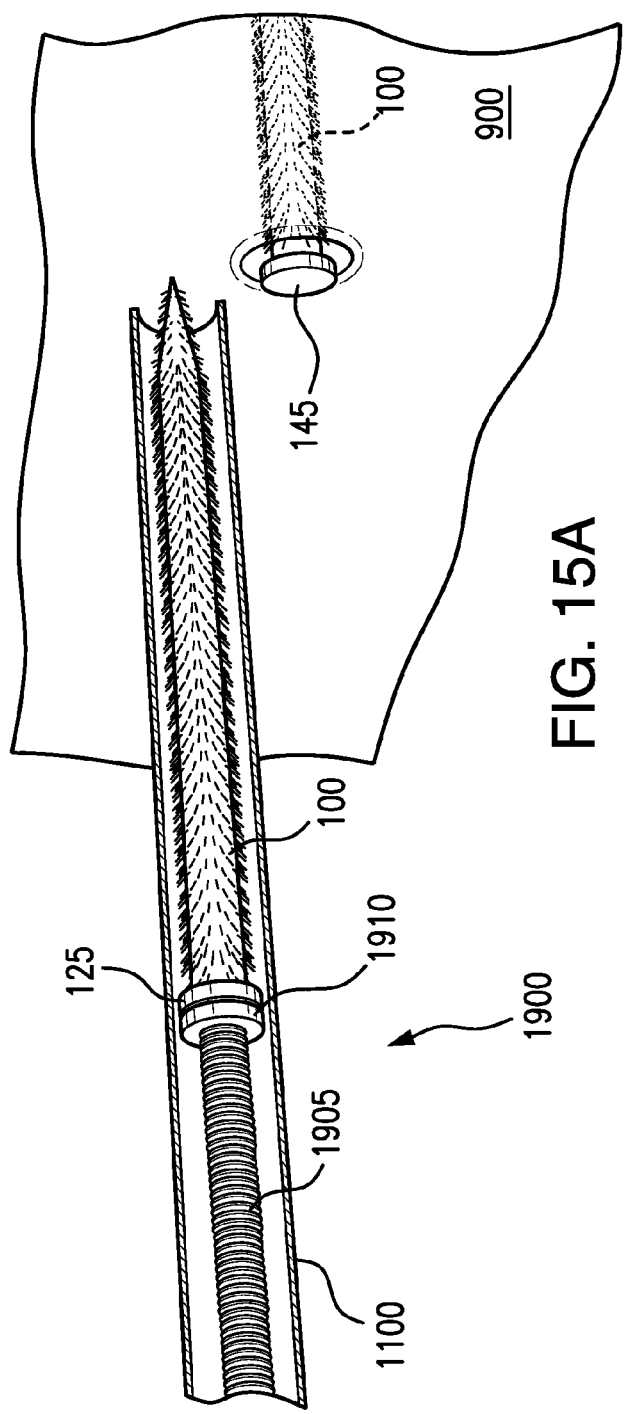
FIGS. 15A to 15C illustrate the driving of a second fastener into tissue.
Figure 15B:
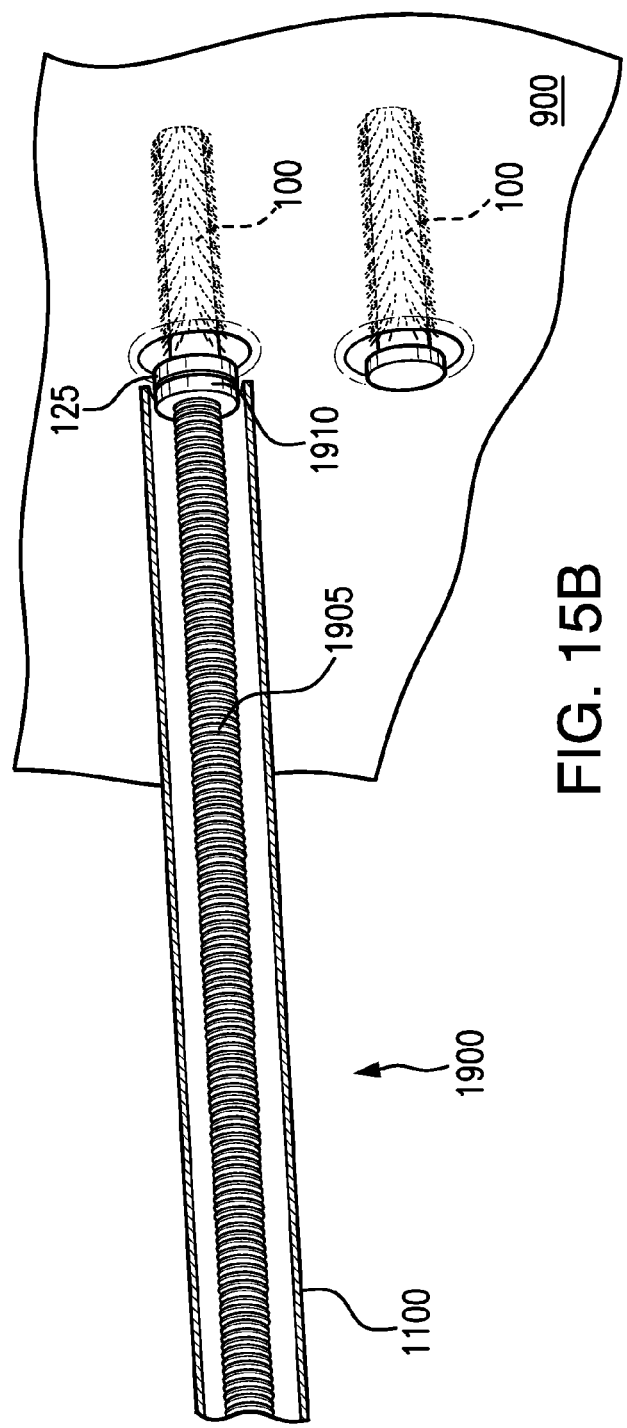
Figure 15C:
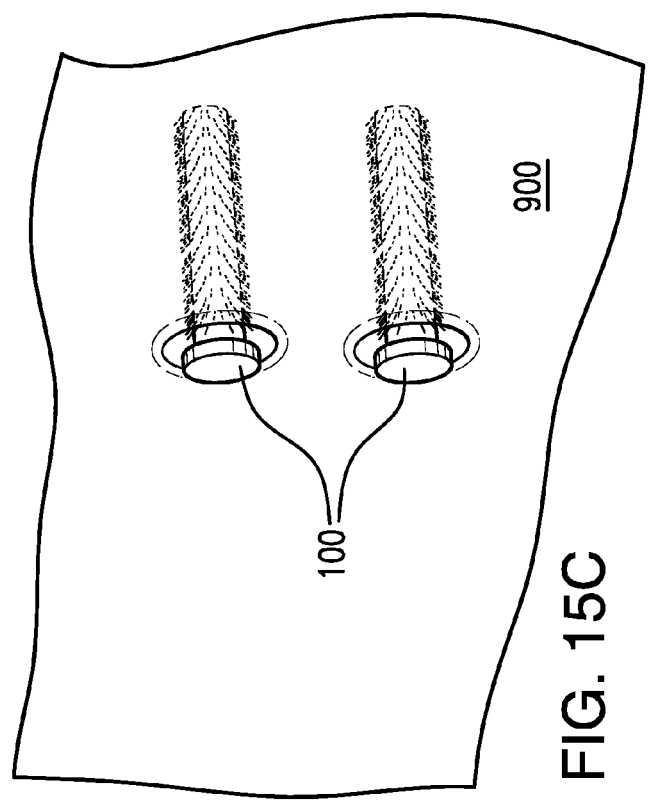
Figure 15C:
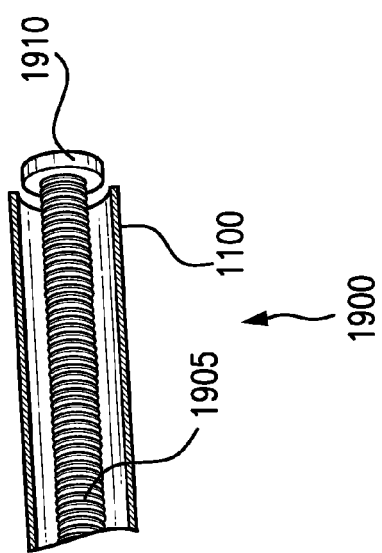

FIGS. 15A to 15C illustrate the repositioning of the fastening arm 1100 and the driving of the proximal fastener 100 into the tissue 900. The repositioning of the fastening arm 1100 may, for example, correspond to the repositioning illustrated sequentially between FIGS. 5B and 5C. Due to the distal movement during the driving of the distal fastener 100, the proximal fastener 100 is now in at the distal end of the fastening arm 1100, e.g., in the same, or substantially the same, position that the distal fastener 100 was in prior to its being driven.

Once repositioned as illustrated in FIG. 15A, the pushrod 1905 and the distal head 1910 are pushed forward, or distally, until the proximal fastener 100 is driven into the tissue 900 as illustrated in FIG. 15B. Once all of the fasteners 100 have been driven, the fastening arm 1100 is retracted, as illustrated in FIG. 15C.

It should be understood that although the fastening arm 1100 illustrated in FIGS. 13A to 15C houses and drives two fasteners 100, any number of fasteners 100, including a single fastener 100 or more than two fasteners 100 may be provided and driven in analogous manner to the driving described above.

Figure 16A:
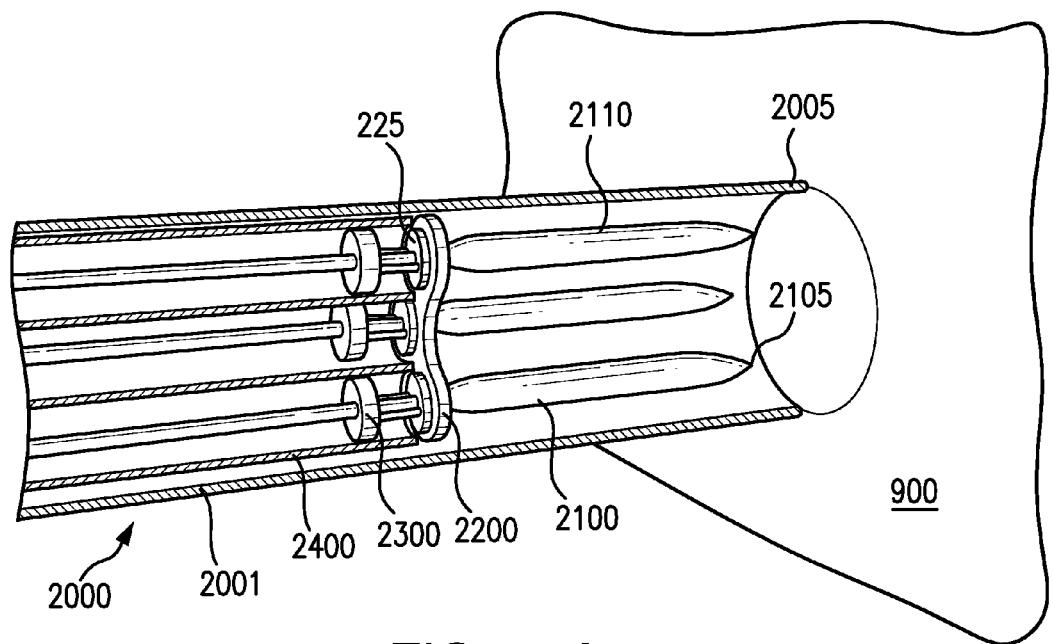
Figure 16B:
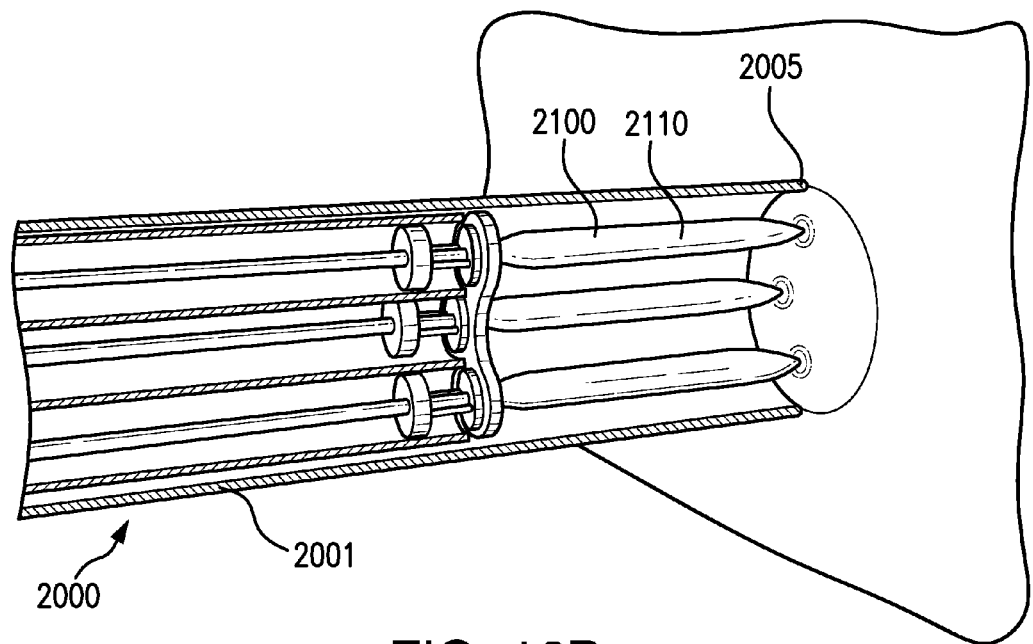

FIGS. 16A to 16C sequentially illustrate the insertion of implant-carrying needles or sleeves 2100 of a catheter or implanting device 2000 into tissue 900. As illustrated in FIG. 16A, the implanting device 2000 is maneuvered (e.g., via steering cables) to a position that is adjacent the tissue 900 to be repaired.

Each implant-carrying needle 2100 extends longitudinally through, in distal to proximal order, a plate or washer 2200, a respective head or nut 225 (described in greater detail below with regard to implant or fastener 200), and a respective nut driver 2300. Each implant-carrying needle 2100 also extends longitudinally into and along a respective sleeve or tube 2400, which is housed in the catheter or implanting device 2000. In the position illustrated in FIG. 16A all of these components are disposed in an interior space defined by housing 2001, which is, e.g., a catheter housing.

The needles 2100 may be formed, e.g., of a shape-memory material, e.g., nitinol or spring-loaded steel.

A distal portion 2110 of each needle 2100 houses an implant or fastener 200 (less the head or nut 225), which is described in greater detail below in connection with FIG. 20.

As illustrated in FIG. 16B, the implant-carrying needles 2100 are moved distally with respect to the housing 2001 and the tissue 900 until distal, needle-like tips 2105 extend beyond a distal end 2005 of the housing 2001 and contact and pierce the tissue 900. The pressure required to progress the needle may be sensed using any appropriate pressure sensing mechanism, the pressure being relayed to, e.g., a computer control system in a hand piece to which the implanting device is coupled. Further, imaging data may be obtained, including, e.g., ultrasound or other digital imaging mechanisms and relayed to, e.g., the computer control system in a hand piece. This information, including pressure and/or imaging information and/or any other sensed information may be used by the control system to appropriately control the insertion of the needles 2100 into the tissue. For example, the control system may control the rate, location, angle, and/or depth of insertion of each needle 2100 independently.

After further distal movement of the implant-carrying needles 2100, the needles 2100 reach a full or desired depth into the tissue 900, as illustrated in FIG. 16C. It is noted that, for additional clarity, each of FIGS. 16C to 18E includes an inset cross-sectional view of the tissue 900, each inset view corresponding in time and state to the conditions of other portions of the respective figure. As illustrated in FIG. 16C, each needle 2100 has penetrated and extended into and through a proximal layer 901 and a distal layer 902 of the tissue 900. It should be understood, however, that the distal layer 902 need not be fully penetrated, i.e., the distal layer 902 may be penetrated to a partial depth or less than through. The layers 901 and 902 of tissue 900 may correspond to any appropriate tissues suitable for repair. For example, the layers 901 and 902 may be portions 905 and 910 described above with respect to FIG. 1B.

After the needles 2100 have reached the desired depth illustrated in FIG. 16C, the needles 2100 are proximally retracted as sequentially illustrated in FIGS. 17A to 17D. As each sleeve or needle 2100 is retracted, the respective implant 200 (described in greater detail below), which was housed in the distal portion of the needle 2100 and carried into its inserted or driven position by the needle 2100, remains in the tissue 900. That is, the needles 2100 are retracted back into the housing 2001, but the implants 200 are not. Rather, they are left in their desired implanted position, with the distal portion with filaments 215 fully and effectively engaging and anchoring into the distal layer 902 of tissue 900, and the proximal, externally threaded portion extending proximally beyond the proximal layer 901 of tissue 900.

The implant 200 may be initially prevented from retracting toward the housing 2001 by any appropriate mechanism. For example, an interior shaft within the needle 2100 may initially create a positive stop against proximal movement of the implant 200 until a sufficient number of filaments 215 are able to engage the tissue of the second layer 902. Once enough filaments engage the layer 902, the implant 200 will maintain its position itself against proximal movement or retraction. Further, the needle 2100 may have openings, e.g., slits, that allow a substantial number of filaments 215 to contact the second layer 902 of tissue 900 prior to and during retraction of the needle 2100. Moreover, the needle 2100 may be configured such that the distal tip 210 forms the needle-like leading tip during the distal insertion, a number of filaments adjacent the tip 210 being exposed to the tissue during insertion and retraction of the needle 2100. Another mechanism may include proximally pulling the sleeve or needle 2100 through a hole (e.g., the interior of nut 225) with a diameter that is less than the diameter of the implant 200.

Figure 17A:
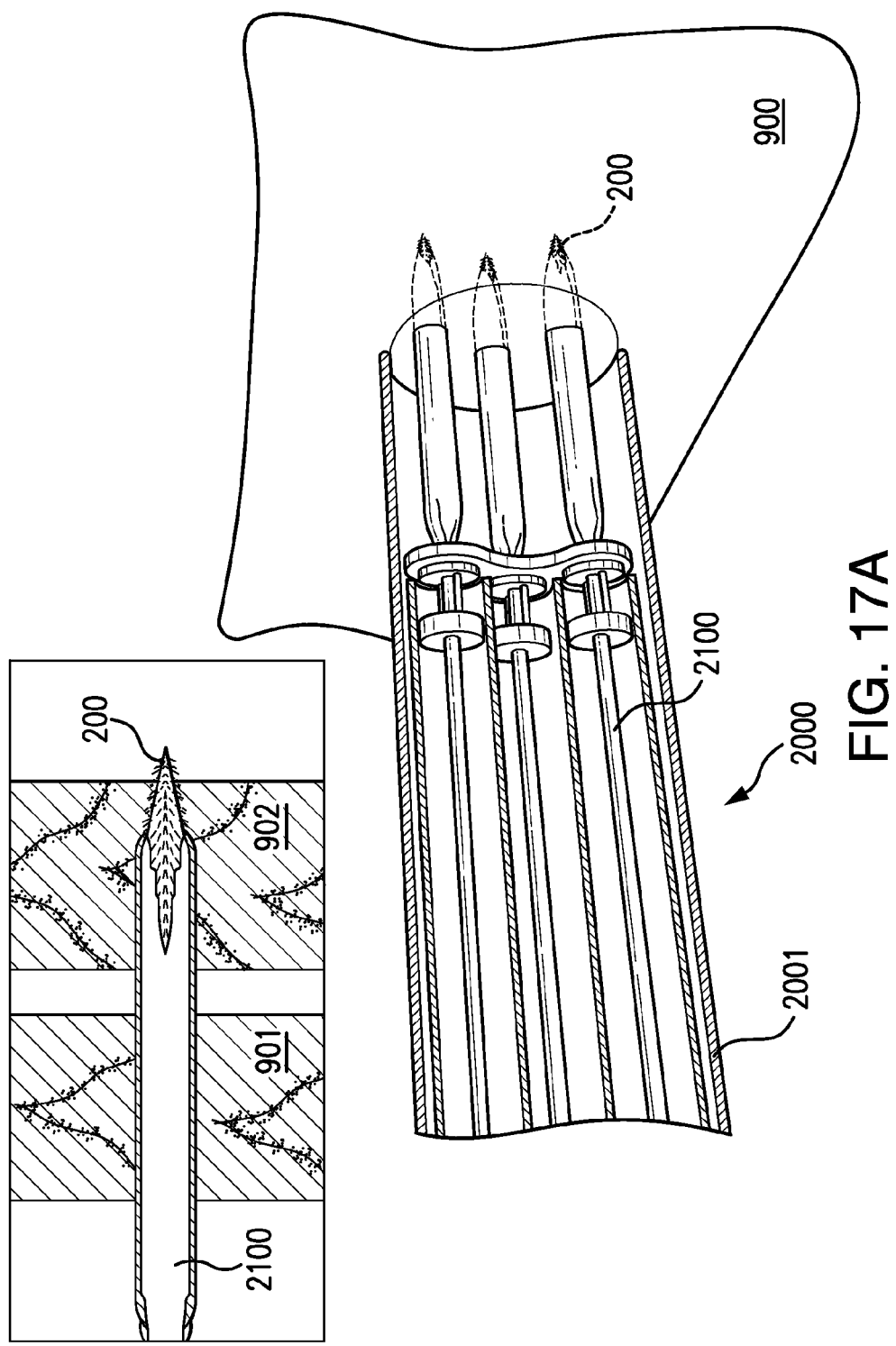
Figure 17B:
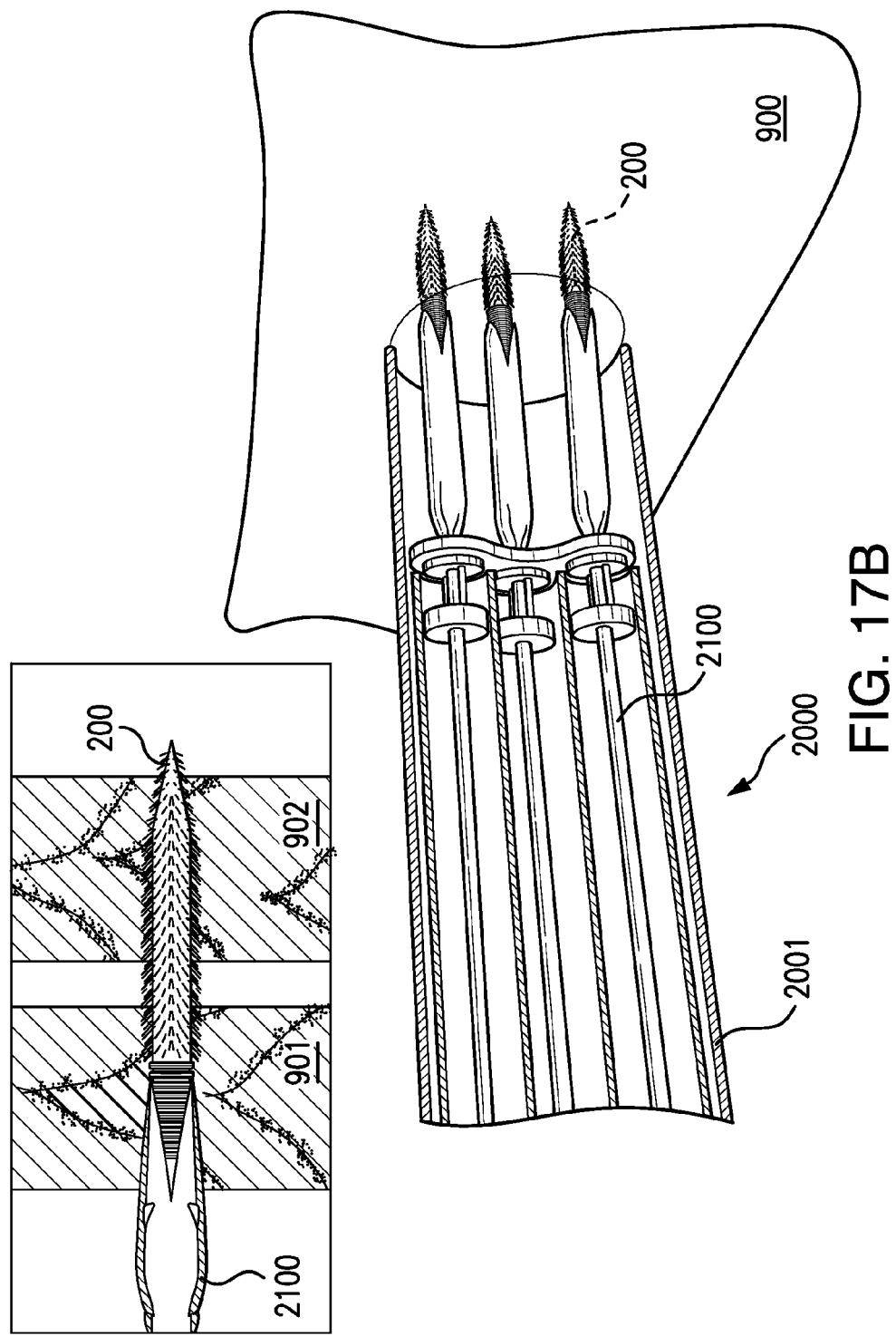
Figure 17D:
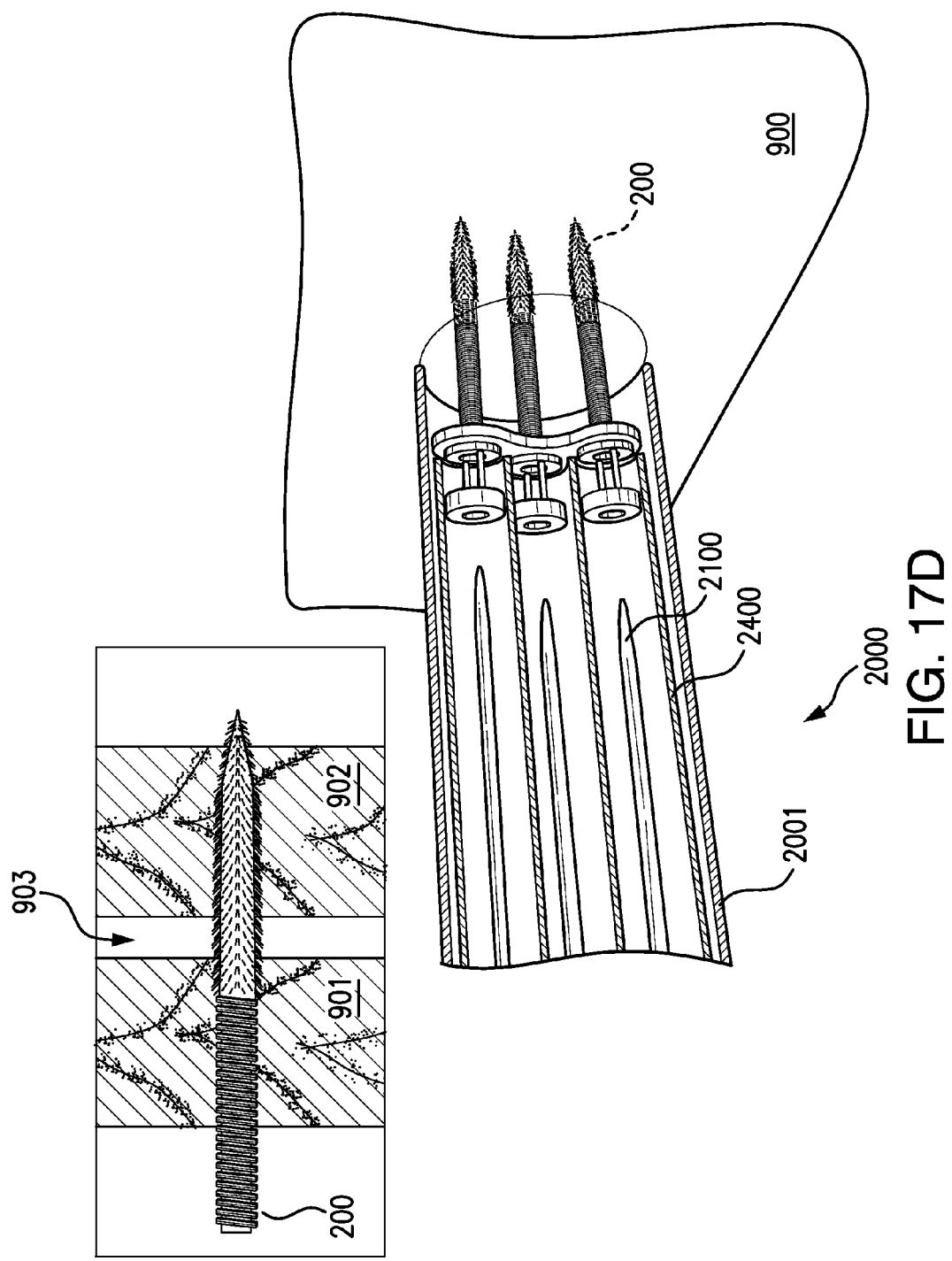

As illustrated, e.g., in FIG. 17D, a gap 903 remains between the two layers 901 and 902 of tissue 900. The gap 903 may be closed as set forth below.

Figure 18A:
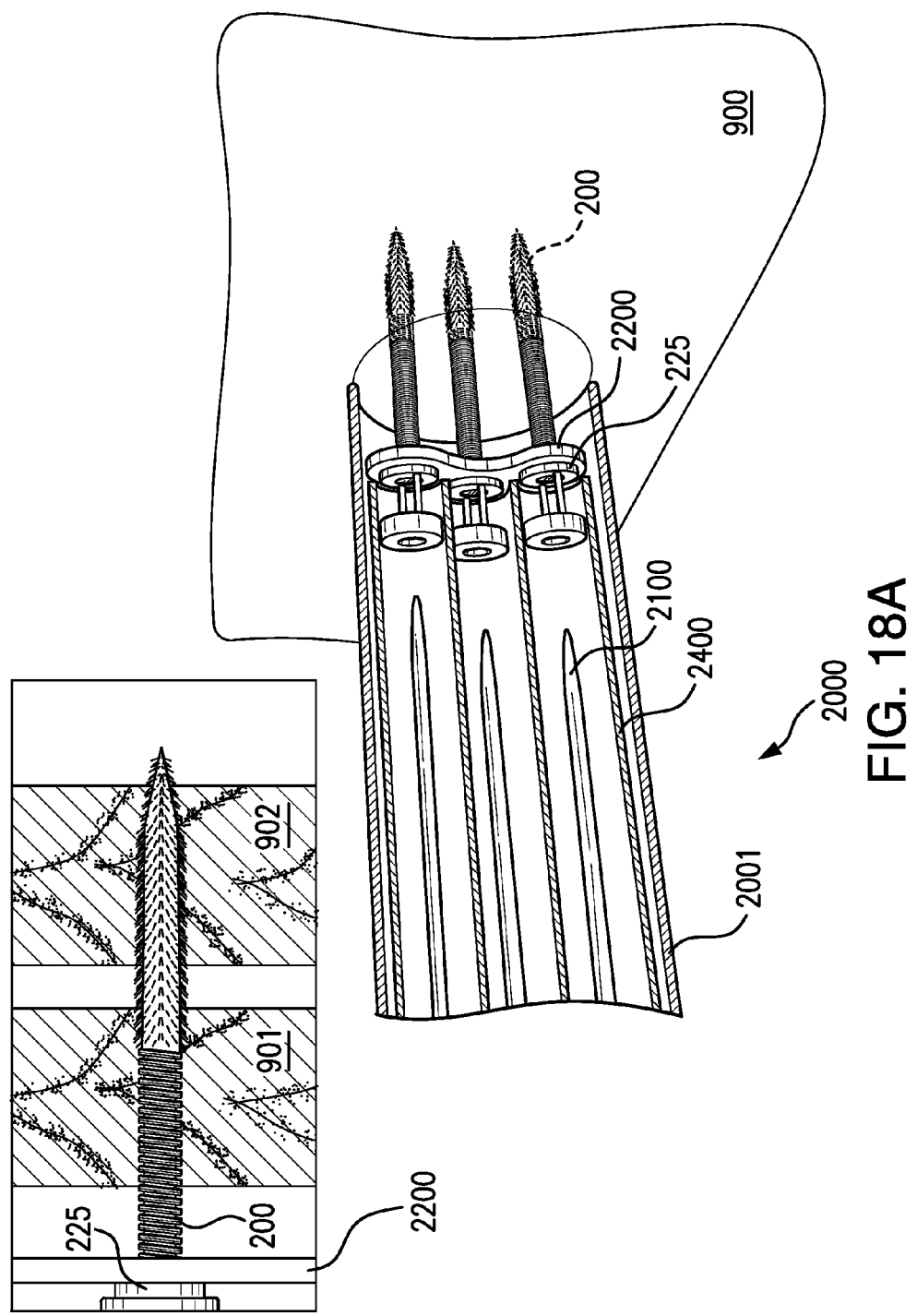
FIGS. 18A to 18G sequentially illustrate the attachment and fastening of an implant plate or washer to the previously inserted implants or fasteners.

After the needle or sleeve 2100 has been retracted, the tubes 2400 are moved distally within the housing 2001 until the externally threaded shafts, or proximal portions, of the implants or fasteners 2100 pass through an opening in the plate or washer 2200 to contact the respective internally threaded nuts 225, as illustrated in FIG. 18A. Once the nuts 225 and implants 200 are in contact, the nut drivers 2300, which are mounted in respective tubes 2400, are rotated to impart rotation to the nuts 225, thereby rotatably engaging the internal threads of the nuts 225 with the external threads of the respective proximal portions of the implants 200. In order to rotate the nuts 225, each nut driver 2300 includes a pair of distally extending driving pins 2305 that extend into and engage a corresponding pair of recesses 227 (see, e.g., FIG. 1) of the respective nut 225. The nut drivers 2300 may be independently driven by, e.g., rotation of respective tubes 2400 in which the nut drivers 2300 are mounted. The rotation may be computer-controlled and/or individualized for each nut based on, e.g., torque feedback, pressure feedback, imaging data or other feedback data.

Figure 18B:
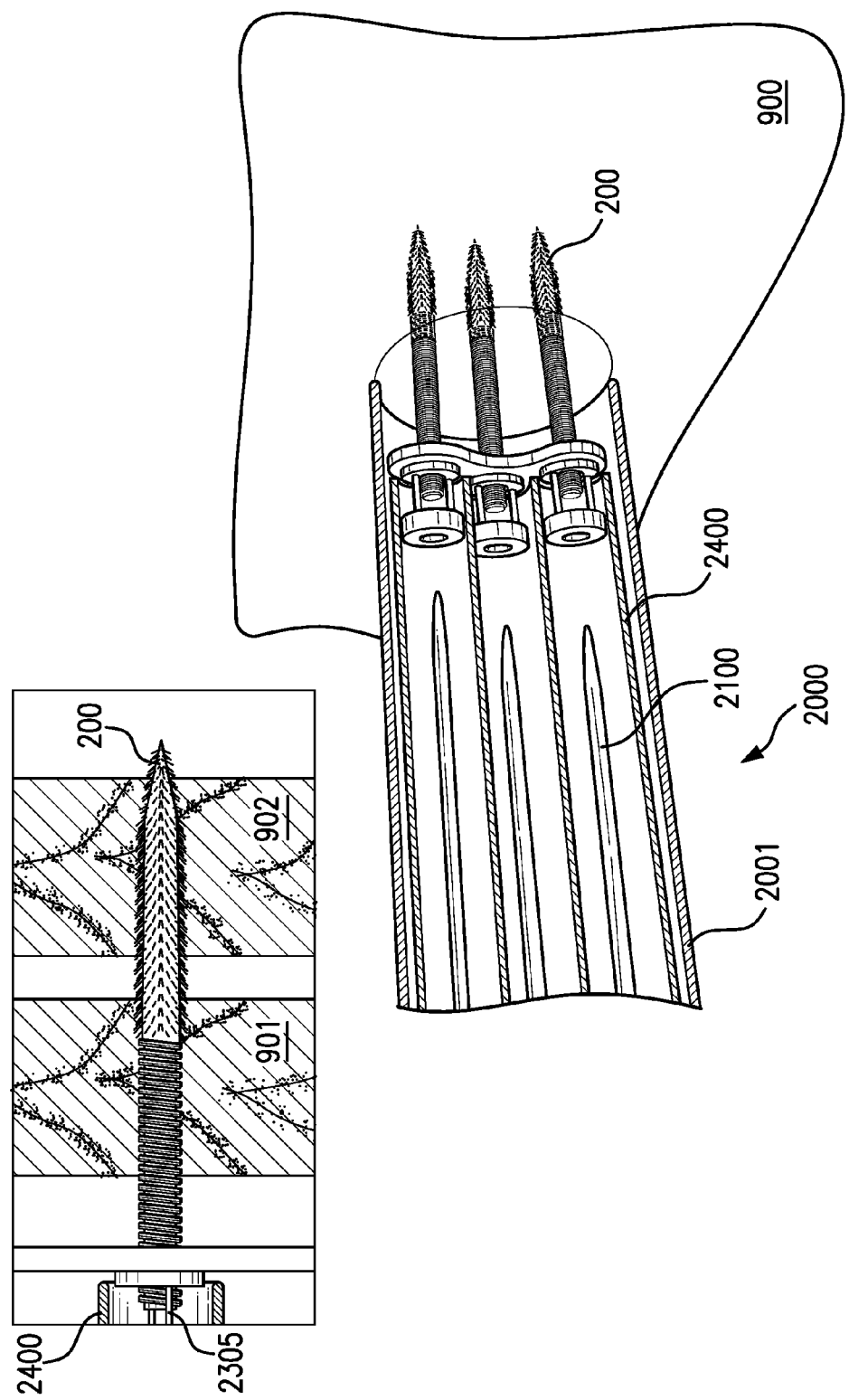
Figure 18C:
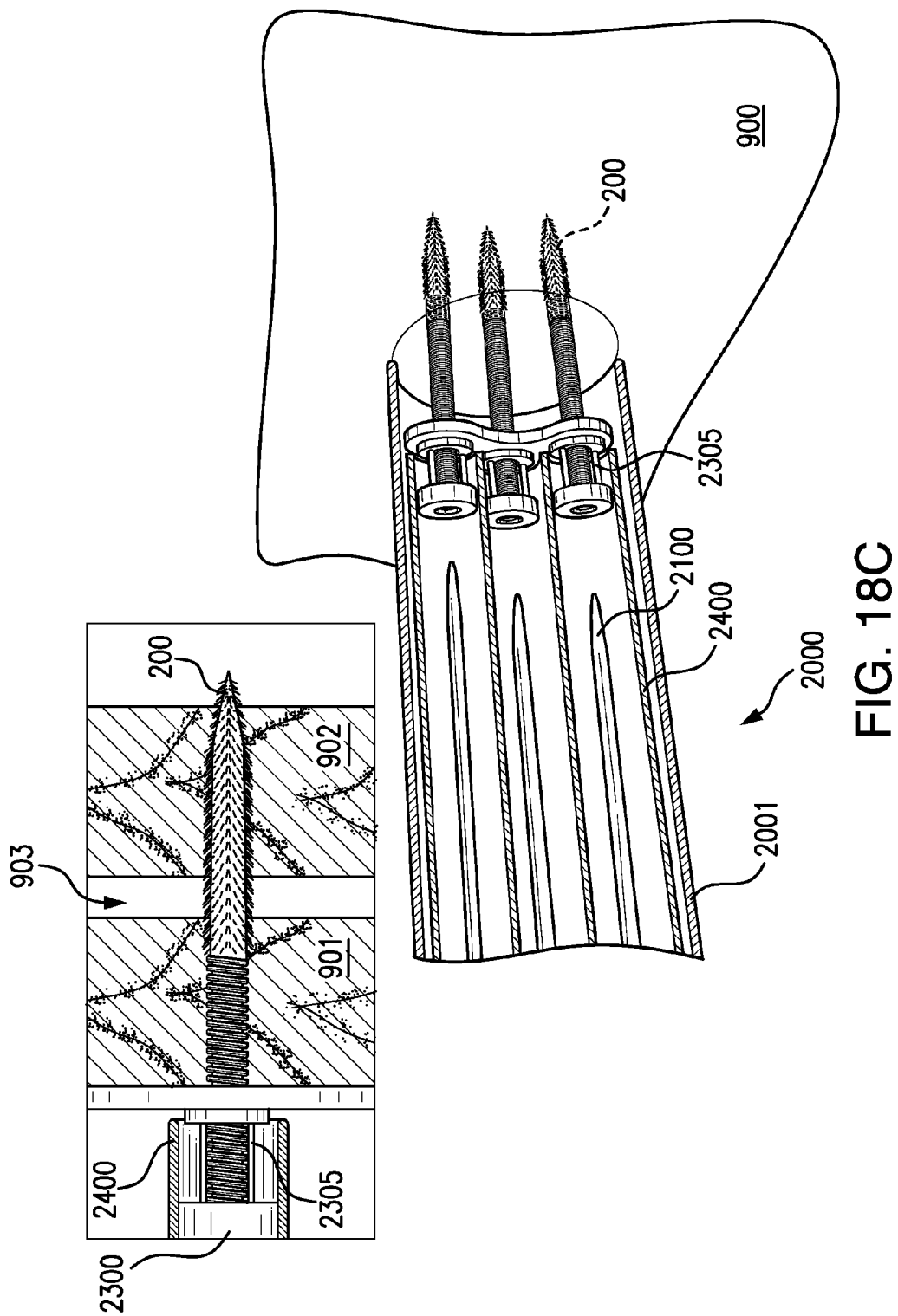
Figure 18D:
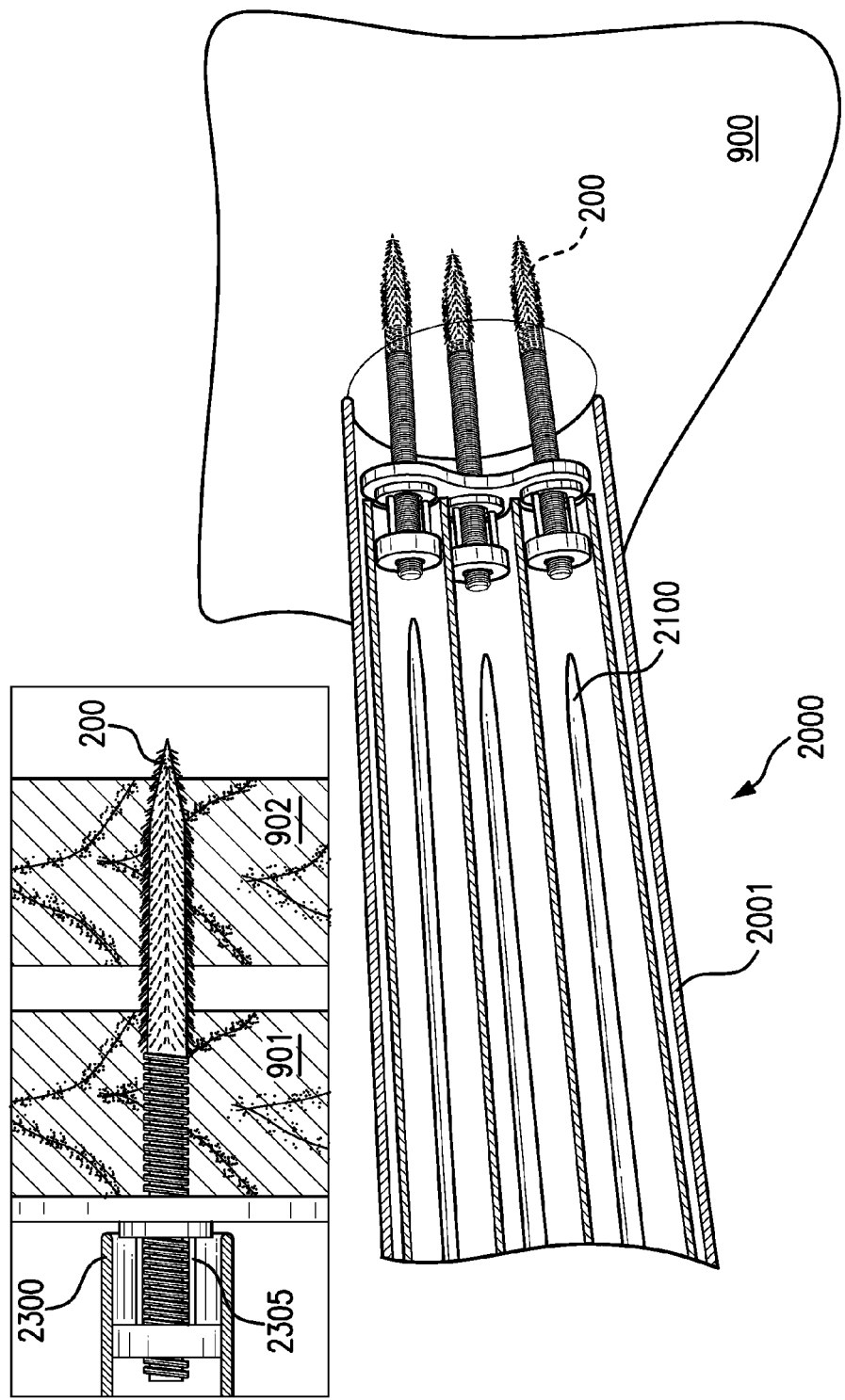
Figure 18E:
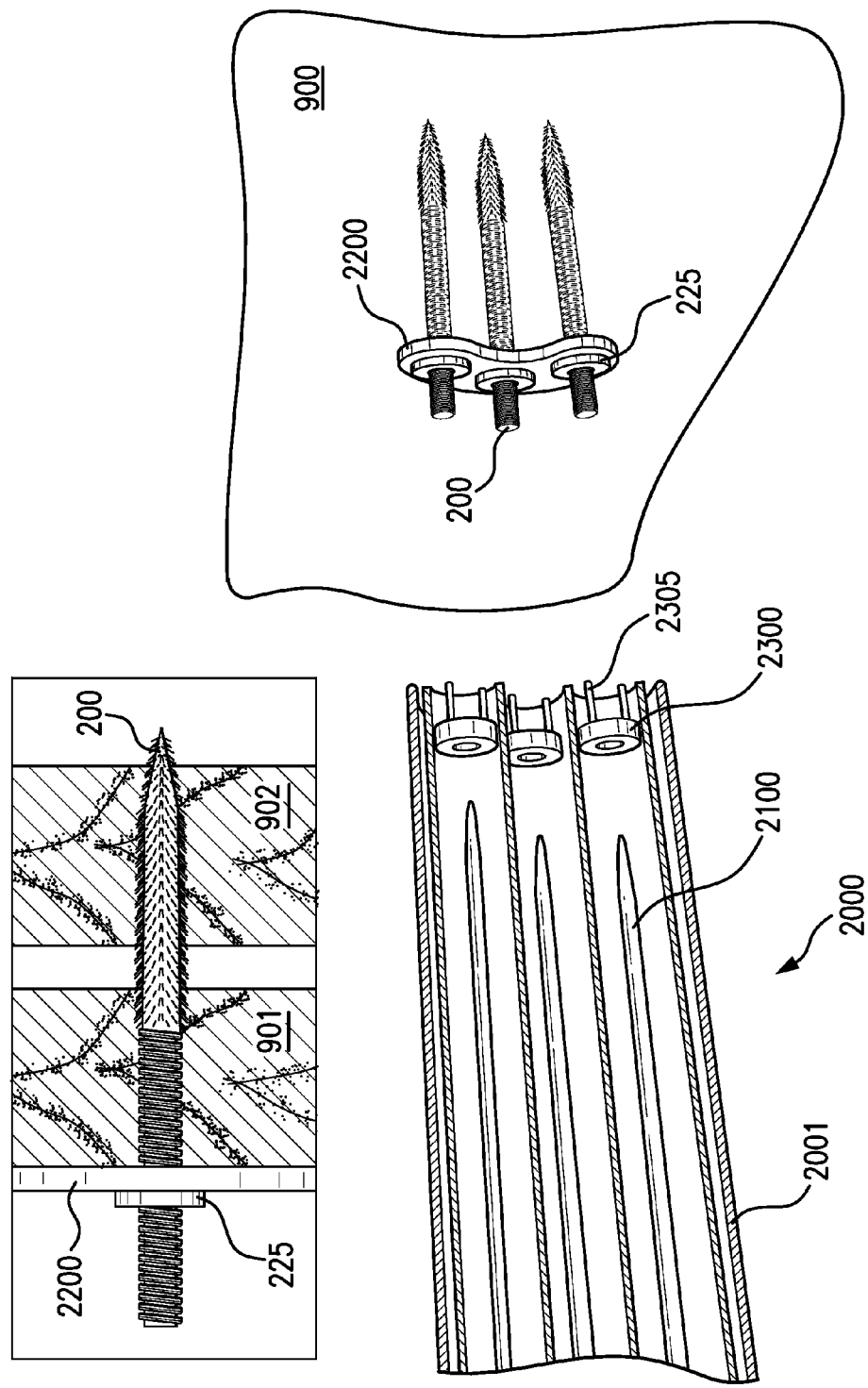

Further rotation of the nuts 225 about the respective externally threaded portions of the implants 200 causes the nuts 225 to travel distally along the length of the nut 225, as illustrated in FIGS. 18B and 18C. Since each nut 225 is larger than the opening of the plate or washer 2200 through which the respective shafts of the implants 200 pass, the distal movement of the nuts 225 causes the plate 2200 to move distally as well. As illustrated in FIG. 18C, the distal movement of the plate 2200 eventually causes the plate 2200 to contact the proximal surface of the proximal layer 901 of tissue 900. Further distal movement of the nuts 225 and the plate 2200 causes the first layer of tissue, due to contact with the plate 2200, to also move distally along the shafts of the implants 200. As such, since the distal layer of tissue 902 is engaged by the proximally slanted filaments 215, the proximal and distal layers 201 and 202 of tissue 900 are drawn together, thereby eliminating the gap 903 therebetween, as illustrated in FIGS. 18D and 18E. As illustrated in FIG. 18E, the implanting device 2000 is retracted from the implant site. The remaining portions, including implant 200, nut 225, and plate 2200 may be formed entirely of one or more bioabsorbable materials. It should be understood, however, that one or more, or all of these components may be formed of non-absorbable materials.

Although three implants 200 are applied in the illustrated example, it should be understood that any appropriate number of implants 200 may be provided to support the plate, including a single implant 200. Moreover, although the plate 2200 has a curved shape, it should be understood that the plate 2200 may be of any appropriate shape and/or size, depending, e.g., on the particular application.

Figure 18F:
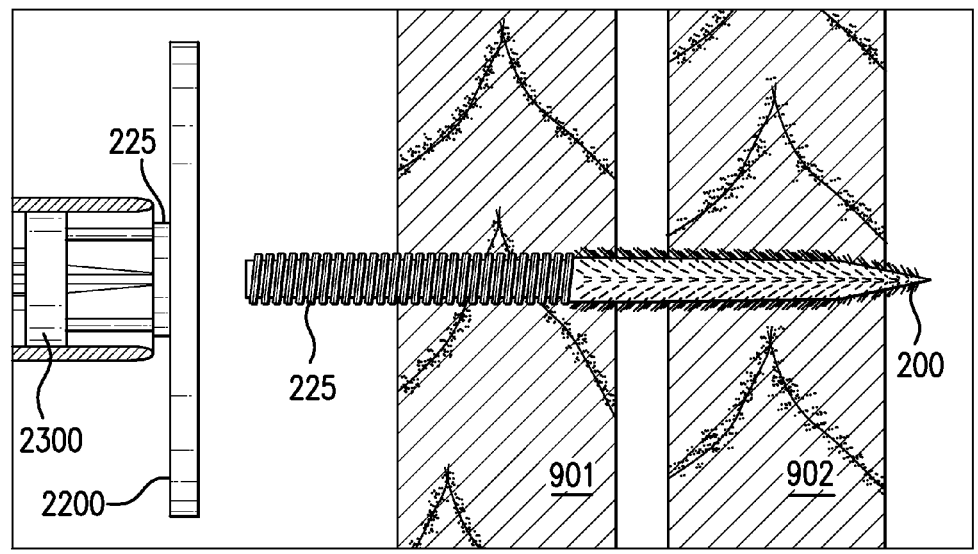

FIG. 18F shows the two layers of tissue, i.e., the primum 901 and secundum 902, prior to being drawn together by tightening of the micro tightening nut 225. As illustrated, the micro tightening filaments of the micro implant are engaged with the secundum such that the tightening down of the nut 225 causes the primum 901 and secundum 902 to be pulled together.

The needles 2100 may be formed in any suitable way. For example, the needles may be formed by making longitudinally extending cuts in a nitinol tube, e.g., by laser cutting. The cuts may extend, e.g., all the way to the proximal ends of the needles 2100 or stop short of the ends. In this regard, length and/or number of the cuts may be selected to determine the amount of radially directed spring force exerted by the metal bands between the cuts.

Figure 18G:
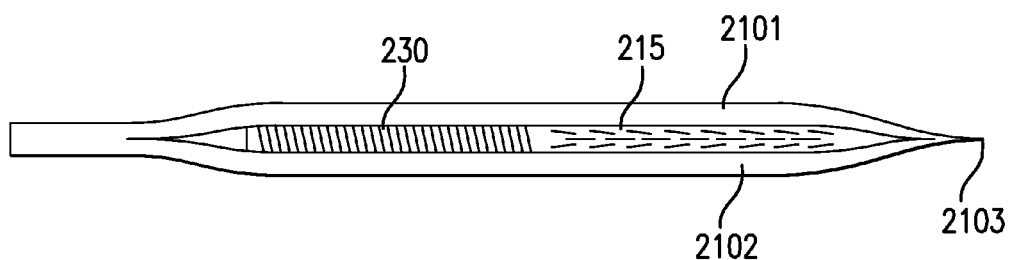

Further, it may be desirable to form the needles 2100 to have a smaller resting or initial diameter than the fastener contained therein. For example, referring to FIG. 18G, a needle 2101, which otherwise shares features in common with needle 2100, has a smaller resting or initial diameter than the fastener 200. Thus, when the fastener 200 is inserted into the needle 2101 as illustrated in FIG. 18G, the metal bands 2102 bulge outwardly to form expanded gaps between the adjacent metal bands 2102. This may be advantageous to allow the filaments and/or other anchoring mechanism(s) to engage the adjacent tissue and resist proximal movement of the fastener as the needle 2101 is retracted. For example, as illustrated in FIG. 18G, the micro anchoring filaments 215 of the fastener 200 are exposed through the longitudinally extending gap between adjacent bands 2102 of the needle 2101, thus allowing the filaments 215 to engage surrounding tissue even at the initial stages of the retraction of the needle 2101. In this regard, the engagement of the filaments 215 with the tissue may be sufficient in and of itself to allow proximal refraction of the needle 2101 while leaving the fastener 200 in its implanted position. It should be understood, however, that other mechanisms, e.g, a push rod, may be provided in connection with the needle 2101.

The needle implantation method may be employed in other applications, e.g., to fasten the mesh 1300 as set forth above. For example, one or more or all of the arms 1100 may be provided with a needle 2100, 2101 to implant the fasteners 1400 in the same or analogous manner described above with regard to FIGS. 16A to 17D.

Figure 19A:
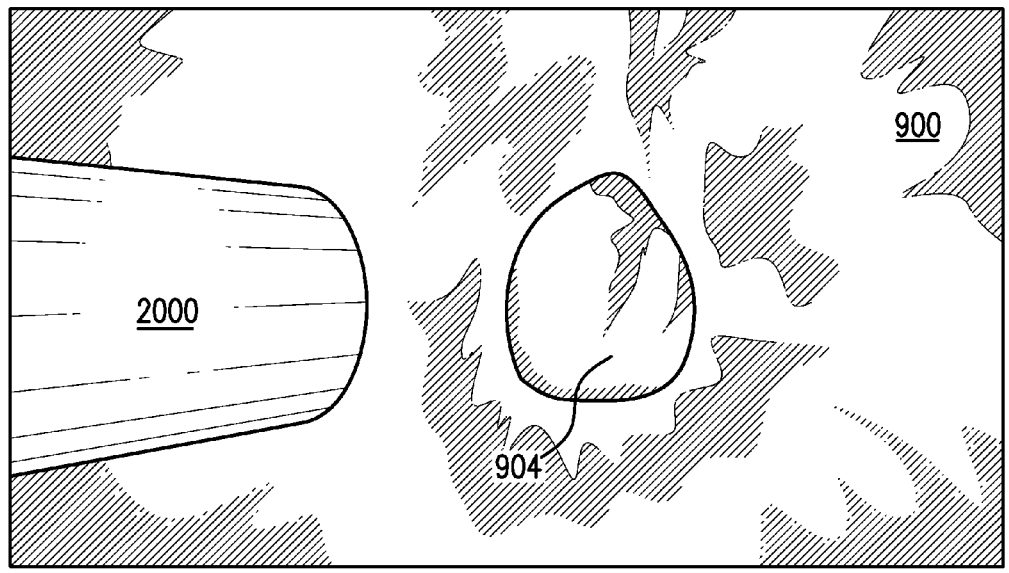
FIGS. 19A to 19D sequentially illustrate the use of the implanting device to repair a tissue defect.
Figure 19B:
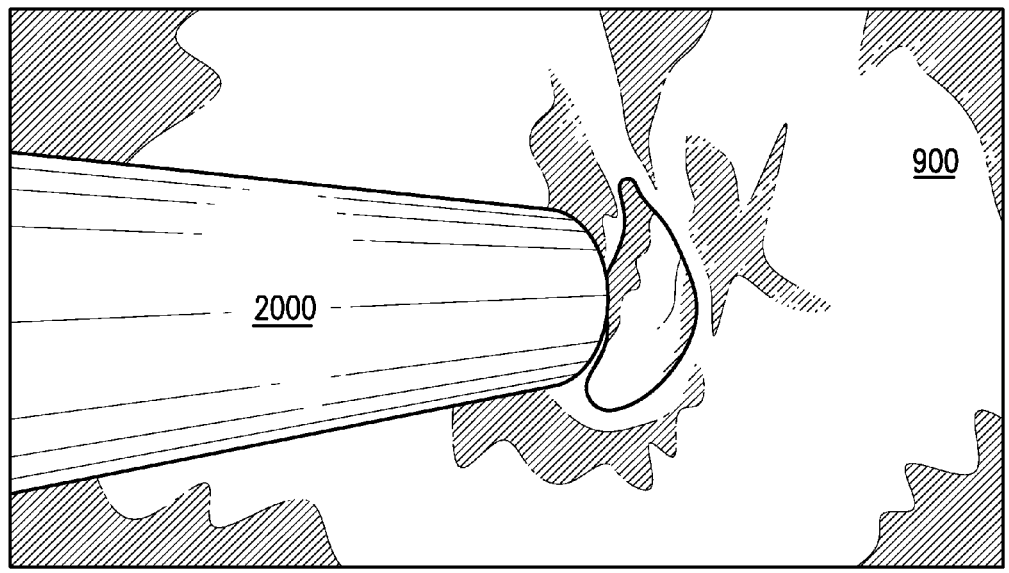
Figure 19C:
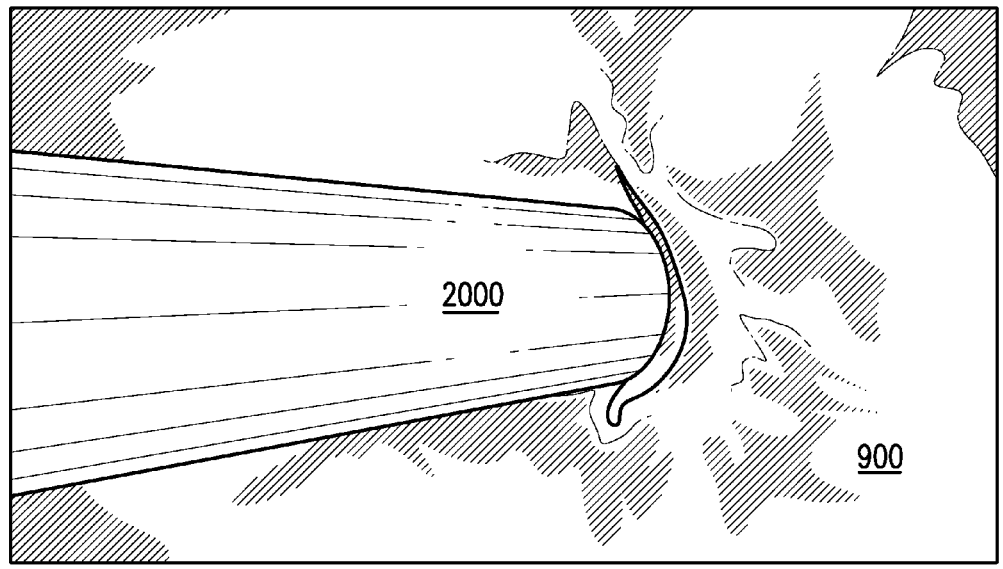
Figure 19D:
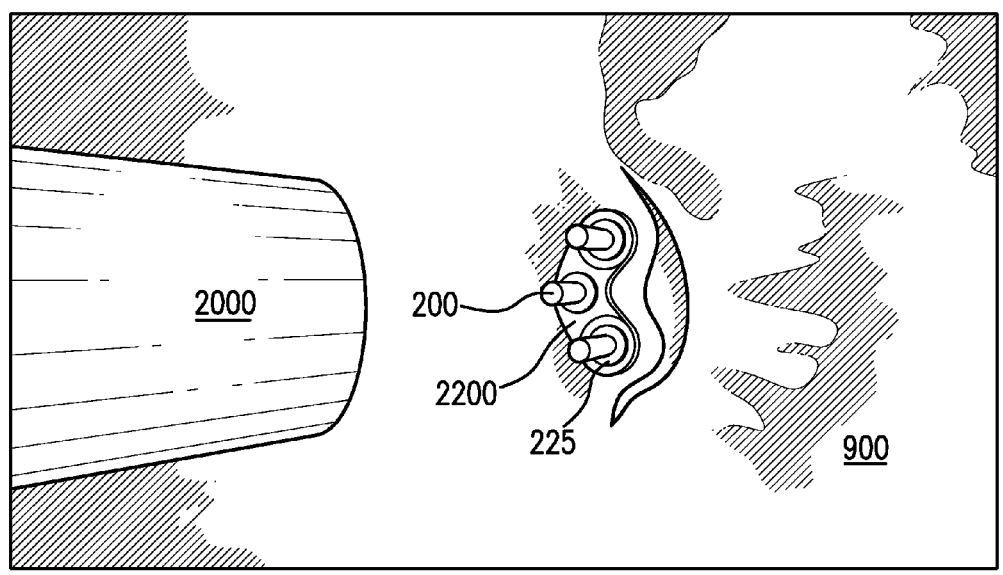

FIGS. 19A to 19D sequentially illustrate the above procedure to repair a defect 904 in tissue 900. As illustrated in FIG. 19B, the implanting device 2000 is maneuvered into proximity of the defect 904. As illustrated in FIG. 19C a flap of tissue 900 is pushed into position and fastened in the manner set forth above, with the flap of tissue 900 corresponding to the first or proximal layer 901 of tissue 900 and the underlying tissue 900 corresponding to the second or distal layer 902 of tissue 900 described above. As illustrated in FIG. 19D, the implanting device 2000 is retracted leaving the plate 2200, fasteners 200, and nuts/heads 225 in place to secure the tissue 900 in the repaired condition. It is noted that the plate 2200 allows for the force exerted by fasteners 200 on the proximal layer of tissue to be dispersed over a relatively large area, thereby reducing any risk of tissue tearing at fastener locations.

FIG. 20 is an illustration of two surgical micro implants or fasteners 100 and 200, which may be used as any of the fasteners disclosed herein, e.g., the fastener or implants 1400 and 1500. As set described in greater detail above, the fastener 100 is also illustrated and described in connection with FIGS. 13A to 15C and the fastener 200 is also illustrated and described in connection with FIGS. 16A to 19D. The surgical implants 100 and 200, which may be absorbable or non-absorbable, are designed to penetrate and join two adjacent viscera or tissue planes. The implants 100 and 200 are designed to pass through the first tissue and the second tissue under controlled rapid deployment. The implant is shaped similarly to a needle with a predetermined geometry. Each implant 100, 200 has an elongated body 105, 205 that tapers in a distal region to a needle-like tip 110, 210. Each implant 100, 200 may be deployed, as described in greater detail below, by being pushed from a precisely placed hollow needle or tube containing the implant 100, 200.

The micro implants 100 and 200, as well as any other fasteners disclosed herein may have a diameter of one millimeter, or approximately one millimeter, and a length that is in a range from 5 millimeters to 10 millimeters. According to some example embodiments, the diameter is less than one millimeter. According to some example embodiments, the diameter is in a range from 0.8 millimeters to 1.2 millimeters. It should be understood, however, that other dimensions may be provided.

The body 105, 205 of each implant 100, 200 has specifically designed micro anchoring filaments 115, 215 which arise from a core 120, 220 of the implant 100, 200 to extend outwardly from the core 120, 220. The anchoring filaments 115, 215 are located around the circumference and along at least a portion of the length of the body 105, 205 of the implant 100, 200. This allows the implant to resist removal once it has penetrated the tissue.

The core 120, 220 has a constant diameter along a substantial length of the body 105, 205 of the implant 100, 200. For example, the core 120 of the implant 100 has a constant cross-section, and constant diameter, from a head portion 125 to a substantially conically shaped tapered portion toward the tip 110. It should be understood however, that the implants 100 and 200 may have a more continuous taper and/or have a constant or non-constant rate of taper.

The anchoring filaments 115, 215 extend outwardly at an angle with respect to the longitudinal axis of the implant 100, 200. In this regard, the filaments, in addition to extending outwardly away from the longitudinal axis, also extend in a proximal direction, away from the tip 110, 210. This allows for the filaments 115, 215 to slide along the pierced tissue during distal driving or insertion. However, proximal movement of the implants 100, 200 from the inserted position is prevented or resisted by engagement of the outer, free ends of the filaments 115, 215 with the relatively soft tissue. The filaments 115, 215 may be flexible or substantially rigid. The filaments 115, 215 should, however, have sufficient stiffness or strength to resist proximal withdrawal of the implant 100, 200 from the inserted position. Further, although the filaments 115, 215 are illustrated as being straight, it should be understood that some or all of the filaments 115, 215 may be at least partially curved, and/or have one or more bends between straight portions and/or curved portions. Moreover, the filaments 115, 215 of a given implant 100, 200 may have constant or differing lengths, radial extensions, and/or angles with respect to the longitudinal axis of the implant 100, 200.

The filaments 115, 215, or any other anchoring filaments described herein may be provided with any appropriate density and relative spacing, depending on the particular application. For a given application, a greater density (i.e., a greater number of filaments per unit of surface area) of smaller filaments may be provided, or a lesser density of larger filaments (optionally reinforced with a shape memory alloy, e.g., nitinol and/or spring-loaded steel), while presenting the same or comparable suture retention or "pull through strength." The optional reinforcement could be a "V" shaped portion formed of shape memory alloy, e.g, nitinol and/or spring-loaded steel. The filaments 115, 215 may be absorbable or non-absorbable in whole or in part.

Each implant 100, 200 includes a proximal head 125, 225. The head 125, 225 extends radially beyond the core 120, 220 and has a larger axial cross section than the core 120, 220. The head 125, 225 may prevent the implant 100 from being driven too deeply into, or entirely through, the tissue. As the implant 100, 200 is driven distally along its longitudinal axis, the core 120, 220 pierces into and progresses through the tissue. The head 125, 225, having a larger diameter or cross section, prevents or resists the proximal portion of the implant 100, 200 from extending into the tissue. Thus, where two layers of tissue are pierced and joined, the distal layer of tissue is constrained against distal movement away from the proximal layer of tissue by engagement of the distal layer with the filaments 115, 215, and the proximal layer is constrained against proximal movement away from the distal layer by engagement of the proximal layer (e.g., the outer proximal surface of the proximal layer) with the head 125, 225.

The implant 100 differs from the implant 200 in that the implant 100 has anchoring filaments 115 provided from the tip region to an axially fixed, proximal head 125, whereas the implant 200 has a predetermined length that is externally threaded with micro threads 230 to allow the head 225, which has corresponding internal threads, to rotate about the implant, thus bringing the two adjacent tissues into approximation. In this regard, the implant 200 may be initially driven into the tissue, the distance to which is driven being limited by, e.g., friction between the implant 200 and the tissue. After the initial driving, the head 225 may be rotated, e.g., in a clockwise direction, to move the head or nut 225 distally along the longitudinal axis of the implant 200. The rotation may be performed by a rotatable driver having projections configured to engage driving recesses 227 of the head 225, as described in greater detail below. Although the head 225 has four evenly spaced recesses 227, it should be understood that any appropriate number of recesses 227 may be provided. Further, the micro tightening nut or head 225 may have projections as an alternative or in addition to the recesses, the projections engageable by the driver to rotate the head 225. Moreover, any other appropriate driving mechanism may be provided. For example, the driver may grip the outer surface of the head 225 to impart rotation via friction, or the radially outwardly facing surface of the head 225 may have one or more flat surfaces engageable by the driver.

Contact between the distal face of the head 225 and the proximal surface of the proximal layer of tissue would in turn cause the proximal layer of tissue to move toward the distal layer of tissue, which is axially constrained by the filaments 215. The head 225 may be prevented from rotating in the opposition direction by friction between the threads or any appropriate locking or securing mechanism, e.g., detents. During the tightening rotation of the head 225, the body 205 may be prevented from rotating by the engagement of the filaments 215 with the tissue or any other appropriate mechanism.

Each implant 100, 200 has a proximal surface 135, 235 via which a driving force may be applied. The proximal surface 135 of the implant 100 corresponds to the proximal surface of the proximal head 125, while the proximal surface 235 of the implant 200 has a smaller diameter, which is the same or substantially the same as the diameter of the core 220.

Although the implants 100, 200 have cores 120, 220 and heads 125, 225 with circular cross sections, it should be understood that other cross-sections may be provided, e.g., rectangular, triangular, oval, polygonal, and/or any other regular or irregular shape. Further, it should be understood that the anchoring filaments 115, 215 may be evenly spaced apart or may have non-uniform spacing. Moreover, the filament density, i.e., the number of the filaments 115, 215 per unit of surface area of the core 120, 220 may be constant, or may vary.

Modern manufacturing processes allow for near nano technology applications. This allows the implants 100, 200 to be manufactured in a size and complexity that may not have been possible in years past. The implant 100, 200 may be injection molded of either absorbable or non absorbable polymers and then processed to add the features of the protruding filaments 115, 215 and the threaded features 227. The head 225 of the implant 200 is manufactured separately and to the same or similar tolerances so that the interface between the implant threads 230 and the head 225 of the implant 200 will thread precisely upon one another.

Although the implants 100 and 200 are formed of polymer, it should be appreciated that any appropriate material may used, e.g., metal or a composite material.

The materials and methods of manufacturing the implants 100 and 200 are applicable to any of the implants described herein.

In order to accurately penetrate adjacent tissues that are not held or secured on a distal side, a rapid penetration of each layer of tissue may be required in order to affect penetration of both tissue layers. If an implant 100, 200 is applied slowly, the tissue may be pushed distally away by the implant and/or needle without adequate penetration. Thus, some example delivery mechanisms eject the implant a relatively high velocity. In some preferred examples, saline or another suitable hydraulic is used to pressurize the channel within the catheter or needle at such a rate that the plunger will eject the implant at the precise velocity. Other example embodiments utilize a spring-loaded mechanical mechanism to eject the implant. Further example embodiments push the implant using long push rods which run the length of the catheter. The ejection modality is computer-controlled. However, it should be understood that the ejection may be, e.g., operator-controlled. For example, the ejection force may be predetermined and repeatable by a mechanical system, e.g., a spring-loaded system, which is triggered by an operator, e.g., a surgeon.

Figure 21A:
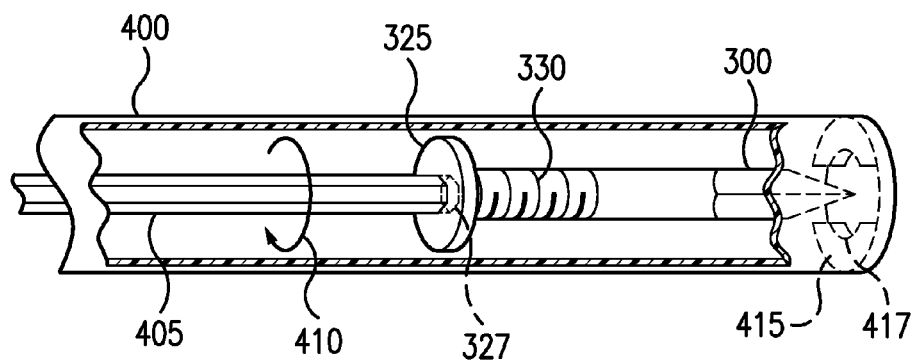
FIGS. 21A and 21B are illustrations of surgical implants with driving mechanisms.
Figure 21B:
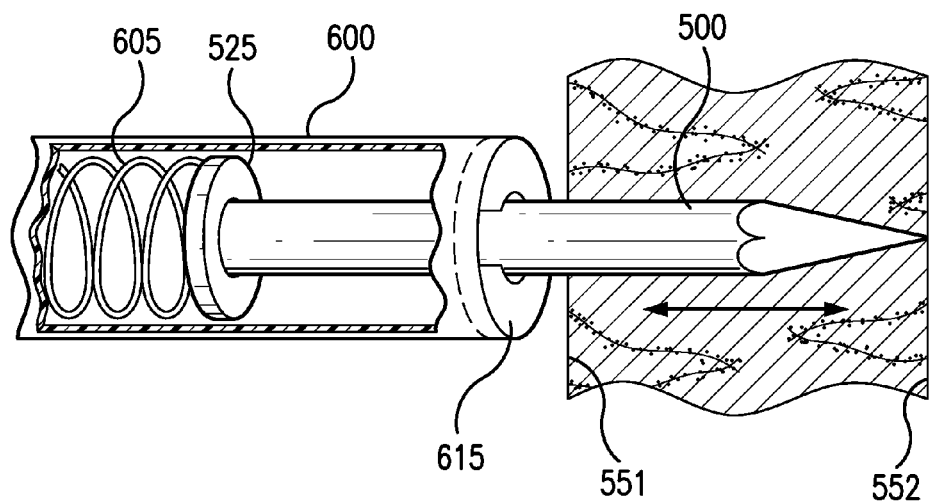

FIGS. 21A and 21B are schematic illustrations of surgical implants 300 and 500 with driving mechanisms including catheters or needles 400 and 600. These arrangements may be provided in connection with any of the fastener driving disclosed herein.

Referring to FIG. 21A, implant 300 shares many features in common with implants 100 and 200. Implant 300 differs, however, in that it includes reverse threads 330 and a proximal head 325 having a driving recess 327. The driving recess has a geometry that corresponds to a rotatable driver 405 of the catheter 400, such that the driver 405 is insertable into the recess 327 to impart axial rotation to the implant 300. In this regard, rotation of the driver in a first direction 410 causes the driver to rotate in the direction 410. Although the direction 410 is clockwise (when view from a proximal location), it should be appreciated that the driver may be configured to rotate the implant 300 in the counter-clockwise direction, e.g., where the threading is reversed. The driver is configured to progressively move distally along its axis during driving to correspond to a distance which the implant is driven. The corresponding geometry of the driver 405 and the recess 327 may be selected to have any appropriate cross section, e.g., rectangular or hexagonal.

The catheter has, at a distal end portion, a pair of retention tabs 415. The retention tabs 415 have inner diameters that are less than the diameter of the proximal head 325 but greater than the diameter of the other, more distal portions of the implant 300. Thus, the retention tabs allow the distal portions of the implant 300 to be driven beyond the distal end of the catheter and into tissue, but retains the head 325 within the catheter. After the driving of the implant 300, the retention tabs may be actuated radially outwardly away from each other to allow the release of the head of the implant 300 and withdrawal of the catheter 400 away from the implant site.

Referring to FIG. 21B, the catheter 600 shares many features in common with the catheter 400, including, e.g., retention tabs 615, but differs in that it includes a spring driver 605. The spring driver 605 imparts a spring force onto the proximal head 525 of the implant 500 to impart a rapid movement from an initial proximal position to an extended distal position. The spring driver 605 may have an initial preloaded position that is not in contact with the implant 500. Thus, the spring and/or a driver portion driven by the spring may build momentum prior to engaging the implant 500. This may be suitable for imparting a more aggressive acceleration to the implant 500. When the implant is able to achieve a high speed quickly, it is able to pierce a proximal face 551 of the tissue and penetrate across the thickness of the tissue to the distal face 552, rather than simply compressing the outer proximal surface 551 of the tissue. This may be particularly suitable in allowing a system that does not require any initial structure on the back side of the tissue during the driving process.

Figure 22:
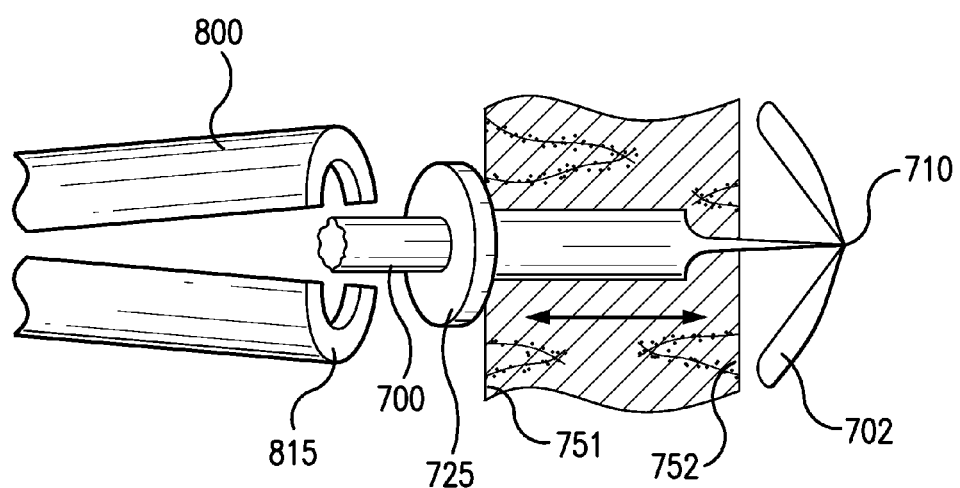
FIG. 22 is an illustration of a surgical implant with a driving mechanism.

FIG. 22 is a schematic illustration of a surgical implant 700 with a driving mechanism. This arrangement may be provided in connection with any of the fastener driving disclosed herein. The driving mechanism is a catheter 800 sharing features with the catheters 400 and 600 described above, including, e.g., retention tabs 815, which are shown in their opened, or radially extended position, thereby allowing distal axial passage therethrough of the head 725 of the implant 700.

The driver, e.g., the driver of FIG. 22 or any other example driver disclosed herein, may be configured to drive the any of the example fasteners described herein to a predetermined depth. The precision of the depth may be accomplished by any appropriate mechanism, e.g., a precise hydraulic driving force, engagement with flanges or other similarly stops, or a suture that tautens to limit the depth. Further the depth may be monitored using fluoroscopy or any other appropriate imaging mechanism. The driving mechanism may include pressurized saline or other hydraulic fluid that is pressurized through the endoscopic catheter shaft. Thus, very precise control may be accomplished.

According to example embodiments, a computer system may determine the location of two points, e.g., and determine a distance therebetween. The distance may be used as a desired distance to which the fastener is fired. The implanting distance may be set by any appropriate adjustment mechanism, e.g., an adjustable stop or flange, a cord or suture attached to the fastener, and/or precisely controlling the speed and momentum of the fastener during the implantation (e.g., by finely controlling a hydraulic propulsion system). Such measurements, determinations, and/or control of depth may be employed in conjunction with any implantation of fasteners disclosed herein.

The implant 700 includes many features in common with the implants 100, 200, 300, and 500 described above, but differs in that it includes a plurality of spring loaded tabs 702, which may be formed, e.g., of a shape memory alloy, e.g., nitinol or spring-loaded steel. The spring-loaded tabs are maintained in their closed, or radially inward, position when the proximal free ends of the tabs 702 are axially disposed in the catheter 800 (in its closed position) and in the tissue through which the tabs are driven after piercing of the tissue, including a proximal face 751, by the needle-like tip 710. However, when the proximal ends of the spring loaded tabs 702 clear the distal side 752 of the tissue, the tabs are no longer radially constrained by the tissue and are able to spring radially outwardly into their open position. In the open position, the implant 700 is prevented or constrained from being proximally withdrawn through the tissue via contact between the extended tabs 702 and the distal surface 752 of the tissue. The nut or head 725 of the implant 700 may then be rotated and distally advanced as described above with regard to the head 225 of the implant 200 in order to bring the layers of tissue together.

Figure 23:
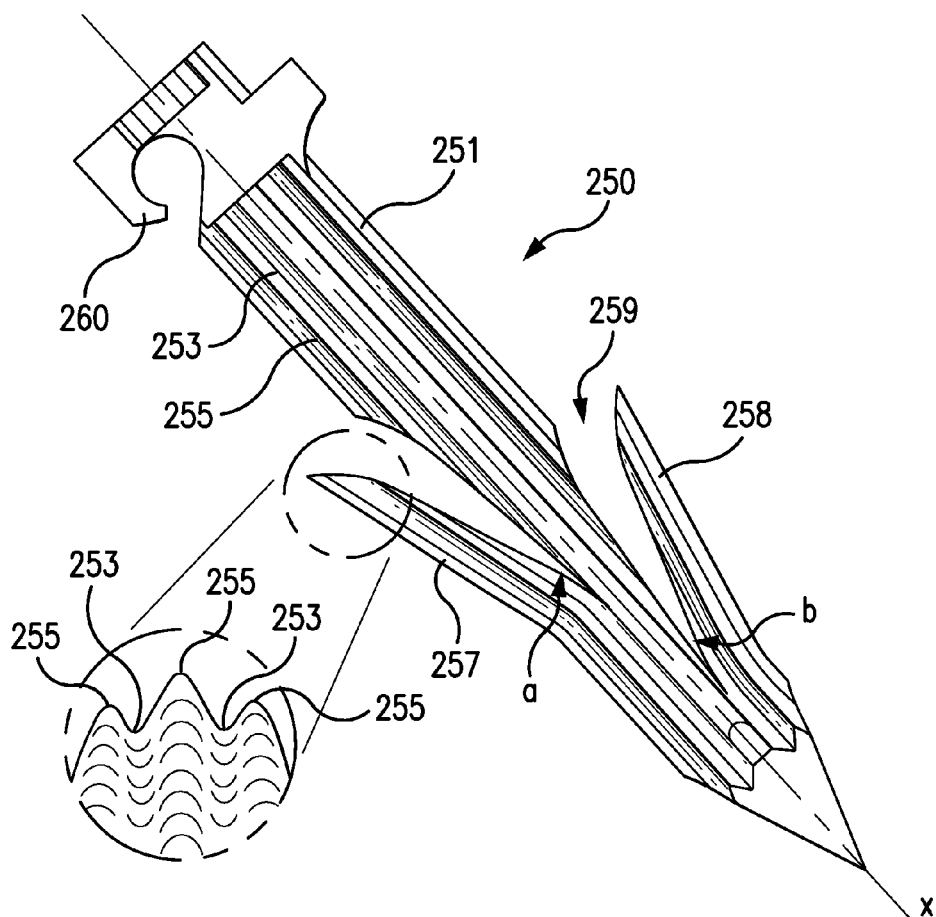
FIG. 23 is an illustration of a surgical implant.

FIG. 23 shows a fastener or implant 250. The fastener 250 includes many features in common with the other fasteners disclosed herein and may be used in conjunction with any of the other fastening applications described herein. However, the fastener 250 includes a corrugated body 251. The body 251 includes grooves 253 that extend axially along the length of the body 251. Thus, extending circumferentially around the body 251, a plurality of grooves 253 alternate with a plurality of ridges 255. Further, the fastener body 251 includes a pair of split portions or devises 257 and 258. The split portions are formed by respective splits or cuts 259 into the body 251. In this regard, the splits 259 may be formed by making a cut radially into the body 251 and extending in an axial direction. Thus, the two split portions 257 and 258 are attached to the remainder of the body 251 at a distal position and extend proximally to free ends. The free ends include a plurality of sharp protrusions along a curved surface. These points are formed due to the corrugations. In particular, the ridges 255 form the sharp protrusions, as illustrated in the inset partial side view in FIG. 4, which are advantageous for gripping tissue and preventing distal sliding of the fastener 250. Although each split portion 257 and 258 includes three such protrusions as illustrated, it should be understood, that the fastener 250 may be designed such that one or more of the split portions has any other number of protrusions, including a single sharp protrusion. For example, if a larger number of sharp protrusions are desired, the body 251 could be more densely corrugated (i.e., a greater number of alternating grooves 253 and ridges 255 could be provided) and/or the angle of the cut or slice could be adjusted. Further, the length of proximal extension of the projections may be adjusted by varying the depth of the grooves 253 with respect to the ridges 255.

The split portions 257 and 258 do not substantially impede distal insertion into tissue but resist proximal movement from an insertion location by engaging the tissue. It has been discovered that the combination of the pointed and/or sharp-edged proximal ends of the split portions 257 and 258 with the alternating ridges on the proximal end of the split portions creates improved performance.

Further, the split portions or wings 257 and 258 are axially offset from each other. For example, split 257 is axially located at position a along axis x and split 258 is axially located at position b along axis x. This allows for greater structural strength of the other portions of the body 251 as compared to a non-offset configuration. In particular, since the cuts progress continually radially inward as they progress distally, a non-offset portion would have a substantially smaller amount of material in cross-section in the distal end of the cut. This would lead to a mechanically weak point or region along the axis of the body and could lead to mechanical failure, especially in fasteners of small dimensions.

The distal tip of the fastener 250 is pyramidal, with a sharp point, and a plurality of surfaces separated by edges that converge at the sharp point. Although four planar surfaces are provided, it should be appreciated that any appropriate suitable number of surfaces may be provided and that one or more or all of the surfaces may be non-planar.

The fastener 250 also includes a hooked end portion 260. The hooked portion may be suitable for coupling any other temporary and/or permanent implant.

The fastener 250 may be produced by first forming the body 251 with the corrugations, e.g., by injection molding or extrusion, and subsequently forming clevises 257 and 258, e.g., by cutting radially into the side of the body 251. As illustrated, the cut is curved, with an angle (at the proximal entry point), relative to the longitudinal axis of the body 251, that gradually decreases from the proximal initial cutting location toward the distal end of the fastener 250 and eventually becoming linear. Although the spit or cut of the illustrated example is made with a curved or varying angle with respect to the longitudinal axis of the body 251, it should be understood that any appropriate cut, including a linear cut, may be made.

Although the fastener 250 includes two clevises spaced equally around the radial periphery of the body 251, it should be appreciated that any number of clevises, including a single clevis may be provided and at any appropriate spacing around the radial periphery.

Furthermore, it should be understood that the corrugated split-bodied configuration may be employed in combination with any of the other fastener features disclosed herein. For example, the fastener 250 may have a split corrugated distal portion and a threaded proximal portion configured to receive a proximal head as disclosed in greater detail above, and/or include filaments in addition to the split portions.

Figure 24:
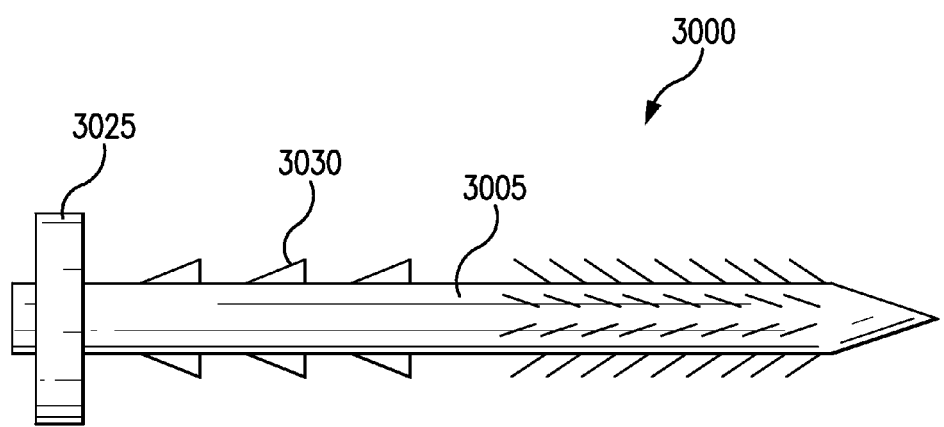
FIG. 24 is an illustration of a surgical implant.

FIG. 24 is an illustration of a surgical micro implant or fastener 3000. The fastener 3000 includes many feature of the other example fasteners described herein. Further, the fastener 3000 includes a proximal portion having a ratcheting mechanism including a micro ratcheting head 3025 and ratchet teeth 3030. The ratcheting mechanism of the implant 3000 performs a function analogous to that of the micro threaded arrangement of the fastener 200 described above. However, as opposed to rotation of the head 225 about the threads 230 of the fastener 200, the ratcheting head 3025 slides, e.g., linearly, along the fastener body 3005. As each ratchet tooth 3030 or circumferential set of ratchet teeth 3030 is distally traversed, the proximal retraction of the head 3025 is resisted or prevented by the ratcheting engagement of a proximal surface of the head 3025 with a distal surface of the ratcheting tooth or teeth 3030. In this regard, for each axial ratcheting position of the head 1025, the fastener body 3005 may have any appropriate number of ratcheting teeth 1030, including a single ratcheting tooth 3030, arranged to engage the ratcheting head 1025. Further, a single tooth 3030 may extend continuously around the entire radial periphery of the fastener body 3005.

Although the fastener 3000 includes micro filaments to anchor into a tissue and resist proximal dislocation after implantation, it should be understood that any other anchoring mechanism, e.g., devises as described above, may be provided. Moreover, any of the features disclosed with regard to the other example fasteners disclosed herein may be provided in conjunction with the fastener 3000.

Figure 25:
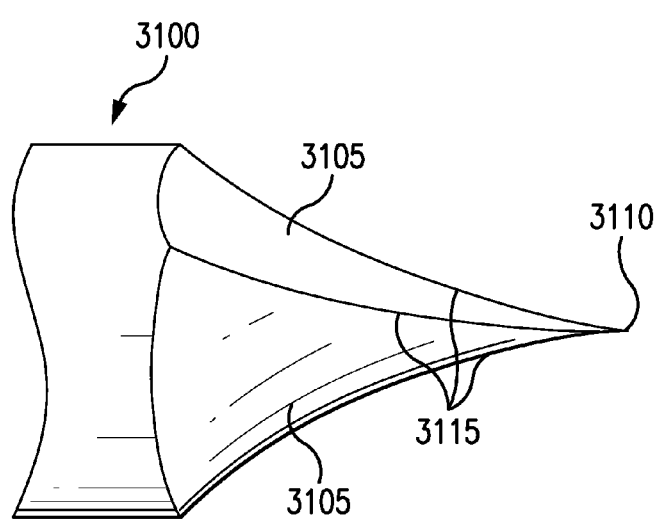
FIG. 25 is an illustration of a distal end portion of a surgical implant.

FIG. 25 is an illustration of a distal end portion of a surgical implant 3100. This distal arrangement may be provided on the distal end of any example fastener disclosed herein. The distal arrangement includes three concave surfaces 3105 that distally converge to form a sharp point 3110. Separating the three concave surfaces 3105 are three tapered cutting edges 3115. These tapered cutting edges 3115 may facilitate penetration of tissue, e.g., soft tissue. Although the end portion illustrated in FIG. 25 includes three concave surfaces 3105 separated by three corresponding tapered cutting edges 3115, it should be understood that any appropriated number of concave surfaces 3105 and corresponding cutting edges 3115 may be provided.

Any of the mechanisms and devices described above may be utilized with pressure sensing, e.g., sensing of the pressure required to progress a needle or fastener using any appropriate pressure sensing mechanism. The pressure may be relayed to, e.g., a computer control system in a hand piece to which the implanting device of any of the embodiments described herein is coupled. Further, imaging data may be obtained, including, e.g., ultrasound or other digital imaging, and relayed to, e.g., the computer control system in a hand piece. This information, including pressure and/or imaging information and/or any other sensed information may be used by the control system to appropriately control the insertion of the various needles and/or implants into the tissue. For example, the control system may control the rate, location, angle, and/or depth of insertion. Such precise control may be particularly advantageous when repairing defects in the heart, which requires very precise placement of implants.

The various mechanisms described herein provide for a tissue repair system that allows great flexibility. For example, smaller defects may be repairable with a single fastener (e.g., fastener 100 or any other fastener described herein), and larger defects may be repairable with a plurality of fasteners, with or without a washer or plate 2200, as described above. Larger defects, e.g., hernias or large holes, may be more suited for a mesh 1300 application, as described above.

The various implants described herein, e.g., fasteners 100, 200, 250, 300, 500, 700, 1400, 1600, 3000, and 3100, nuts 225 and 725, head 3025 and plates 2200, may be formed by molding, e.g., injection molding.

Further, any of the implantable elements described herein, e.g., fasteners 100, 200, 250, 300, 500, 700, 1400, 1600, 3000, and 3100, nuts 225 and 725, head 3025, mesh 1300, plates 2200, may be formed wholly or partly of a material absorbable into the patient's body, or of a non-absorbable material, depending on, e.g., the specific application. For example, these elements may be formed of polyglycolic acid (PGA), or a PGA copolymer. These elements may also, or alternatively, be formed of copolymers of polyester and/or nylon and/or other polymer(s). Moreover, these elements may contain one or more shape-memory alloys, e.g., nitinol and/or spring-loaded steel.

Absorbable materials may be advantageous where there is a potential for misfiring or improper locating of the various implants. For example, in a situation where a fastening arm 1100 drives a fastener at an unintended location, or where the tissue does not properly receive the implant, the fastener, e.g., fastener 100, even where not needed, would relatively harmless, as it would eventually absorb into the patient's body.

Although the present invention has been described with reference to particular examples and exemplary embodiments, it should be understood that the foregoing description is in no manner limiting. Moreover, the features described herein may be used in any combination.

What is claimed is:

1. An implant delivery device, comprising:
   a device body;
   an implant;
   a fastening arm, extendable from a distal end of the device body, the fastening arm having a lumen;
   at least one fastener situated in the lumen of the fastening arm;
   a fastener driver situated in the lumen of the fastening arm, wherein the fastener driver is configured to drive the fastener distally from the lumen into tissue; and
   a frame carrying the implant and extending within the device body, the frame being selectably movable between a retracted position in which the frame is collapsed and an extended position in which the frame is expanded to a predetermined shape to pull the implant taut and to conform the perimeter of the implant to the perimeter of the predetermined shape of the frame;
   wherein the frame is configured to detach from the implant after moving from the retracted position to the extended position.

2. The device of claim 1, wherein the implant is a mesh.

3. The device of claim 1, wherein the implant is a graft.

4. The device of claim 1, wherein the implant is a film.

5. The device of claim 1, wherein the implant is relaxed when the frame is in the retracted position and taut when the frame is in the extended position.

6. The device of claim 1, wherein the fastener driver is configured to fasten the implant to a patient's tissue when the frame is in the extended position.

7. The device of claim 6, wherein the frame is configured to detach from the implant when moving from the extended position to the retracted position after the implant has been fastened to the tissue.

8. The device of claim 1, wherein the device body includes a tubular portion that includes a distal opening.

9. The device of claim 8, wherein the tubular portion is a catheter.

10. The device of claim 9, wherein the frame moves distally through the distal opening of the tubular portion when the frame moves from the retracted position to the extended position.

11. The device of claim 8, further comprising a plurality of fastening arms extending through the tubular portion, each of the plurality of fastening arms having a retracted position and an extended position.

12. The device of claim 11, wherein, when the fastening arms are in their extended positions, the frame is slidable along the plurality of fastening arms when the frame moves from the retracted position to the extended position.

13. The device of claim 12, wherein a distal portion of each fastening arm includes a curved seat configured to receive and hold the frame when the frame is in the extended position.

14. The device of claim 13, wherein the curved seat of each fastening arm holds the frame at a position that allows the at least one fastener to be driven through the distal opening of the fastening arm into the implant supported by the frame.

15. The device of claim 14, wherein each of the fastening arms is configured to simultaneously drive one of the at least one fastener into the implant while the implant is held tautly by the frame.

16. The device of claim 11, wherein a distal end of each fastening arm is disposed adjacent a longitudinal axis of the tubular portion when the fastening arm is in the retracted position and the distal end of each fastening arm extends radially outwardly from the longitudinal axis of the tubular portion when the fastening arm is moved distally to the extended position.

17. The device of claim 1, wherein the frame is comprised of a shape memory alloy.

18. The device of claim 1, wherein the frame is comprised of nitinol.

19. The device of claim 1, wherein the frame is comprised of spring steel.

20. The device of claim 1, the fastener driver further comprising:
a spring; and
a firing pin having a proximal head and a distal end, the proximal head engaged with the spring;
wherein the firing pin is configured to slide axially within the lumen to impart an axial force from the spring to the fastener to drive the fastener distally from the lumen into tissue.

21. The device of claim 1, the fastener driver further comprising a drive shaft extending axially through the lumen configured to impart rotational force on the fastener to drive the fastener distally from the lumen into tissue.

22. The device of claim 1, the fastener driver further comprising a pushrod configured to impart an axial force to the fastener to drive the fastener distally from the lumen into tissue.

23. The device of claim 22, wherein the pushrod is externally threaded, the fastener driver further comprising an internally threaded pushrod driver configured to engage the externally threaded pushrod;
wherein the rotation of the internally threaded pushrod driver distally pushes the pushrod to impart an axial force to the fastener to drive the fastener distally from the lumen into tissue.

24. The device of claim 1, wherein the frame is configured to detach from the implant by slidably retracting along the perimeter of the implant.

25. An implant delivery device, comprising:
a device body;
a plurality of fastening arms extending from a distal end of the device body, each of the fastening arms having a lumen;
at least one fastener situated in the lumen of the fastening arm;
a fastener driver situated in the lumen of the fastening arm, wherein the fastener driver is configured to drive the fastener distally from the lumen into tissue;
an implant; and
a frame configured to carry the implant, the frame being extendible through the device body and slidably guided along the plurality of fastening arms between a retracted position in which the frame is collapsed and a deployed position in which the frame is expanded to form a perimeter shape of the implant and to pull the implant taut, the implant being relaxed when the frame is collapsed, the implant being taut when the frame is in the deployed position;
wherein the frame is configured to detach from the implant after moving from the retracted position to the deployed position.

26. The device of claim 25, wherein the implant is a mesh.

27. The device of claim 25, wherein the implant is a graft.

28. The device of claim 25, wherein the implant is a film.

29. The device of claim 25, wherein the fastener drivers are configured to drive fasteners into the implant when the frame is in the desired deployed position, thereby fastening the implant to an underlying tissue.

30. A medical device, comprising:
an implant;
a temporary frame configured to carry the implant, the temporary frame being selectably movable between a retracted position and a deployed position in which the temporary frame is expanded to a predetermined shape to conform the perimeter of the implant to the perimeter of the predetermined shape of the temporary frame, the implant being in a relaxed state when carried by the frame in the retracted position, the implant being in a taut state when carried by the frame in the deployed position;
a fastening arm having a lumen, wherein the frame is slidably guided along the fastening arm;
at least one fastener situated in the lumen of the fastening arm; and
a fastener driver situated in the lumen of the fastening arm, wherein the fastener driver is configured to drive the fastener distally from the lumen into tissue.

31. The device of claim 30, wherein the implant comprises at least one of a mesh, a graft, and a film.

32. A method, comprising:
deploying a temporary frame to tautly support an implant and to expand the temporary frame to a predetermined shape to conform the perimeter of the implant to the perimeter of the predetermined shape of the temporary frame;
positioning the implant in a predetermined location with respect to a tissue; and
fastening, by a fastener driver situated in a lumen of a fastening arm and at least one fastener situated in the lumen of the fastening arm, wherein the fastener driver is configured to drive the fastener distally from the lumen into tissue, the implant to the tissue in the predetermined location while the implant is tautly supported by the temporary frame.

33. The device of claim 32, wherein the implant comprises at least one of a mesh, a graft, and a film.

34. The method of claim 32, further comprising retracting the temporary frame after the implant has been fastened.

35. The method of claim 32, wherein the frame is comprised of a shape-memory material.

36. The method of claim 35, wherein the shape-memory material is nitinol.

37. The method of claim 32, wherein the fastening includes simultaneously driving a plurality of fasteners into the implant.

38. The method of claim 37, wherein the plurality of fasteners are simultaneously driven along a periphery of the implant.

39. A method, comprising:
supporting an implant with a temporary frame pulling the implant taut and expanding the temporary frame to a predetermined shape to conform the perimeter of the implant to the perimeter of the predetermined shape of the temporary frame;
positioning the temporary frame and the supported implant at a location with respect to a tissue; and
securing the implant to the tissue by a fastener driver situated in a lumen of a fastening arm and at least one fastener situated in the lumen of the fastening arm, wherein the fastener driver is configured to drive the fastener distally from the lumen into tissue, through the implant and into the tissue such that the fastener does not interfere with removal of the frame.

40. The method of claim 39, further comprising removing the temporary frame after the fasteners have been inserted.

41. The method of claim 39, wherein the implant is a mesh.

42. An implant delivery device, comprising:
a device body;
an implant; and
a frame carrying the implant and extending within the device body, the frame being selectably movable between a retracted position in which the frame is collapsed and an extended position in which the frame is expanded to a predetermined shape to pull the implant taut and to conform the perimeter of the implant to the perimeter of the predetermined shape of the frame;
wherein the frame is configured to detach from the implant by slidably retracting along the perimeter of the implant.

* * * * *